United States Patent [19]
Wolfe

[11] 3,948,927
[45] Apr. 6, 1976

[54] 2,2-DIMETHYL-3R-CARBOXY-6S-AMINO-1-OXA-4-AZA-5R-BICYCLO-[3,2,0]HEPTAN-7-ONE

[75] Inventor: Saul Wolfe, Kingston, Canada

[73] Assignee: Queen's University, Kingston, Canada

[22] Filed: Aug. 12, 1974

[21] Appl. No.: 496,620

Related U.S. Application Data

[63] Continuation of Ser. No. 242,842, April 10, 1972, abandoned.

[52] U.S. Cl. .......................................... 260/307 FA
[51] Int. Cl.² ...................................... C07D 498/04
[58] Field of Search ............................. 260/307 FA

[56] References Cited
UNITED STATES PATENTS
3,682,896  8/1972  Hardy .............................. 260/306.7

OTHER PUBLICATIONS
Shiro et al. – C.A. 72, 132,717k (1970).
Burger – "Medicinal Chemistry" – 2nd Edition, Interscience Publishers – p. 79 (1960).

*Primary Examiner*—Raymond V. Rush
*Attorney, Agent, or Firm*—Herbert W. Taylor, Jr.

[57] ABSTRACT

The title compound is produced by chemical synthesis and, if desired, converted as by N-phenylacetylation to a new β-lactam antibiotic such as oxapenicillin G.

2 Claims, No Drawings

2,2-DIMETHYL-3R-CARBOXY-6S-AMINO-1-OXA-4-AZA-5R-BICYCLO-[3,2,0]HEPTAN-7-ONE

CROSS-REFERENCE TO RELATED APPLICATION

This application is a continuation of my prior, copending application Ser. No. 242,842 filed Apr. 10, 1972 and now abandoned.

BACKGROUND OF THE INVENTION

1. Field of the Invention.

The processes of the present invention produce compounds both old and new which are useful intermediates in the synthesis of β-lactam antibiotics.

2. Description of the prior art.

Penicillins and cephalosporins comprise a group of well-known antibacterial agents commonly grouped together as a class called β-lactam antibiotics. For a recent review of this field with many citations (especially the first ten) to the prior work see J. P. Hou and J. W. Poole, β-lactam Antibiotics: Their Physicochemical Properties and Biological Activities in Relation to Structure, J. Pharmaceutical Sciences, 60(4), 503–532 (April, 1971). Most of the work in this field has fundamentally been done, speaking broadly, with 6-aminopenicillanic acid, 7-aminocephalosporanic acid and derivatives thereof produced by fermentation.

Considerable work has also been done on total chemical synthesis. A recent review is the text by M. S. Manhas and A. K. Bose, Synthesis of Penicillin, Cephalosporin C and Analogues, Marcel Decker, Inc., 95 Madison Avenue, New York, New York, 1969. An even more recent review is by R. B. Morin and B. G. Jackson, Chemistry of Cephalosporin Antibiotics, Fortschr Chem. Org. Naturst, 28, 343-14 403 (1970), especially pages 379–393; the now famous "Woodward Intermediate" is shown therein as Compound 146 on page 387.

Within recent months publications describing new work and summarizing and citing older work have appeared such as:

a. from Imperial College, London, and Glaxo jointly by D. H. R. Barton et al., J. Chem. Soc. (C), 1971, 3540–3550;

b. from Oxford University by D. M. Brunwin et al., J. Chem. Soc. (C), 1971, 3756–3762;

c. from the University, Newcastle upon Tyne, by B. G, Ramsay and R. J. Stoodley, J. Chem. Soc. (C), 1971, 3859–3876;

d. from Lilly by S. Kukolja, J. Amer. Chem. Soc. 93, 6267–6271 (1971);

e. from Lilly by G. F. Gutowski et al., Tetrahedron Letters No. 37, 3433–3436 (1971);

f. from Lilly a series of papers entitled Chemistry of Cephalosporin Antibiotics, e.g. No. 25 in J. Medicinal Chemistry 14(11), 1136–1138 (1971) and No. 21 in J. Org. Chem. 36(9), 1258–1267 (1971).

The anhydropenicillins used as starting materials in the present invention were first described by Saul Wolfe in J. Amer. Chem. Soc. 85, 643–644 (March, 1963), Belgium 621,452 and U.S. Pat. No. 3,311,638. Additional publications on anhydropenicillins by Saul Wolfe include Can. J. Chem. 46, 459 and 2549 (1968).

VArious azetidinones have been disclosed in patents such as Sheehan's U.S. 3,487,070-072 (Class 260–239) and 3,487,090 (Class 260–326) and, for example, Woodward's U.S. Pat. No. 3,483,215 (Class 260–306.7) and U.S. Pat. No. 3,449,336 (Class 260–243).

The oxazoline having the structure

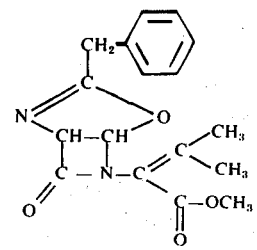

which is more commonly written as

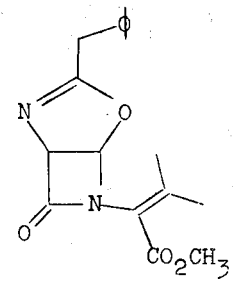

has been prepared from the methyl ester of benzylpenicillin in 18% yield, as by Barton et al., J. Amer. Chem. Soc., 91, 1529 (1969), and (a) above. Only one other bicyclic, sulfur-free compound of this type has been described [by F. G. Brain et al., J. Chem. Soc. Chem. Comm., 229–230 (1972)] but a rational synthesis of such esters or acids has not appeared.

The stereochemistry of the methyl ester of benzylpenicillin (i.e. the penicillin G produced by fermentation) is represented as follows:

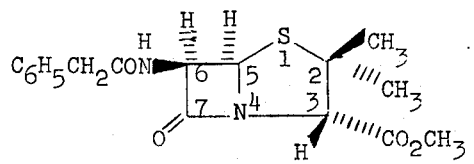

Kukolja [J. Amer. Chem. Soc. 93, 6267-6270 (1971)] chlorinated (with 2 equivalents of chlorine) methyl 6-phthalimidopenicillanate

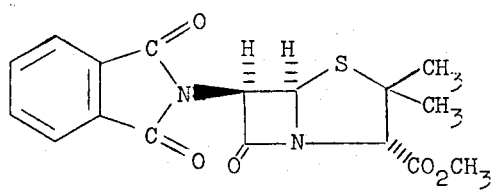

to produce a mixture of the two epimers having the structure

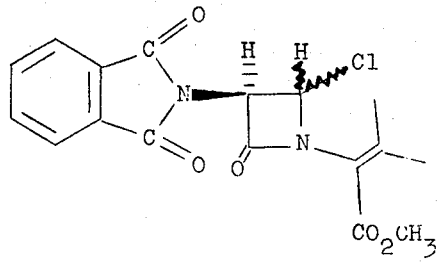

SUMMARY OF THE INVENTION

This invention provides a series of processes (and certain novel intermediates produced thereby) which begin with the chlorination of an anhydropenicillin.

The processes are set forth schematically in the usual manner directly below using for illustrative purposes as the starting material the phthalimido-anhydro-penicillin having the structure

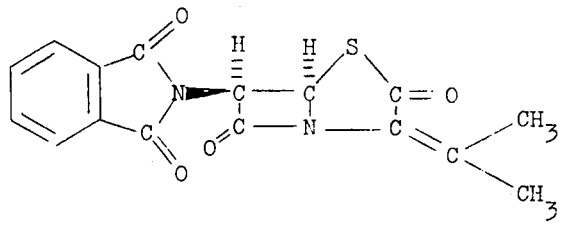

For simplicity that compound is written below as

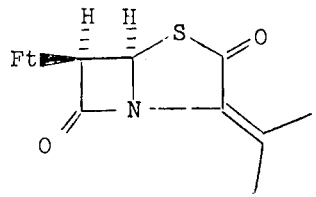

TFA represents trifluoroacetic acid; DIC is diisopropylcarbodiimide; NBS is N-bromosuccinimide; t-BuOH is tert.-butyl alcohol; Ph is phenyl.

This invention includes, but is not limited to, the reaction schemes set forth below as they are presented solely for purposes of illustration.

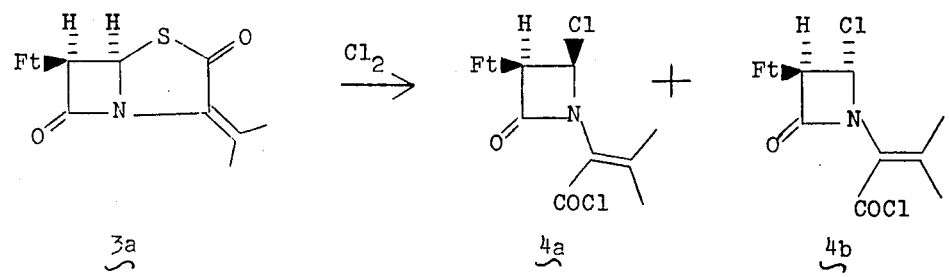

(see Kukolja, supra)

\* \* \*

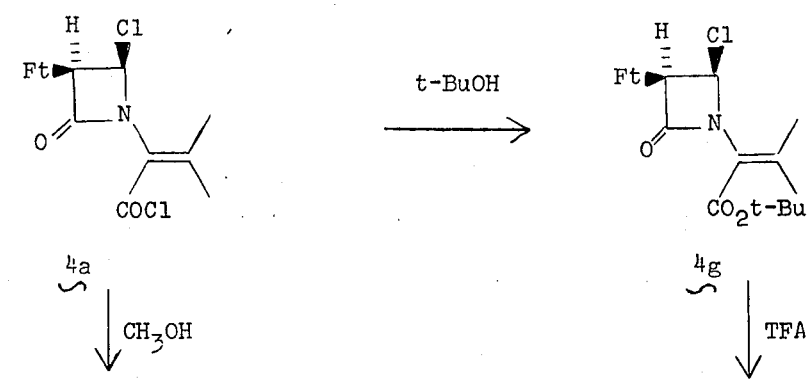

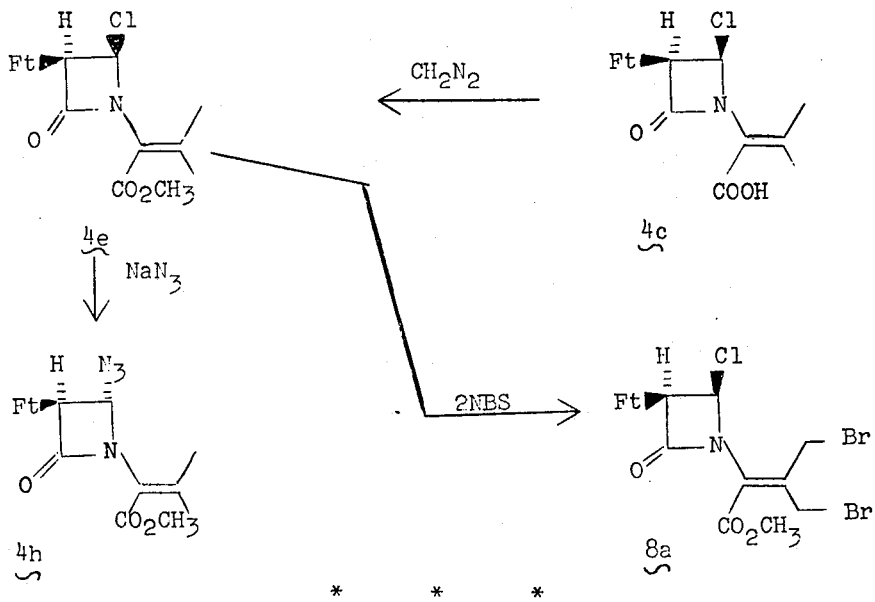

\* \* \*

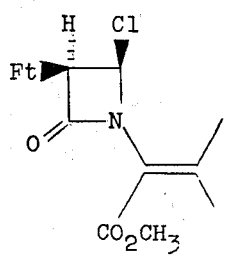
↓ 1 NBS
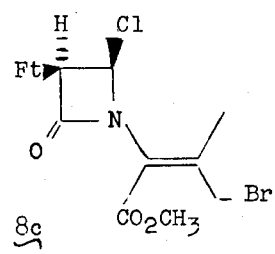 + 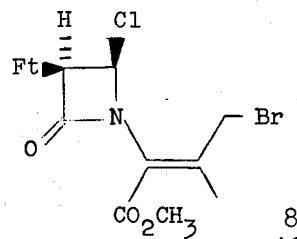
↓ N₃⁻
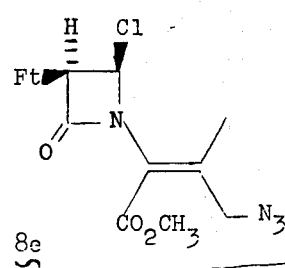 + 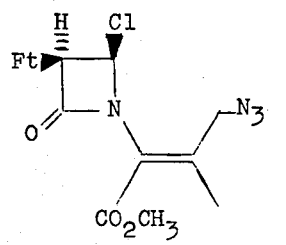
↓ PtO₂, H₂
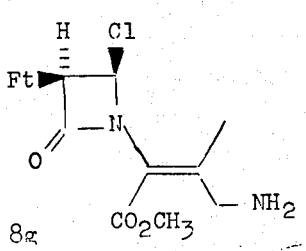 + 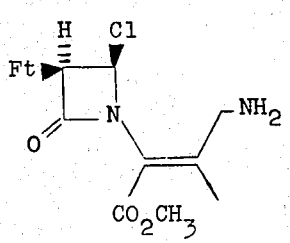
↓ KO-tBu
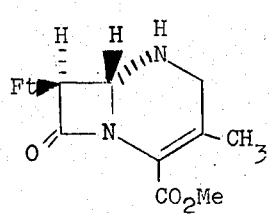
* * *

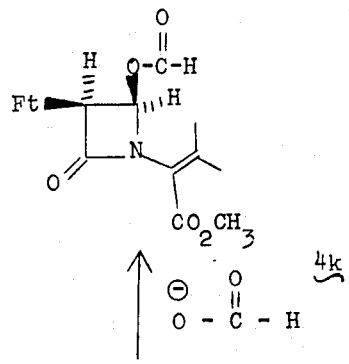
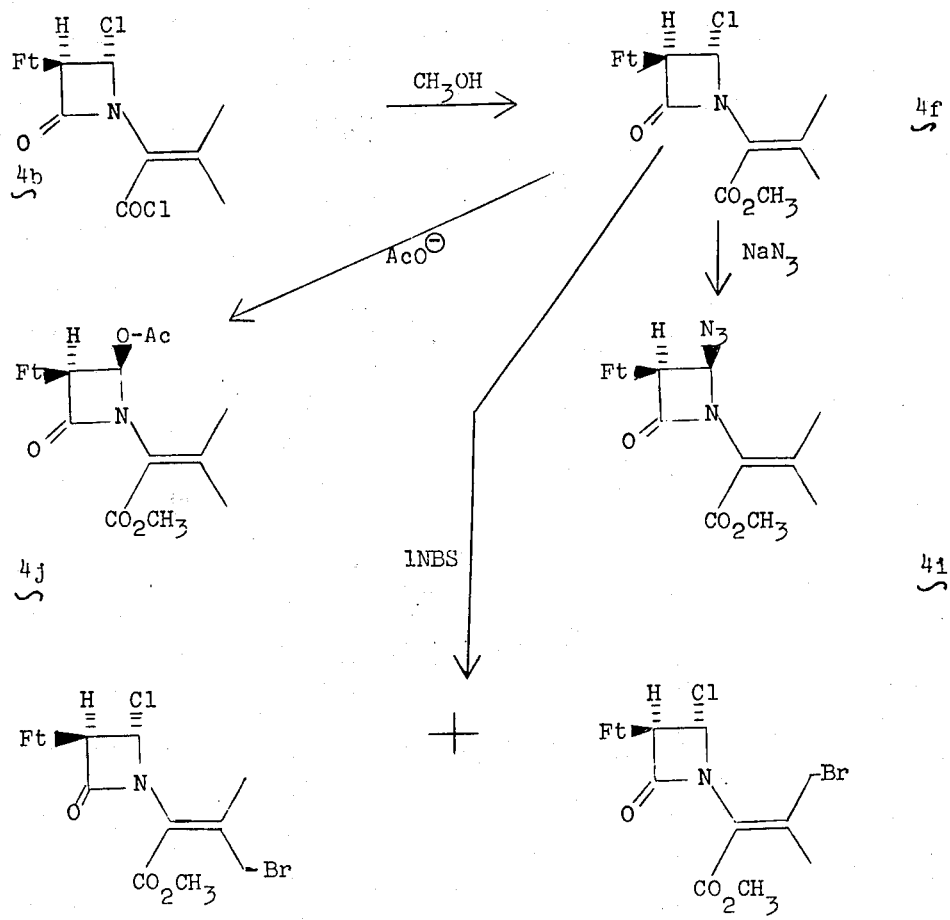
* * *
The above and additional processes and intermediates of the present invention are set forth below using as the starting material the toluenesulfonic acid (TsOH) salt of 6-aminoanhydropenicillin. This compound has the structure.
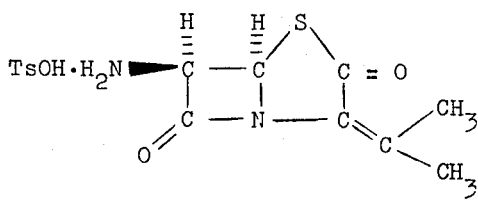
which for convenience is represented below as
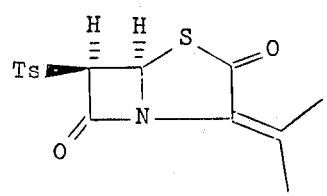
* * *

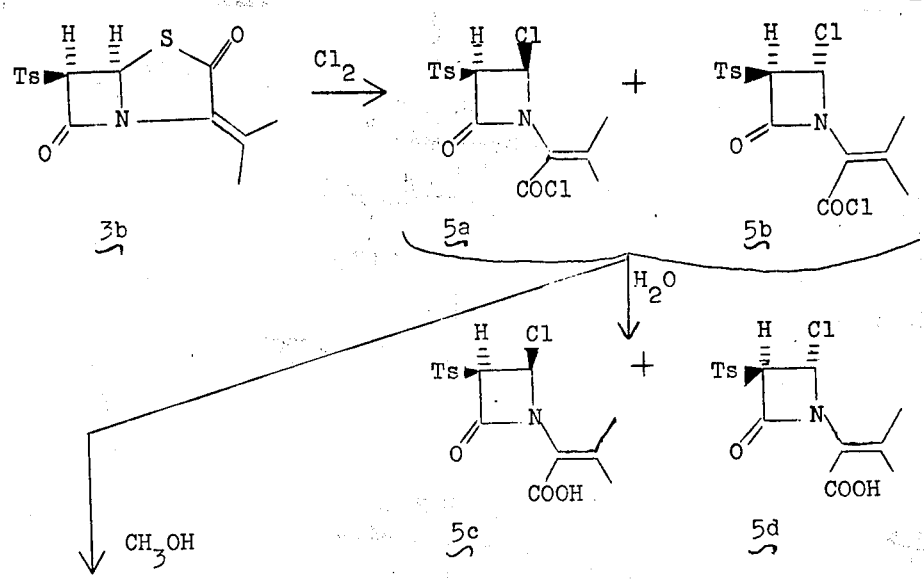
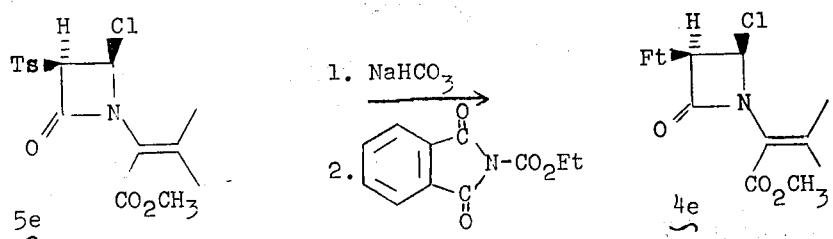
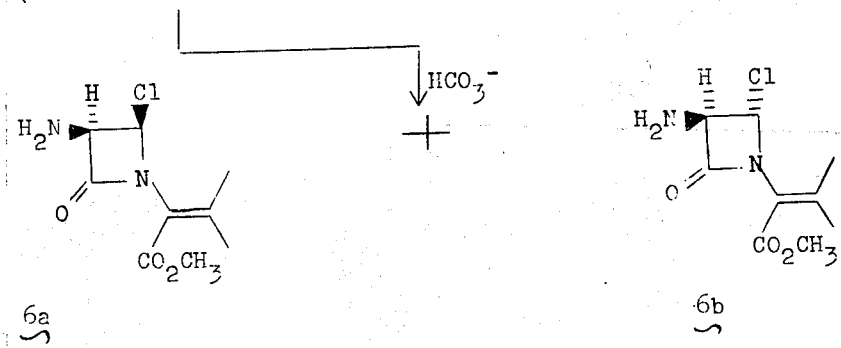
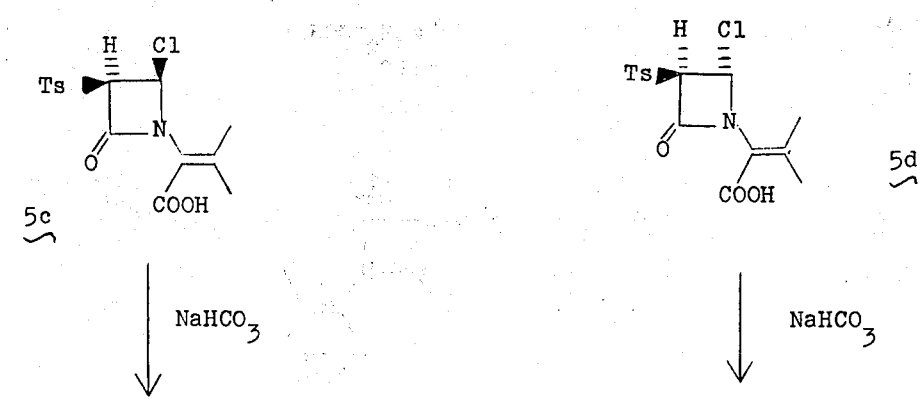

11 12
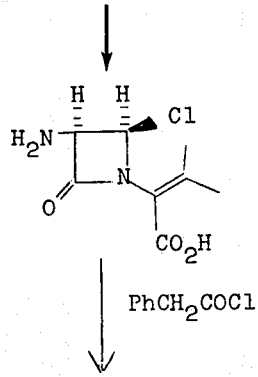 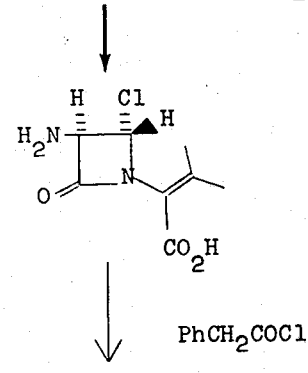
↓ PhCH₂COCl ↓ PhCH₂COCl
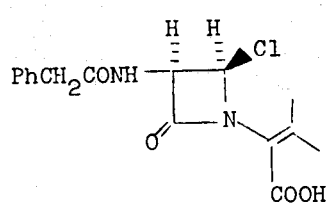 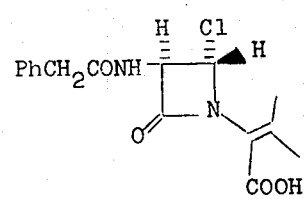
\* \* \*
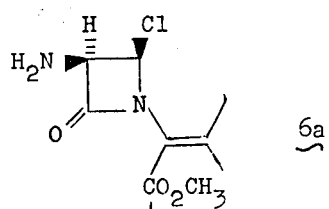
φCH₂COOH / DIC  N₃⁻
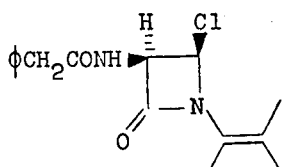 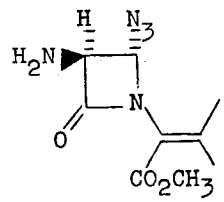
7a     6d
Silica gel    N₃⁻    φCH₂COOH / DIC
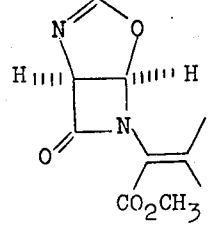 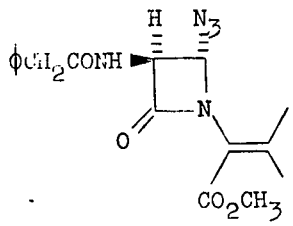
2                        7d

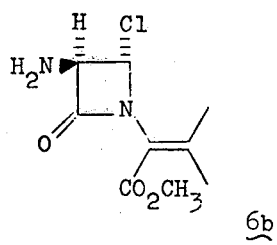
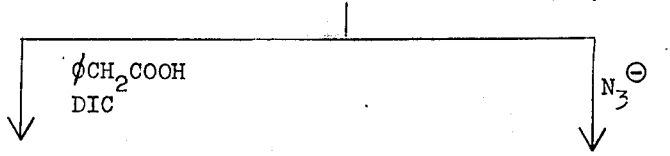
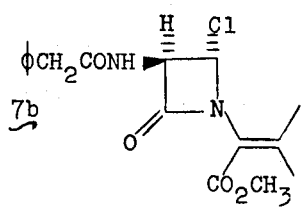 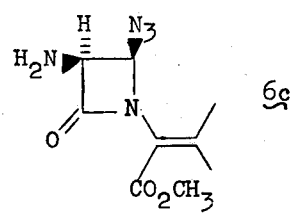
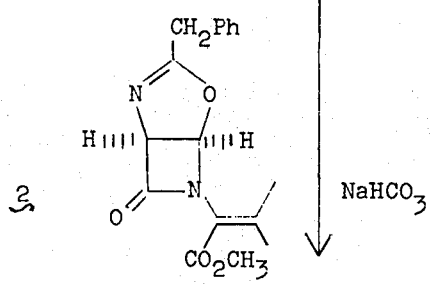 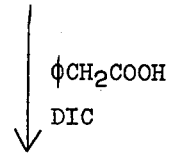
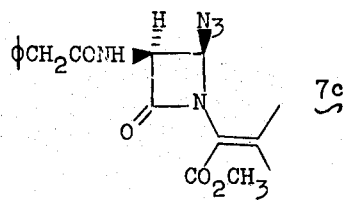
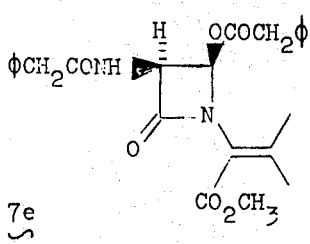 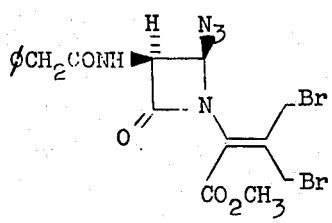
\* \* \*

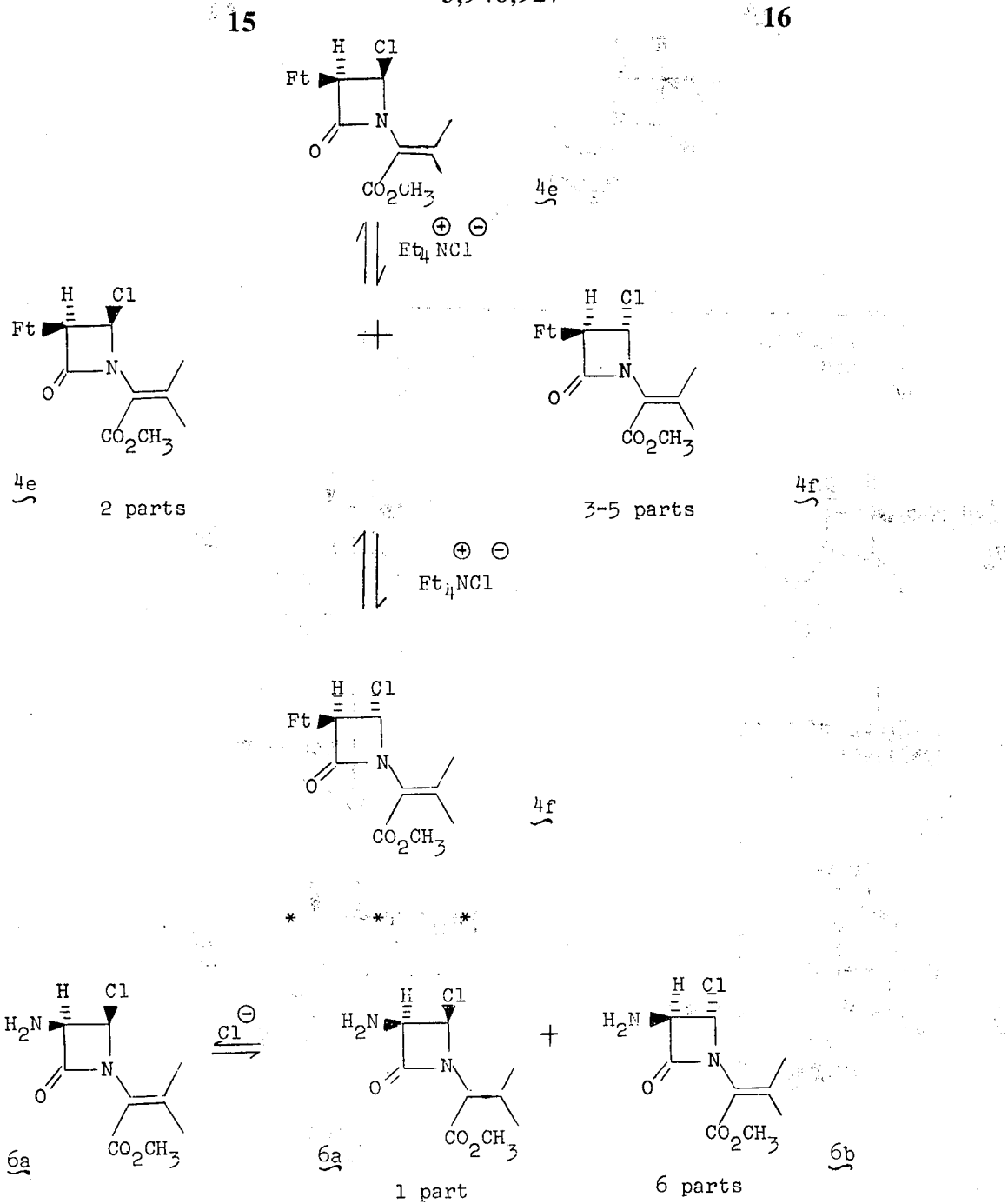

Thus, direct chlorination (excess $Cl_2$, $CH_2Cl_2$, 20°, 3 min.) of anhydro-6-phthalimidopenicillin (3a), followed by removal of the solvent under reduced pressure, afforded a 3:2 mixture of two isomeric compounds. The major isomer 4a, m.p. 210° dec., was obtained in 38% yield (from 3a) by crystallization from CHCl hd 3-petroleum ether (calcd. for $C_{16}H_{12}N_2O_4Cl$: C, 52.3; H, 3.31; N, 7.69; Cl, 19.4. Found: C, 52.03; H, 2.96; N, 7.76; Cl, 19.53), $\lambda_{max}^{FtOH}$ 242 (10000). The ir spectrum of 4a (and of the mixture of 4a and 4b) shows peaks at 5.48 (COCl), 5.55 ($\beta$-lactam), 5.62, 5.79 $\mu$(phthalimido).

Hydrolysis of 4a (boric acid-borax buffer [Saul Wolfe, R. N. Basse S. M. Caldwell, and F. I. Wasson, J. Amer. Chem. Soc., 91, 7205 (1969)]or aqueous acetone) gave the acid 4c, m.p. 168°–174° dec. in 73% yield (calcd. for $C_{16}H_{13}N_2O_5Cl$: C, 55.05; H, 3.76; N, 8.02; Cl, 10.02; Found: C, 54.65; H, 3.79; N, 8.46; Cl, 10.53); $\lambda_{max}^{FtOH}$ 236 (7400), 296 (1800); $\lambda_{max}^{KBr}$ 5.52, 5.60, 5.80, 5.85 $\mu$. Methylation of 4c ($CH_2N_2$, $Ft_2O$-$CH_2Cl_2$) produced the ester 4e, m.p. 178°–180° dec. in 97% yield. The same compound was obtained from 4a in 93% yield upon treatment with absolute methanol (30 min., 20°). Treatment of the mixture of 4a and 4b with methanol (20 min., 20°) and crystallization of the resultant residue ($CHCl_3$-petroleum ether) afforded 4e in 55% yield. Chromatography of the residual mother liquor (Woelm II alumina; 1:1 $Ch_2Cl_2$: $C_6H_6$) produced 22% of 4f, the methyl ester derivative of 4b, m.p. 192°–194°, in the first fractions followed by an additional 9% of 4e. The t-butyl ester 4g was obtained in 33% yield by refluxing 4a in anhydrous t-BuOH for 21 hr. Dissolution of 4g in trifluoroacetic acid and evaporation of the solvent after 3 min. gave 4a in quantitative yield.

The relative amountss of 4a and 4b were not significantly affected by chlorination in the presence of excess $Et_4N^+Cl^-$; other chlorinating agents ($SO_2Cl_2$, pyridinium trichloride, pyrrolidone hydrotrichloride) gave more complex mixtures. The essters 4e and 4f were equilibrated [Under identical experimental conditions the same mixture was obtained from both directions] upon refluxing ($Me_2CO$, 12 hr.; 2-butanone, 4 hr.) with excess $Et_4N^+Cl^-$, the trans isomer 4f predominating. Depending on the conditions, ratios varying from 3:2 to 5:2 could be obtained and the isomers could be separated by chromatography, as described above.

Reaction of 4e with sodium azide [4c decomposed when subjected to these conditions] (DMF, 90°, 3 hr.) afforded the trans azide 4h, m.p. 144°–145° (8%); under the same conditions 4f was converted to 4i, m.p. 183°–187° (52%). Reaction of 4f with $Et_4N^+OAc^-$ (pure $CHCl_3$, reflux, 17 hr.) gave the cis-acetate 4j (62%). Reaction of 4f with tetramethylguanidinium formate [a reagent invented for this purpose] afforded the cis-formate 4k (35%)

The above sequence of reactions was then repeated, with various modifications, on the p-toluenesulfonic acid salt [S. Wolfe, Can. J. Chem., 46, 459 (1968)] of anhydro-6-aminopenicillin (3b). Chlorination (0°–5°, $CH_2Cl_2$), followed by removal of the solvent and trituration with ether, afforded a 4:1 mixture of 5a and 5b as a stable (below 20°) white powder, m.p. 148°–149° dec. Hydrolysis of this powder (acetone-water) gave a 4:1 mixture of the acids 5c and 5d. Alternatively, methaol treatment of the mixture of 5a and 5b, and crystallization from chloroform-hexane produced the pure cis- methyl ester 5e, m.p. 125°– ° dec., in 67% yield. Neutralization of 5e ($NaHCO_3$) and reaction of the free base 6a with N-carbethoxyphthalimide [G. H. L. Nefkens, Nature, 185, 309 (1960)] gave 4e to provide confirmation that the chlorination reaction had proceeded in the same manner with the two anhydropenicillins.

Equilibration of 6a with the trans isomer 6b proceeded smoothly in the presence of chloride ions, the optimum ratio in favor of 6b (6:1) being achieved with tetramethylguanidinium chloride ($CH_2Cl_2$, 12 hr. reflux). The isomers were separated by alumina chromatography. The cis amino chloride 6a reacted smoothly with tetramethylguanidinium azide [A. J. Papa, J. Org. Chem., 31, 1426 (1966)] (2equiv., $CHCl_3$, 1 hr. reflux) to give the trans amino azide 6d (90%); the cis amino azide 6c, m.p. 116°–117°, was obtained similarly from 6b in 85% yield.

The 5-chloropenicillin G analog 7a, m.p. 111°–115° dec., was obtained (82%) upon phenylacetylation of 6a ($PhCH_2COOH$, diisopropylcarbodiimide (DIC), $CH_2Cl_2$). The C5 epimer 7b, obtained similarly from 6b, cyclized spontaneously to the oxazoline 2 [J. C. Sheehan, "Molecular Modification in Drug Design", Advances in Chemistry Series, No. 45, American Chemical Society, Washington, D.C., 1964, page 15.; D. H. R. Barton, F. Comer and P. G. Sammes, J. Amer. Chem. Soc., 91, 1529 (1969)], m.p. 126.5°–127°; additional quantities of 2 were obtained from 7a by rapid chromatography on silica gel or alumina [If the trans-acylamino chloride 7b was shaken with bicarbonate varying quantities (up to 10%) of 7e could be isolated in addition to the oxazoline]. The 5-azidopenicillin G analog 7c, m.p. 102°–103°, was obtained (83 %) upon phenylacetylation of 6c($PhCH_2COOH$, DIC, $CH_2Cl_2$); the C5 epimer 7d was obtained similarly from 6d or by reaction of 7a with tetramethylguanidinium azide ($CHCl_3$, reflux).

Allylic oxidation of 4e by N-bromosuccinimide (NBS, 2 equiv., $CCl_4$, benzoyl peroxide, Photoflood No. 2 bulb [S. Wolfe, and D. V. C. Awang, Can. J. Chem., 49, 1384 (1971); This result should be contrasted to the behavior of the parent anhydropenicillin towards allylic oxidation; S. Wolfe, C. Ferrari and W. S. Lee, Tetrahedron Letterss, 3385 (1969). As already noted, S. Wolfe, R. N. Bassett, S. M. Caldwell, and F. I. Wasson, J. Amer. Chem. Soc., 91, 7205 (1969), enamine character of the double bond of these compounds is not seen in the monocyclic systems]) was complete within 5 min. The product 8a crystallized from $CCl_4$-petroleum ether in 81% yield, m.p. 70 –72° dec. Under the same conditions the $C_5$ epimer 4f afforded 8b (70%). The extraordinary facility of this NBS oxidation is seen in the successful functionalization, under the same conditions, of 7c and 2. The methyl groups of 4e and 4f show no significant difference in reactivity. Thus, oxidation of 4e with one equivalent of NBS afforded a 1:1 mixture of 8c and 8d. Treatment of this mixture with tetramethylguanidinium azide (one equivalent, $CHCl_3$, 3 hr., 20° [The 5-chloro substituent is stable under these conditions.]) afforded a 1:1 mixture of 8e and 8f; $\lambda_{max}^{CHCl}$ 4.7 (azide), 5.55 ($\beta$-lactam), 5.62, 5.79 (phthalimido), 5.78 (ester). Hydrogenation ($PtO_2$, benzene, 45 psi, 6 hr.) yield the mixture of amines 8g and 8h; $\lambda_{max}^{CHCl}$ 5.55, 5.62, 5.79, 5.83 $\mu$. This mixture was recovered unchanged following refluxing in chloroform. Treatment with KOtBu-tBuOH (20°, 1 hr.), followed by carful chromatography (neurtral alumina, activity II, elution with graded mixtures of $Ch_6H_6$-$CH_2Cl_2$) produced in 12% yield (24% if only one of 8g or 8h reacted) a crystalline compound, m.p. 121°–122° having structure 9 on the basis of its ir ($\lambda_{max}^{KBr}$ 2.92, 5,56, 5.62, 5.79, 5.82, 6.03 $\mu$) and nmr (2.25 (4H), 3.87 (1H,d,2.0 Hz), 4.30 (1H,d,2.0 Hz), 6.23 (3H), 7.70 (2H), 7.88 (3H)) spectra.

Another important embodiment of the present invention is schematically illustrated, with R indicating n-propyl or tert. butyl and HMPT indicating

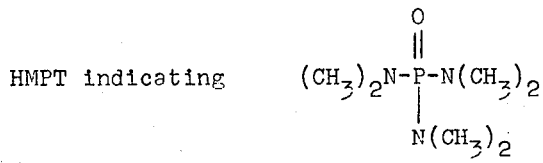

as follows:

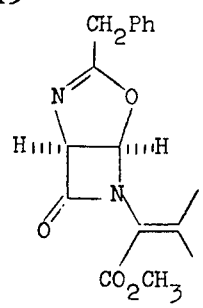
1. RSLi/HMPT
2. $H_3O^+$
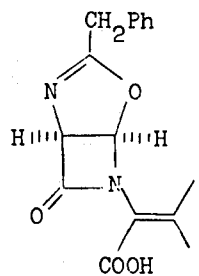 + 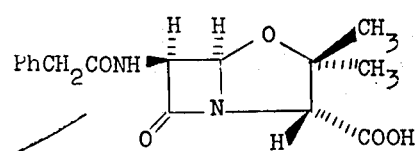
(as in U.S. patent 3,499,909)
1. $(CH_3)_3SiCl$
2. $PCl_5$
3. $CH_3OH$
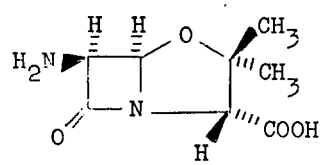
* * *
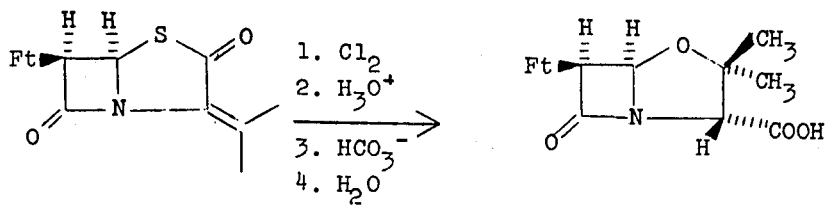
1. $Cl_2$
2. $H_3O^+$
3. $HCO_3^-$
4. $H_2O$
$H_2N \cdot NH_2$ or $CH_3NH_2$
(as in S. Wolfe and S.K. Hasan, Can. J. Chem., 48, 3572 (1970)).
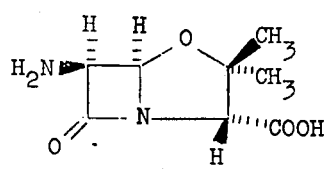
* * *

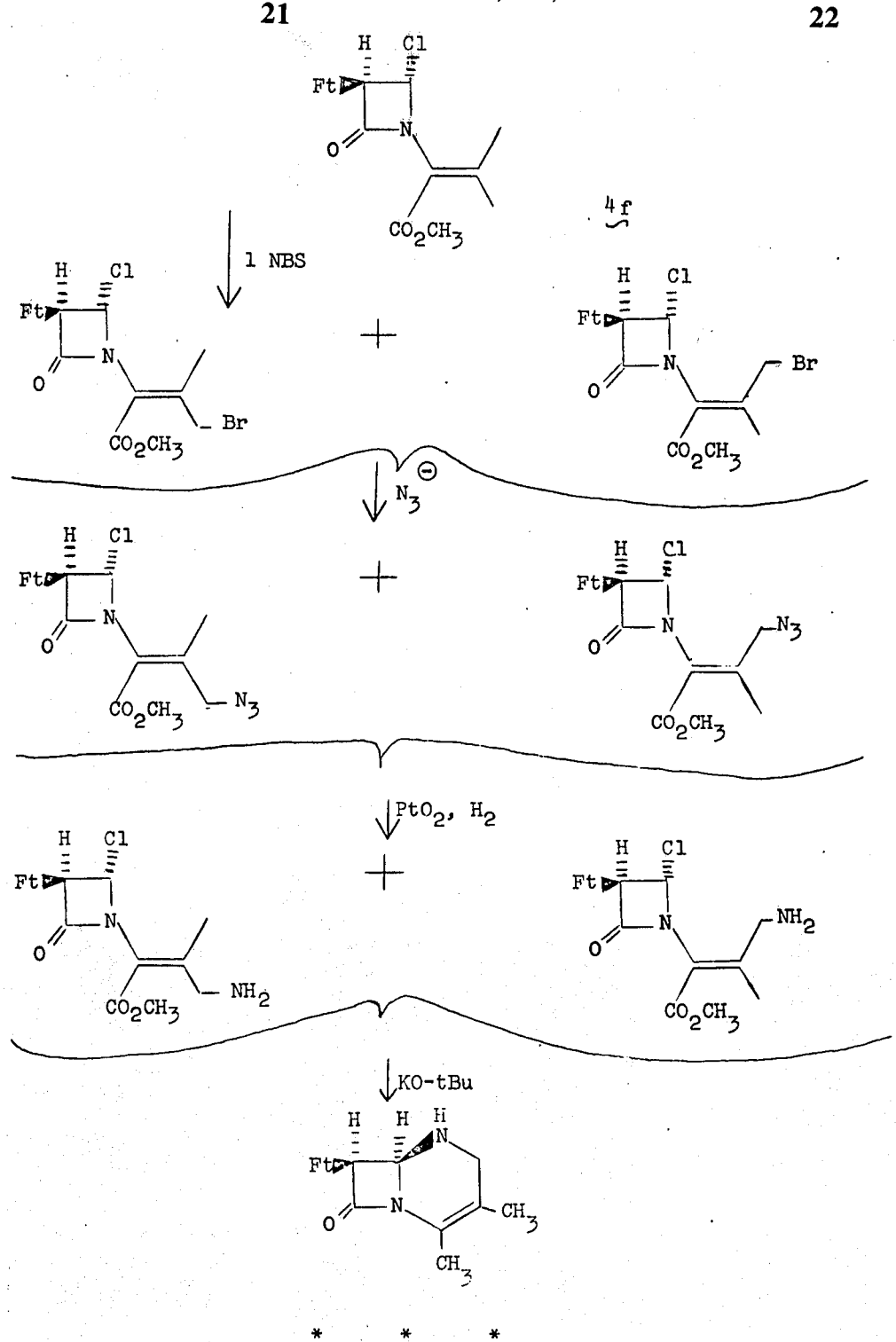

4f

More generally speaking, the processes described above and in the examples are conducted with numrous side-chains at the 6-position, e.g. using as the original reagent an anhydropenicillin having the formula

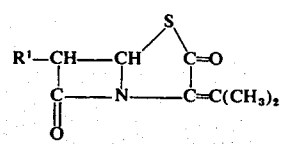

wherein $R^1$ represents acylamino, including phthalimido, or amino.

Thus in the processes herein disclosed use is also made in place of the phthalimido group (Ft) or the free amino group or its tosylate (Ts) of the corresponding reagents, intermediates and products in which each of these groups is replaced by an acylamino group $R^1$ of the formula

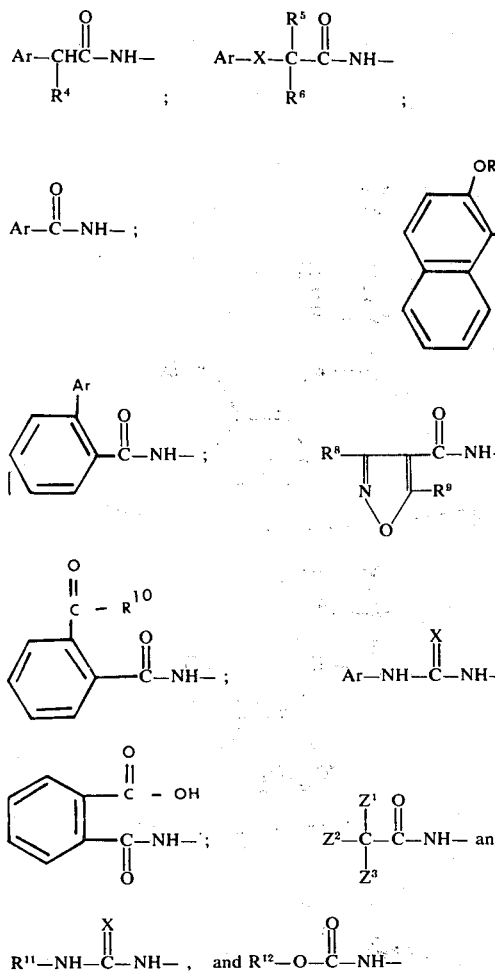

wherein $R_4$ represents a member selected from the group consisting of hydrogen, amino, carbobenzoxyamino, phenyl, fluoro, chloro, bromo, iodo, hydroxy, (lower)alkanoyloxy and (lower)alkoxy; X represents a member selected from the group consisting of oxygen and sulfur; $R^5$ and $R^6$ each represent a member selected from the group consisting of hydrogen, phenyl, benzyl, phenethyl and (lower)alkyl; $R^7$ represents (lower)alkyl; $R^8$ and $R^9$ each represent a member selected from the group consisting of (lower)alkyl, (lower)alkylthio, benzylthio, cyclohexyl, cyclopentyl, cycloheptyl, benzyl, phenethyl, phenylpropyl, furyl, thienyl, naphthyl and Ar-; $R^{10}$ represents a member selected from the group consisting of (lower)alkylamino, di(lower)alkylamino, cycloalkylamino having from 3 to 7 carbon atoms inclusive, allylamino, diallylamino, phenyl(lower)alkylamino, morpholino, lower(alkyl)morpholino, di(lower)alkylmorpholino, morpholino(lower)alkylamino, pyrrolidino, (lower)alkylpyrrolidino, di(lower)alkylpyrrolidino, N,N-hexamethyleneimino, piperidino, (lower)alkylpiperidino, di(lower)alkylpiperidino, 1,2,5,6-tetrahydropyridino, N-(lower)alkylpiperazino, N-phenylpiperazino, N-(lower)alkyl(lower)alkylpiperazino, N-(lower)alkyl-di-(lower)alkylpiperazino, furfurylamino, tetrahydrofurfurylamino, N-(lower)alkyl-N-furfurylamino, N-alkyl-N-anilino and (lower)alkoxyanilino; $Z^1$, $Z^2$ and $Z^3$ each represent a member selected from the group consisting of (lower)alkyl and Ar-; $R^{11}$ represents a member selected from the group consisting of (lower)alkyl, (lower)cycloalkyl, naphthyl, benzyl, phenethyl and

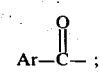

$R^{12}$ represents 2,2,2-trichloroethyl or benzyl and Ar- represents a monovalent radical having one of the formula

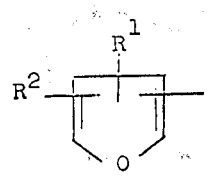 , 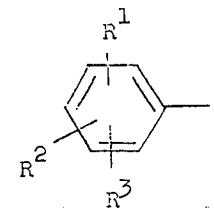

and

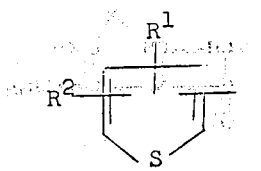

wherein R¹, R² and R³ are each a member selected from the group consisting of hydrogen, chloro, bromo, iodo, trifluoromethyl, phenyl, (lower)alkyl and (lower)alkoxy, but only one of said R¹, R² and R³ may represent phenyl.

Thus, for example, a preferred group of intermediates and final products of the present invention are illustrated in terms of final products by acids having the following formulae:

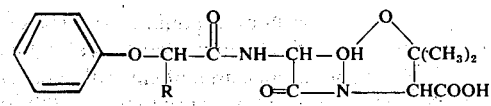

wherein R represents (lower)alkyl;

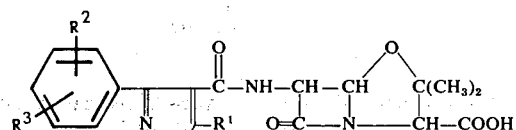

wherein R¹ represents (lower)alkyl and R² and R³ each represent a member selected from the group consisting of hydrogen and chloro;

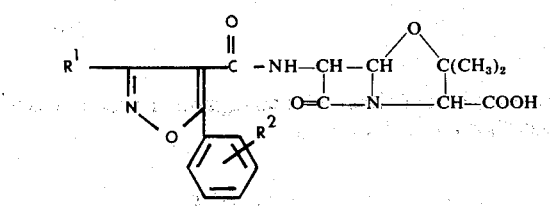

wherein R¹ is (lower)alkyl and R² is a member selected from the group consisting of hydrogen and chloro;

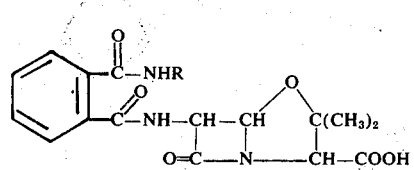

wherein R represents (lower)alkyl;

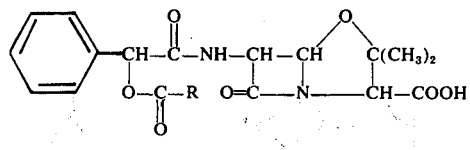

wherein R is (lower)alkyl;

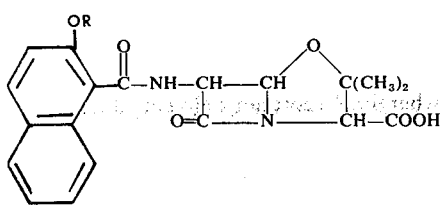

wherein R is (lower)alkyl;

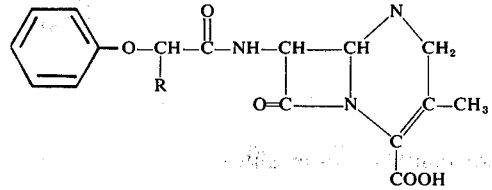

wherein R represents (lower) alkyl;

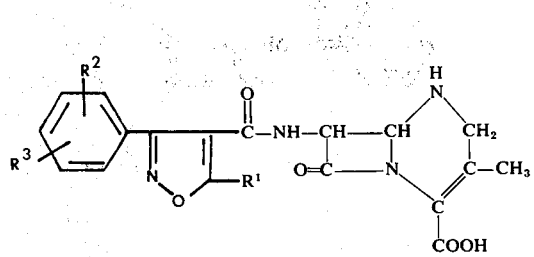

wherein R¹ represents (lower)alkyl and R² and R³ each represent a member selected from the group consisting of hydrogen and chloro;

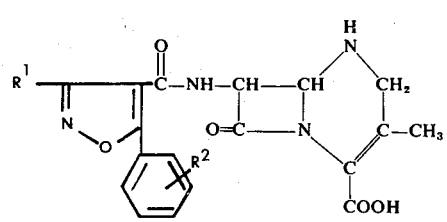

wherein R¹ is (lower)alkyl and R² is a member selected from the group consisting of hydrogen and chloro;

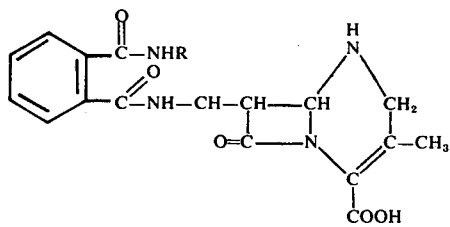

wherein R represents (lower)alkyl;

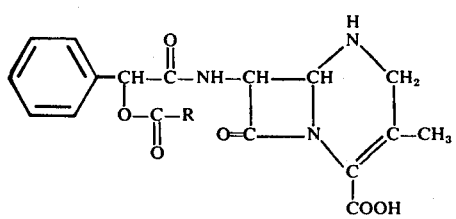

wherein R is (lower)alkyl;

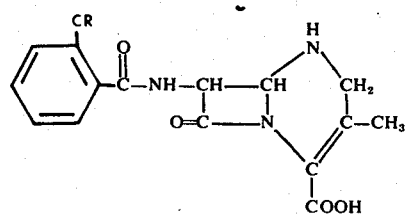

wherein R is (lower)alkyl.

The present invention provides the process for the production of an antibacterial agent which comprises reacting a compound of the formula

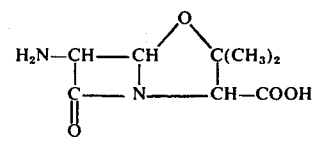

or a salt thereof with an organic monocarboxylic acid chloride or a functional equivalent thereof, and also the process for the production of an antibacterial agent which comprises reacting a compound of the formula

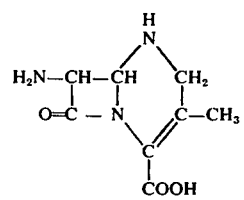

or a salt thereof with an organic monocarboxylic acid chloride or a functional equivalent thereof.

In a preferred embodiment the present invention provides the process for the production of an antibacterial agent which comprises reacting a compound of the formulae

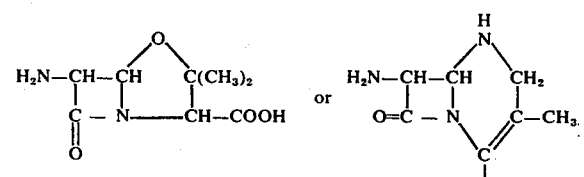

or a salt thereof either with an organic monocarboxylic acid chloride of the formula

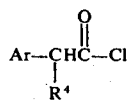 ; 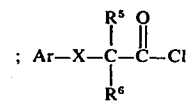 ;

 ; 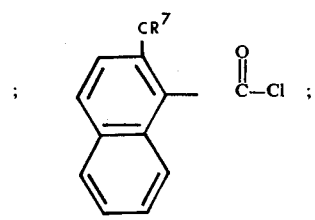 ;

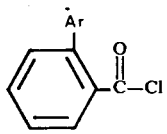 ; 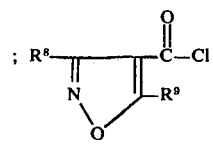 ;

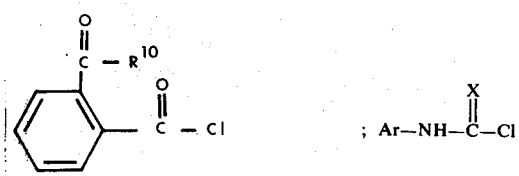

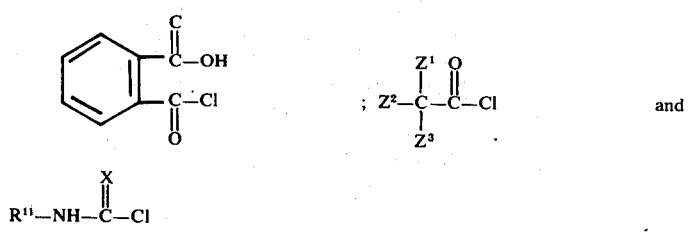

R¹¹—NH—C(=X)—Cl wherein R¹ represents a member selected from the group consisting of hydrogen, amino, carbobenzoxyamino, phenyl, fluoro, chloro, bromo, iodo, hydroxy, (lower)alkanoyloxy and (lower)alkoxy; X represents a member selected from the group consisting of oxygen and sulfur; R⁵ and R⁶ each represent a member selected from the group consisting of hydrogen, phenyl, benzyl, phenethyl and (lower)alkyl; R⁷ represents (lower)alkyl; R⁸ and R⁹ each represent a member selected from the group consisting of (lower)alkyl, (lower)alkylthio, benzylthio, cyclohexyl, cyclopentyl, cycloheptyl, benzyl, phenethyl, phenylpropyl, furyl, thienyl, naphthyl and Ar—; R¹⁰ represents a member selected from the group consisting of (lower)alkylamino, di(lower)alkylamino, cycloalkylamino having from 3 to 7 carbon atoms inclusive, allylamino, diallylamino, phenyl(lower)alkylamino, morpholino, (lower)alkylmorpholino, di(lower)alkylmorpholino, morpholino(lower)alkylamino, pyrrolidino, (lower)alkylpyrrolidino, di(lower)alkylpyrrolidino, N,N-hexamethyleneimino, piperidino, (lower)alkylpiperidino, di(lower)alkylpiperidino, 1,2,5,6-tetrahydropyridino, N-(lower)alkylpiperazino, N-phenylpiperazino, N-(lower)alkyl(lower)alkylpiperazno, N-(lower) alkyl-di-(lower)alkylpiperazino, furfurylamino, tetrahydrofurfurylamino, N-(lower)alkyl-N-furfurylamino, N-alkyl-N-anilino and (lower)alkoxyanilino; Z¹, Z² and Z³ each represent a member selected from the group consisting of (lower)alkyl and Ar-; R¹¹ represents a member selected from the group consisting of (lower)alkyl, (lower)cycloalkyl, naphthyl, benzyl, phenethyl and Ar—C(=O)— ;

and Ar- represents a monovalent radical having one of the formulae

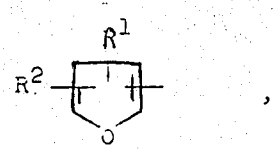

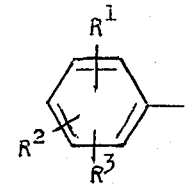

and

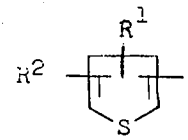

wherein R¹, R² and R³ are each a member selected from the group consisting of hydrogen, chloro, bromo, iodo, trifluoromethyl, phenyl, (lower)alkyl and (lower)alkoxy, but only one R group may represent phenyl; or with a functional equivalent of said acid chloride.

The term "(lower)alkyl" as used herein means both straight and branched chain aliphatic hydrocarbon radicals having from one to ten carbon atoms such as methyl, ethyl, propyl, isopropol, butyl, isobutyl, t-butyl, amyl, hexyl, 2-ethylhexyl, heptyl, decyl, etc. Similarly, where the term "(lower)" is used as part of the description of another group, e.g. "(lower)alkoxy", it refers to the alkyl portion of such group which is therefore as described above in connection with "(lower)alkyl".

The functional equivalents of the above acid chlorides as an acylating agent for a primary amino group include the corresponding carboxylic acid bromides, acid anhydrides, including mixed anhydrides and particularly the mixed anhydrides prepared from stronger acids such as the lower aliphatic monoesters of carbonic acid of alkyl and aryl sulfonic acids and of more hindered acids such as diphenylacetic acid. In addition, an acid azide or an active ester or thioester (e.g. with p-nitrophenol, 2,4-dinitrophenol, thiophenol, thioacetic acid) may be used or the free acid itself may be coupled with the primary amine after first reacting said free acid with N,N'-dimethylchloroformiminium chloride [cf. Great Britain 1,008,170 and Novak and Weichet, Experientia XXI/6, 360 (1965)] or by the use of enzymes or of an N,N'-carbonyldiimidazole or an N,N'-carbonylditriazole [cf. South African Patent Specification 63/2684], of a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess, J. Amer. Chem. Soc. 77, 1067, (1955)], or of alkynylamine reagent [cf. R. Buijle and H. G. Viehe, Angew. Chem. International Edition 3, 582 (1964)], or of a ketenimine reagent [cf. C. L. Stevens and M. E. Monk, J. Amer. Chem. Soc. 80, 4065 (1958)] or of an isoxazolium salt reagent [cf. R. B. Woodward, R. A. Olofson and H. Mayer, J. Amer. Chem. Soc. 83, 1010 (1961)]. Another equivalent of the acid chloride is a corresponding azolide, i.e. an amide of the corresponding acid whose amide nitrogen is a member of a quasi-aromatic five-membered ring containing at least two nitrogen atoms, i.e. imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolides. The by-product, imidazole, precipitates and may be separated and the imidazolide isolated but this is not essential. The methods for carrying out these reactions to produce a penicillin and the methods used to isolate the penicillins so-produced are well-known in the art.

The nontoxic, pharmaceutically acceptable salts include metallic salts such as sodium, potassium, calcium and aluminum, the ammonium salt and substituted ammonium salts, e.g. salts of such nontoxic amines as trialkylamines, including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, N-(lower)alkylpiperidines, e.g. N-ethylpiperidine, and other amines which have been used to form salts with benzylpenicillin.

There are particularly included within the scope of the present invention the antibacterial agents which are prepared in the above-described acylation process by the use therein of the organic monocarboxylic acids or their acid chlorides or other equivalents which have previously been used to acylate 6-aminopenicillanic acid as described, for example, in U.S. Pat. Nos. 2,941,995; 2,951,839; 2,985,648; 2,996,501; 3,007,920; 3,025,290; 3,028,379; 3,035,047; 3,040,032; 3,040,033; 3,041,332; 3,041,333; 3,043,831; 3,053,831; 3,071,575; 3,071,576; 3,079,305; 3,079,306; 3,080,356; 3,082,204; 3,093,547; 3,093,633; 3,116,285; 3,117,119; 3,118,877; 3,120,512; 3,120,513; 3,120,514; 3,127,394; 3,140,282; 3,142,673; 3,147,247; 3,174,964; 3,180,863; 3,198,804; 3,202,653; 3,202,654; 3,202,655; 3,210,337; 3,157,639; 3,134,767; 3,132,136; in British Patent Specification Nos. 874,414; 874,416; 876,516; 876,662; 877,120; 877,323; 877,531; 878,233; 880,042; 880,400; 882,335; 888,110; 888,552; 889,066; 889,069; 889,070; 889,168; 889,231; 890,201; 891,174; 891,279; 891,586; 891,777; 891,938; 893,518; 894,247; 894,457; 894,460; 896,072; 899,199; 900,666; 902,703; 903,785; 904,576; 905,778; 906,383; 908,787; 914,419; 916,097; 916,204; 916,205; 916,488; 918,169; 920,176; 920,177; 920,300; 921,513; 922,278; 924,037; 925,281; 931,567; 932,644; 938,066; 938,321; 939,708; 940,488; 943,608; 944,417; in numerous Belgian Pat. Nos., e.g. 593,222; 595,171; 597,859; 602,494; 603,703; 609,039; 616,419; 617,187; and in South African Patent Application Nos., e.g. 60/2882; 60/3057; 60/3748; 61/1649; R61/2751; 62/54; 62/4920; 63/1612 and 63/2423.

When the acylamino group of the compounds of the present invention also contains a strongly basic group, e.g. primary amino, as in the case of the preferred embodiments having the formulae

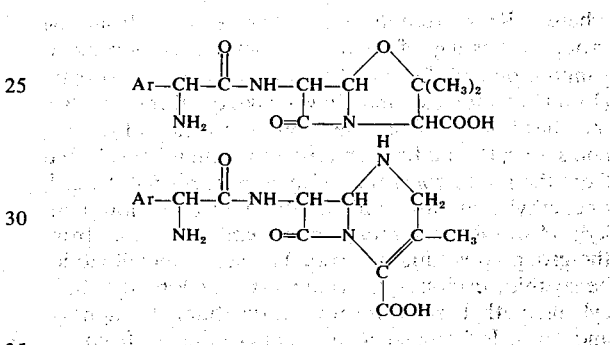

and
wherein Ar is as defined above (and $R^1$, $R^2$ and $R^3$ in Ar are preferably hydrogen), the products are amphoteric and normally exist in the zwitterion form but can form acid addition salts, as with such nontoxic, pharmaceutically acceptable organic acids as acetic, citric, succinic, ascorbic and the like and with inorganic acids such as hydrochloric, hydrobromic, sulfuric, phosphoric and the like.

The processes of the present invention also include the use as "final reagents" of the compound of the formula

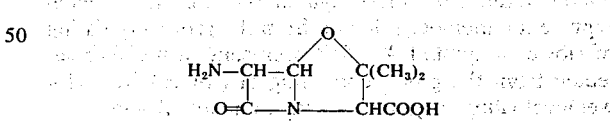

and its salts with acids and bases and the compound of the formula

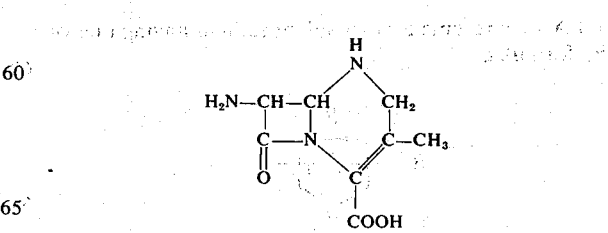

and its salts with acids and bases.

These "final reagents" are prepared, for example, by subjecting to hydrogenolysis the compound of the formula

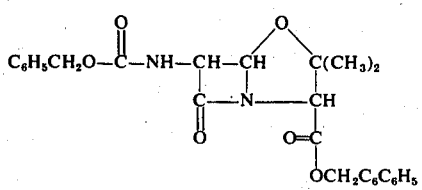

or by subjecting to hydrogenolysis the compound of the formula

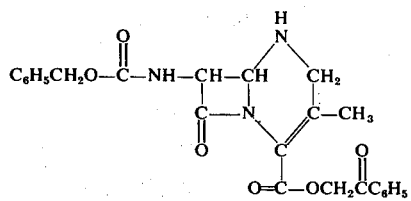

or by subjecting to acid cleavage either the compound of the formula

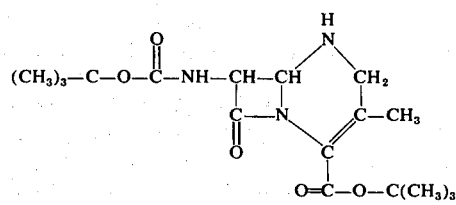

or the compound of the formula

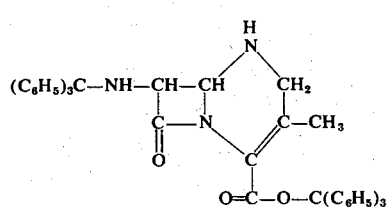

or by treating with zinc and acetic acid the compound of the formula

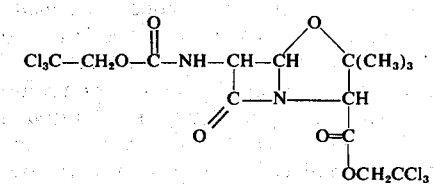

or the compound of the formula

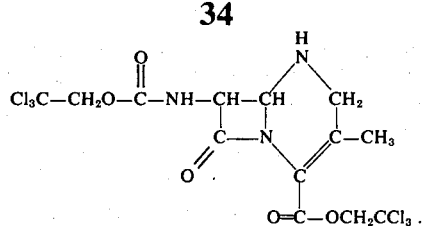

Such esters are prepared, for example, by using as the starting material an anhydropenicillin of the formula

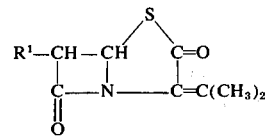

in which $R^1$ is

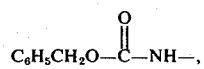

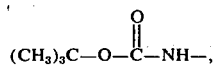

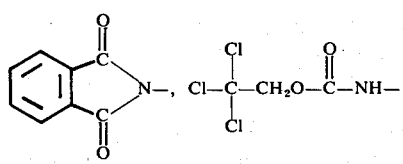

formyl, o-nitrophenylsulfenylamino or o-nitrophenoxyacetamido or one of its equivalents as described in U.S. Pat. No. 3,271,409; and in the appropriate later step (of reaction with acid chloride) substituting for the methanol either t-butyl alcohol or trityl alcohol or trichloroethyl alcohol; or in the later step (of reaction with carboxylic acid) substituting for the diazomethane either diphenyldiazomethane, 2,2,2-trichloroethyl chloroformate, benzyl chloroformate, or t-butyl chloroformate.

These esters are then converted to "final reagents" by removal of the ester and conversion of the blocked amino group to a free amino group, either consecutively or simultaneously. Thus, when the blocked amino group represents phthalimido, it is converted to primary amino by treatment with hydrazine hydrate in dioxane at about room temperature for at least 12 hours or with methylamine in aqueous dioxane. When the blocked amino group represents carbobenzyloxyamino it is converted to a primary amino group by catalytic hydrogenation to leave the product.

When the blocked amino group is formyl, carbo-t-butyloxy-amino or o-nitrophenylsulfenylamino it is converted to primary amino either by reaction with anhydrous hydrogen chloride in a nonprotonating solvent such as benzene or methylene chloride or by reaction with trifluoroacetic acid. The trichloroethoxycarbonylamino is converted to primary amino by reaction with zinc in aqueous acetic acid. In addition, when the blocked amino group is carbo-t-butyloxyamino, the final two reactions are conducted in one step by the use of stronger acid for longer periods of time and, if desired, at higher temperatures.

When the blocked amino group is o-nitrophenoxyacetamido, it is converted into a primary amino group by either (a) catalytic hydrogenation (e.g. in water at room temperature using 30% Pd-on-diatomaceous earth) followed by allowing the mixture to stand at an acidic pH (e.g. in water acidified to pH 2 with 20% hydrochloric acid at about 10° C. for at least 20 minutes or at 25° C. for at least 24 hours) or (b) by adding the blocked compound (e.g. 7 millimoles) in cold water, e.g. 30 ml., rapidly, e.g. over 1–3 minutes, to 5% Pd-C (e.g. 0.05 g.) suspended in a cold solution of $KBH_4$, (e.g. 14 millimoles) dissolved in water, e.g. 70 ml.

Chlorination of Anhydro-6-Phthalimidopenicillin

Chlorine gas was passed at room temperature into a solution of anhydro-6-phthalimidopenicillin (500 mg., 1.52 mmoles) in methylene chloride (15 ml.). The gas introduction was terminated after 3 minutes and, after an additional 5 minutes, the yellow solution was evaporated to dryness. The resulting white foam was crystallized from a mixture of chloroform and petroleum ether to give a total of 250 mg. (32%) of material in two crops, m.p. 210° dec. The IR spectrum of the residual mother liquor was identical to that of the crystalline material, summarized below.

Anal. Calcd. for $C_{16}H_{12}N_2O_4Cl_2$: C, 52.3; H, 3.31; N, 7.69; Cl, 19.4.

Found: C, 52.03; H, 2.96; N, 7.76; Cl, 19.53.

The IR spectrum shows peaks in the carbonyl region at 5.48, 5.55, 5.62 and 5.79μ. The NMR spectrum shows peaks at 2.13 (4H), 3.78(1H,d,J=4.2 Hz), 4.24 (1H,d,J=4.2 Hz), 7.60 (3H), 7.69 (3H). The uv spectrum shows $\lambda_{max}^{EtOH}$ 242 (10,000).

The compound has the structure

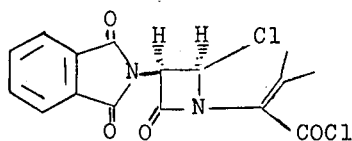

Hydrolysis of the Dichloride

The dichloride (500 mg., 1.36 mmoles), in dimethyl sulfoxide, (500 ml.) was treated, dropwise at 0°, with 50 ml. of a pH 7.95 buffer (prepared by diluting 50 ml. of 0.1M boric acid and 2.6 ml. of 0.1M NaOH to 100 ml.). At the end of the addition, the pH of the reaction mixture was 6.8. This mixture was allowed to warm to room temperature, and stirring was continued for 3.25 hours. Then ice-cold water (300 ml.) was added, the mixture brought to pH 3 with ice-cold N HCl, and extracted with five 100 ml. portions of methylene chloride. The combined extracts were washed twice with water (100 ml. portions) and dried over anhydrous sodium sulfate. Evaporation under reduced pressure at 40° afforded a mobile liquid which contained a considerable amount of DMSO. This was redissolved in chloroform (60 ml.) and the solution washed ten times with water (10 ml. portions). After drying and evaporation there was obtained from the chloroform phase 0.59 g. of a crystalline white solid. This was recrystallized from a mixture of chloroform and petroleum ether giving a total of 350 mg. (73%) of short white needles, m.p. 168°–174° dec.

Anal. Calcd. for $C_{16}H_{13}N_2O_5Cl$: C, 55.05; H, 3.76; N, 8.02; Cl, 10.02.

Found: C, 54.65; H, 3.79; N, 8.46; Cl, 10.53.

The IR spectrum shows peaks in the carbonyl region at 5.52, 5.60, 5.80 and 5.85μ. The NMR spectrum shows peaks at 2.13 (4H), 3.78 (1H,d,J=4.1 Hz), 4.29 (1H,d,J=4.1 Hz), 7.67 (3H), 7.69 (3H). The u.v. spectrum shows $\lambda_{max}^{EtOH}$ 236 (7400), 296 (1800).

The compound has the structure

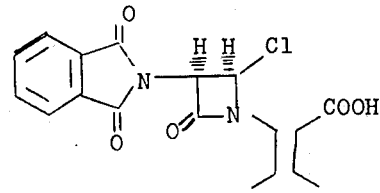

Conversion of the Acid to the Methyl Ester

The acid (200 mg., 0.57mmole) was dissolved in 30 ml. of a 1:1 mixture of methylene chloride and ether. The solution was cooled and treated with excess ethereal diazomethane. The solution which resulted was stirred for 0.5 hour, allowed to warm to room temperature during an additional 1 hour, and then evaporated at 40° to a white crystalline residue. Recrystallization from a mixture of chloroform and petroleum ether gave 0.20 g. (97%) of colorless fine needles, m.p. 178°–180° dec.

The compound has the structure

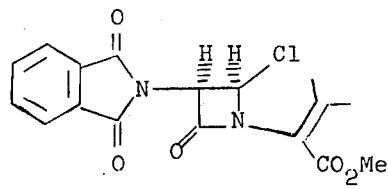

Conversion of The Acid Chloride to the Methyl Ester

The crystalline acid chloride (500 mg., 1.43 mmoles) was dissolved in methylene chloride (10 ml.) and absolute methanol (10 ml.) was added. The mixture was stirred at room temperature for 30 minutes, then diluted with methylene chloride (50 ml.) and washed successively with ice-cold 5% bicarbonate solution (10 ml.) and water. After drying over anhydrous magnesium sulfate and removal of the solvent a crystalline residue was obtained. This was recrystallized from methylene chloride - petroleum ether to give 463 mg. (93%) of methyl ester identical to that described above.

Anal. Calcd. for $C_{17}H_{15}N_2O_5Cl$: C, 56.3; H, 4.16; N, 7.71; Cl, 9.78.

Found: C, 56.58; H, 4.37; N, 7.55; Cl, 9.82.

The NMR spectrum shows peaks at 2.10 (m,4H), 3.77 (1H,d,J=4.1 Hz), 4.23 (1H,d,J=4.1 Hz), 6.18 (3H), 7.57 (3H), 7.66 (3H).

Direct Conversion of Anhydro-6-Phthalimidopenicillin Into A Mixture of Methyl 2-(2'R-chloro-3'S-phthalimido-4'-oxo)azetidinyl-3-methyl-2-butenoate and its 2'S epimer Chlorine gas was passed at room temperature into a solution of anhydro-6-phthalimidopenicillin (1.0 g., 3.04 mmoles) in methylene chloride (30 ml.). After 3 min. the gas introduction was terminated and, after an additional 5 min. the solvent was removed under reduced pressure at 30°. The solid residue was redissolved in methylene chloride (20 ml.) and absolute methanol (20 ml.) was added. This solution was stirred at room temperature for 30 min. and then evaporated to dryness under reduced pressure at 40°. The residue was crystallized from chloroform-petroleum ether to give 600 mg. (55%) of the ester having the 2'R-chloro configuration. The mother liquor was chromatographed on a 1.5 × 14 cm column of alumina (Woelm, grade II). Elution with 1:1 methylene chloride - benzene afforded 202 mg. (18%) of a new compound in the first 25 ml., followed by 93 mg. of a mixture of the 2'R-ester and the new compound in the next 25 ml. Elution with methylene chloride (40 ml.) then afforded an additional 68 mg. of the 2'R-ester.

The new compound was crystallized from methylene chloride-petroleum ether to give the ester having the 2'S-chloro configuration, m.p. 192°-194°.

Anal. Calcd. for $C_{17}H_{15}N_2O_5Cl$: C, 56.3; H, 4.16; N, 7.71; Cl, 9.78.

Found: C, 56.42; H, 4.43; N, 7.68; Cl, 9.60.

The NMR spectrum shows peaks at 2.17 (4H,m), 3.77 (1H,d,J= 2.0 Hz), 4.4 (1H,d,J= 2.0 Hz), 6.17 (3H), 7.7 (3H), 7.92 (3H).

The structure of this compound is

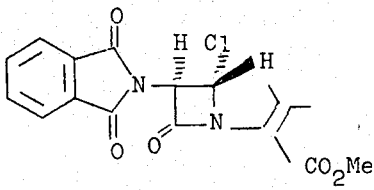

Stereoselectivity of the Chlorination of Anhydro-6-Phthalimidopenicillin

Anhydro-6-phthalimidopenicillin (0.5 g., 1.52 mmoles) was chlorinated in methylene chloride, as already described. The NMR spectrum of the total product showed peaks at 2.12 (4H,m), 3.78 (0.6H,d,J=4.2 Hz), 3.77 (0.4H,d,J=1.8 Hz), 4.25 (0.6H,d,J=4.2 Hz), 4.33 (0.4H,d,J=1.8 Hz), 7.57 (1.8H), 7.65 (1.2H), 7.68 (1.2H), 7.77 (1.2H).

The chlorination reaction is therefore stereoselective under these conditions, a 60:40 mixture of the 2'R-chloro: 2'S-chloro epimers being obtained under these conditions.

Crystallization of the product from methylene chloride-petroleum ether afforded 300 mg. (38%) of the pure dichloride having the 2'R-configuration. The mother liquor was then dissolved in absolute methanol (10 ml.) and the solution allowed to stand for 30 min. at room temperature with occasional shaking. It was then diluted with methylene chloride and washed successively with ice-cold sodium bicarbonate solution and water, and dried over anhydrous magnesium sulfate. Evaporation of the solvent gave a residue whose NMR spectrum showed it to be a 1:2 mixture of 2'R- and 2'S-methyl esters. This was chromatographed on alumina (Woelm; grade II), elution with 1:1 benzene-methylene chloride afforded 120 mg. of the 2'S-methyl ester in the first 10 ml. of eluate, followed by mixture of the 2'R and 2'S esters. The first eluate was crystallized from methylene chloride-petroleum ether to give 55 mg. (7%) of pure 2'S ester.

In a second experiment the chlorination was performed for 3 min., as already described and the solution allowed to stand at room temperature for 3 hr. Evaporation then afforded a mixture containing 68% of 2-(2'S-chloro-3'S -phthalimido-4'-oxo)azetidinyl-3-methyl-2-butenoyl chloride and 32% of the 2'R epimer, i.e., under these conditions the cis:trans ratio was revised in favor of the trans isomer. The same 68:32 ratio was obtained if chlorination was performed for 30 seconds and the solution immediately evaporated to dryness.

When chlorination was performed for 10 seconds with a slow stream of chlorine, and the mixture then immediately evaporated to dryness, a single new compound was obtained. The NMR spectrum of this new compound showed peaks at $(CDCl_3)$ 2.1 (4H,d), 4.01 (2H,s), 7.60 (3H), 7.64 (3H). In $CD_3COCD_3$ the two-proton singlet at 4.01 showed slight splitting to a doublet. The compound is assigned the structure

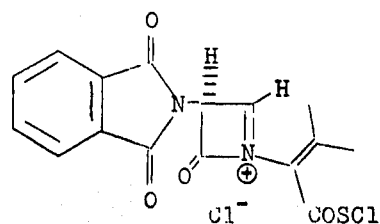

That it is an intermediate in the chlorination of the anhydropenicillin was shown by its conversion, upon further chlorination to the 2'R and 2'S dichlorides, Equilibration of methyl 2-(2'R-chloro-3'S-phthalimido-4'-oxo)-azetidinyl-3-methyl-2-butenoate and its 2'S epimer A. Starting with the 2'R isomer The pure 2'R ester (100 mg., 0.28 mmole) was added to a warm solution of tetraethylammonium chloride (95.2 mg., 0.57 mmole; two molar equivalents) in acetone (15 ml.). The solution was refluxed for 2 hours, and then cooled to room temperature and poured onto a mixture of water and ice. Extraction with methylene chloride, followed by washing of the extract with water, drying over anhydrous magnesium sulfate and evaporation afforded a crystalline residue. The NMR spectrum of this residue was identical to that of the starting material except for the appearance of a weak doublet at τ 4.4 (J=2 Hz). The substance was therefore redissoled in acetone containing tetraethylammonium chloride (95.2 mg.), and refluxing was continued for an additional 14 hours. Isolation in the same manner as described above afforded a residue whose NMR spectrum showed it to be a 1:1 mixture of 2'R and 2'S esters.

The experiment was repeated with 100 mg. (.28 mmole) of the pure 2'R ester and 238 mg. (5 molar equivalents) of tetraethylammonium chloride in methyl ethyl ketone (10 ml.). After 4 hours of refluxing the product was isolated and found to be a 3:2 mixture of 2'R and 2'S esters. This ratio did not change when the material was refluxed for a further 8.5 hours in methyl ethyl ketone containing 5 molar equivalents of tetraethylammonium chloride.

The experiment was repeated with 100 mg. of the pure 2'R ester in acetone (15 ml.) containing 5 molar equivalents of tetraethylammonium chloride. After 12 hours and after 24 hours refluxing a 3:2 2'S:2'R ratio of esters was observed. The product of a 12 hour reaction was chromatographed on alumina (Woelm, grade II). Elution with benzene-methylene chloride (1:1), as already described, afforded 40 mg. of the 2'S compound in the first 25 ml. followed by 34 mg. of the 2'S compound in the next 45 ml. of eluate.

After 6 hours in refluxing chloroform (30 ml.) containing 5 molar equivalents of tetraethylammonium chloride, the 2'R ester (430 mg.) was converted into a 2:1 2'R:2'S mixture.

B. Starting with the 2'S isomer

The 2'S ester (40 mg.) was refluxed for 12 hours in a mixture of acetone (10 ml.) and methylene chloride (5 ml.) containing 2 molar equivalents of tetraethylammonium chloride. The product was a 1:2 2'R:2'S mixture.

Chlorination of Anhydro-6-Phthalimidopenicillin in the Presence of Tetraethylammonium Chloride A solution of anhydro-6-phthalimidopenicillin (100 mg., 0.30 mmole) in methylene chloride (5 ml.) containing tetraethylammonium chloride (252 mg. 5 molar equivalents) was chlorinated in the usual manner. Evaporation of the solvent then gave a residue which consisted of a 3:2 mixture of 2'S:2'R dichlorides.

The experiment was repeated using 10 ml. of methylene chloride for the reaction. After removal of the solvent, absolute methanol (5 ml.) and methylene chloride (5 ml.) were added and the mixture was stirred for 30 min. Then it was washed with ice-cold sodium bicarbonate solution and water, dried over magnesium sulfate, and evaporated. The residue (132 mg.) was a 1:1 mixture of methyl esters.

Thus chlorination of the anhydropenicillin in the presence of added chloride ions causes a slight improvement in the 2'S:2'R ratio.

Attempted Reaction of 2-(2'R-chloro-3'S-phthalimido-4'-oxo)azetidinyl-3-methyl-2-butenoic acid with sodium azide The 2'R acid (50 mg., 0.14 mmole) was added to a solution of sodium azide (10 mg., 0.15 mmole) in water (10 ml.). Complete dissolution was achieved upon addition of a few drops of 5% bicarbonate solution. The solution was heated on the steam bath for 4 hours, by which time it was dark orange in color. After cooling, the solution was brought to pH 4 with N HCl and extracted with methylene chloride. The extract was washed with water, dried over anhydrous magnesium sulfate and evaporated to yield 24 mg. of material. The IR spectrum of this material showed no β-lactam absorption at 5.6μ.

In a second experiment, a solution of sodium azide (20.5 mg., 0.33 mmole) in dimethylformamide (30 ml.) was prepared by brief warming on the steam bath, and the 2'R acid (100 mg., 0.29 mmole) was added. The resulting solution was heated on the steam bath for 19 hours, then cooled, diluted with water, brought to pH 4 with N HCl and extracted with methylene chloride. After washing with water and drying over anhydrous magnesium sulfate the methylene chloride was evaporated to a residue of 47 mg. A small amount of crystalline material was obtained upon treatment of this residue with methylene chloride-petroleum ether. The IR spectrum of this material showed no azide peak at 4.7μ and only phthalimido absorption at 5.62μ. Evaporation of the mother liquor gave a residue whose IR spectrum showed a weak azide peak at 4.72μ and some β-lactam absorption at 5.60μ.

Conversion of methyl 2-(2'R-chloro-3'S-phthalimido-4'-oxo)-azetidinyl-3-methyl-2-butenoate into methyl 2-(2'S-azido-3'S-phthalimido-4'-oxo)azetidinyl-3-methyl-2-butenoate Sodium azide (10.1 mg., 0.16 mmole) was dissolved in DMF (15 ml.) by brief warming on the steam bath, and to this solution was added the methyl ester having the 2'R-chloro configuration (50 mg., 0.14 mmole). The resulting solution was stirred at room temperature for 24 hours and then diluted with water and extracted with methylene chloride. The methylene chloride extract was washed thoroughly with water, dried over anhydrous magnesium sulfate and evaporated to dryness. The resulting white crystalline solid was recrystallized from chloroform-petroleum ether to give 42 mg. of unreacted 2'R ester.

In a second experiment the reaction mixture was heated on the steam bath for 5 hours, by which time the color had become a deep yellowish-orange. Isolation of the product as described above afforded 38 mg. of a solid residue whose IR spectrum showed azide absorption at 4.7μ and carbonyl peaks at 5.58, 5.62, 5.79 and 5.82μ. The NMR spectrum showed, in the β-lactam region, 1-proton absorptions at 4.22 and 4.71 (d, J-2.0).

In a third experiment, sodium azide (20.2 mg., 0.31 mmole) was dissolved in 10 ml. of freshly distilled DMF, the 2'R ester (100 mg., 0.28 mmole) was added, and the solution was heated 5 hours on the steam bath. The product was isolated in the usual manner and was crystallized from 2-butanone-ethanol to give 25 mg. of 2'S-azido ester (first crop), m.p. 142°–144°.

Anal. Calcd. for $C_{17}H_{15}N_5O_5$: C, 55,29; H, 4.09; N, 18.97 Found: C, 55,45; H, 4.02; N, 18.68.

The NMR spectrum shows peaks at 2.22 (4H,d), 4.22 (1H,d,J=2.0 Hz), 4.71 (1H,d,J=2.0 Hz), 6.17 (3H), 7.70 (3H), 7.91 (3H).

The structure of the compound is

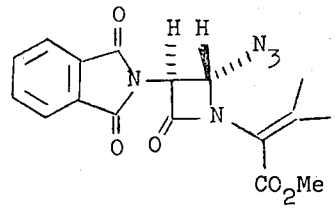

In a further experiment sodium azide (20.2 mg., 0.28 mmole) was dissolved in freshly distilled DMF (10 ml.) by heating on the steam bath for 0.5 hours. Then the 2'R-chloro ester (100 mg., 0.28 mmole) was added, followed by an additional 20.2 mg. of sodium azide. The resulting mixture was heated at 90° for 3 hours, with stirring. Isolation as described above yielded a semi-solid residue which weighed 68.2 mg. (67%) and whose NMR spectrum was identical to that described above. Chromatography on a 1×2 column of alumina (Woelm, grade II) and elution with methylene chloride afforded 62 mg. of crystalline material. Recrystallization from methylene chloride-petroleum ether afforded 38 mg. in the first crop, m.p. 144°–145° (colorless prisms).

Conversion of methyl 2-(2′S-chloro-3′S-phthalimido-4′-oxo)-azetidinyl-3-methyl-2-butenoate into methyl 2-(2′R-azido-3′S-phthalimido-4′-oxo)azetidinyl-3-methyl-2-butenoate The pure 2′S-chloro ester (100 mg., 0.28 mmole) was reacted with sodium azide (2 molar equivalents) in DMF (10 ml.) as in the last experiment described above. Isolation in the same manner afforded 52.2 mg. of material. This material was chromatographed on a 4.5 × 1 cm column of alumina (Woelm, activity II). Elution with methylene chloride afforded no material in the first 10 ml. followed by 13.0 and 11.1 mg. of crystalline material in each of the next 10 ml. Both residues had the same NMR spectrum. They were therefore combined and recrystallized from chloroform-petroleum ether to give 19 mg. of colorless needles, m.p. 183°–187° dec.

The NMR spectrum shows peaks at 2.10 (4H,d), 4.18 (1H,d,4.0 Hz), 4.33 (1H,d,4.0 Hz), 6.10 (3H), 7.47 (6H).

Anal. Calcd. for $C_{17}H_{15}N_5O_5$: C, 55.29; H, 4.09; N, 18.97 Found: C, 55.06; H, 4.25; N, 19.10.

The structure of this compound is

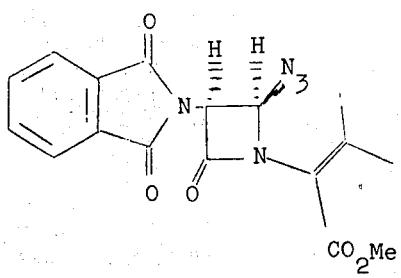

Chlorination of the p-toluenesulfonic acid salt of anhydro-6-aminopenicillin The salt (328 mg., 0.89 mmole) was suspended in methylene chloride (30 ml.), the mixture cooled to 0°, and gaseous chlorine was introduced for 15 seconds. Dry nitrogen was then passed into the resulting yellow solution for 15 minutes to remove excess chlorine, and the solution was evaporated to dryness. Trituration of the residue with dry ether afforded a quantitative yield of the mixture of two compounds shown below:

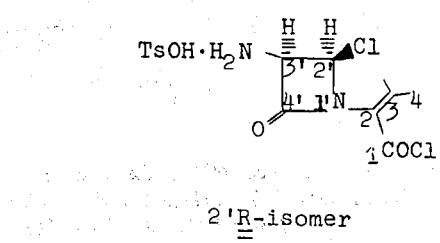

2′R-isomer

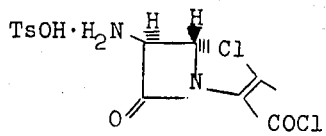

2′S-isomer

The mixture was a stable (below 20°) white powder, m.p. 148°–149° dec. The IR spectrum showed peaks at 5.55 and 5.62 μ. The 2′R-isomer (formed in 80% yield) showed NMR absorption CDCl₃) at τ 2.20 (2H,d), 2.80 (2H,d) 4.02 (1H,d,4.2Hz), 4.82 (1H,d,4.2 Hz), 7.63 (3H), 7.80 (3H), 8.00 (3H). (The NH₂ protons were not observed.) The 2′S-isomer (formed in 20% yield) showed NMR absorption at 2.20 (2H,d), 2.80 (2H,d), 4.82 (2H,m), 7.63 (3H), 7.83 (3H), 8.00 (3H).

Chlorination of anhydro-6-tritylamino penicillin, the precursor of the p-toluenesulfonic acid salt, was unsuccessful using Cl₂, SO₂Cl₂, pyrrolidone hydrotrichloride, pyridinium trichloride, PCl₅, and (C₆H₅O)₃PCl. In each case a reaction of the desired type occurred, but the trityl group was then lost and the product decomposed.

Chlorination of the p-toluenesulfonic acid salt in the presence of excess tetraethylammonium chloride did not alter the ratio of the 2′R and 2′S isomers.

Reaction of the chlorination product of the p-toluenesulfonic acid salt of anhydro-6-aminopenicillin with methanol The anhydropenicillin salt (3.80 g., 10.3 mmoles) was suspended in methylene chloride (150 ml.), the mixture was cooled to −5°, and a slow stream of dry nitrogen was passed through it. Gaseous chlorine was passed into the mixture for 30 seconds, and the nitrogen stream was then continued for 15 min. Methanol (75 ml.) was added and the resulting yellow solution was swept with nitrogen at 0° for 20 min. The cooling bath was then removed and, after 15 min., the solvent was removed under reduced pressure at 25°. The residue was treated with 5 ml. of methylene chloride and the resulting solution re-evaporated; this procedure was repeated three times and at this point the pale yellow foam had no odor of chlorine or HCl. The foam was dissolved in dry acetone, the orange solution was filtered to remove a small amount of insoluble material, and petroleum ether (30°–60°) was added to the cloud point. A few drops of acetone were then added to clarify the solution, and crystallization was allowed to proceed at 10° C. The white crystals thus obtained were washed with cold 1:1 acetone-petroleum ether, and dried in vacuo. The yield was 2.7 g. (67%), m.p. 125°–130° dec. The compound has the structure shown

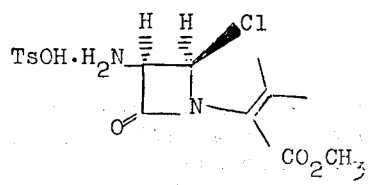

Anal. Calcd. for $C_{16}H_{21}N_2O_6Cl$: C, 47.48; H, 5.23. Found: C, 47.62; H, 5.54.

The NMR spectrum shows peaks at 2.22 (2H,d), 2.90 (2H,d), 4.02 (1H,d,4.0 Hz), 4.87 (1H,d,4.0 Hz), 6.48 (3H), 7.65 (3H), 7.78 (3H), 8.15 (3H).

ester of 2-(2'R-chloro-3'S-phthalimido-4'-oxo)azetidinyl-3-methyl-2-butenoic acid, identical in all respects with the compound obtained from anhydro-6-phthalimidopenicillin.

The reaction sequence just described is:

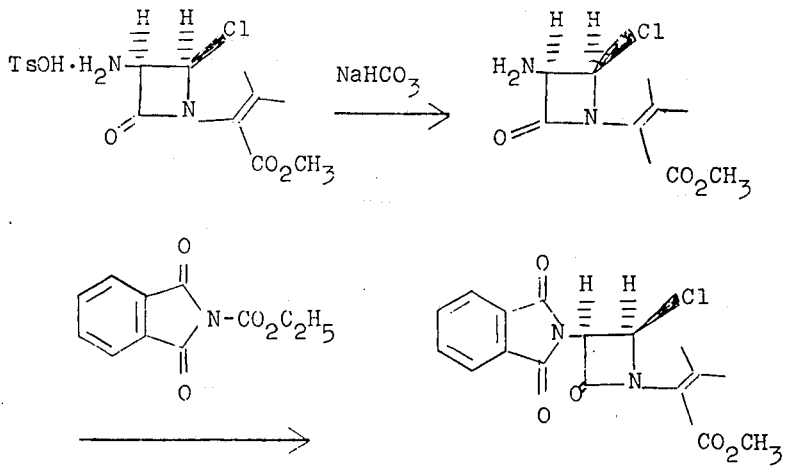

Interconversion of the methyl esters of the 2'R-chloro-3'S-aminotosylate and 2'R-chloro-3'S-phthalimido series.

The crude methyl ester obtained by chlorination of 193 mg. (0.48 mmole) of the p-toluenesulfonic acid salt of anhydro-6-aminopenicillin, and then treatment with methanol, was dissolved in methylene chloride. The solution was cooked to 0° C and shaken with an ice-cold 5% sodium bicarbonate solution. The colorless organic layer was dried over anhydrous magnesium sulfate, the volume reduced to 5 ml., and N-carboethoxyphthalimide )100 mg., 0.46 mmole) was added. The reaction mixture was allowed to stand overnight at room temperature and the solvent was then removed.

Hydrolysis of the chlorination product of the p-toluenesulfonic acid salt of anhydro-6-aminopenicillin The salt (200 mg.) was chlorinated in the usual way and, after removal of the solvent, the residue was maintained under high vacuum for 30 min. It was then dissolved in a mixture of $D_2O$ (2 ml.) and $CD_3COCD_3$ (2 ml.), cooled to 0°, and the NMR spectrum was recorded at intervals. Hydrolysis was complete after 3 hr., and the solvent was, therefore, removed by lyophilization. The resulting foam was redissolved in $D_2O$. The NMR spectrum of this solution indicated that quantitative conversion to a 4:1 mixture of 2'R:2'S chloro acids had been achieved.

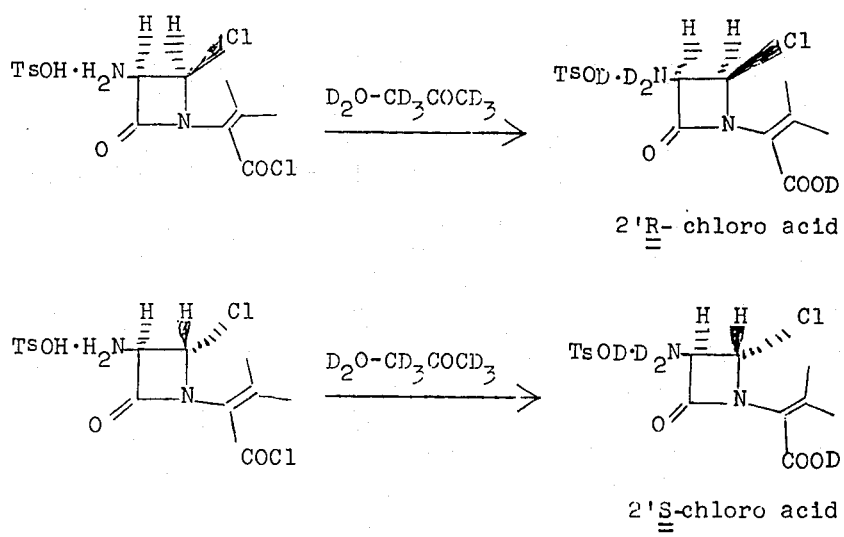

The residue was chromatographed on a column of Woelm alumina (neutral, grade II). Elution with 1:1 benzene-methylene chloride afforded 37 mg. of undefined material followed by 68 mg. (after recrystallization from chloroform-petroleum ether) of the methyl The 2'R-chloro acid showed NMR absorptions at 2.37 (2H,d), 2.78 (2H,d), 3.78 (1H,d,4.0 Hz), 4.93 (1H,d,4.0 Hz), 7.77 (3H), 7.88 (3H), 8.09 (3H). The epimeric 2'S-chloro acid had NMR absorption at 2.37 (2H,d), 2.78 (2H,d), 4.53 (1H,d,2.0 Hz), 4.57

(1H,d,2.0 Hz), 7.77 (3H), 7.98 (3H), 8.24 (3H).

Methyl ester of the 2-(2'R-chloro-3'S-amino-4'-oxo)azetidinyl-3-methyl-2-butenoic acid.

The methyl ester of the 2'R-chloro-3'S-aminotosylate was neutralized with bicarbonate, as already described. Evaporation of the methylene chloride solution gave the free base, a crystalline compound, m.p. 67°–70° dec. The compound was not stable in the solid state and darkened perceptibly after 10 minutes at room temperature.

The NMR spectrum of the compound has peaks at 3.97 (1H,d, 4.1 Hz), 5.38 (1H,d,4.1 Hz), 6.22 (3H), 7.70 (3H), 8.00 (3H). The position of the NH₂ protons varies with time; although these peaks shift, no other changes occur in the spectrum. The IR spectrum of the compound has peaks at 2.94, 5.60, 5.80, 6.12μ which (in CH₂Cl₂) do not change with time.

The structure of this compound is

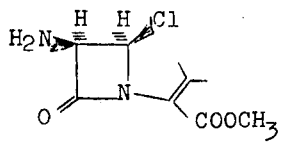

Methyl ester of 2-(2'S-chloro-3'-S-amino-4'-oxo)azetidinyl-3-methyl-2-butenoic acid epimerization of the 2'R-compound.

The 2'R-chloro-3'S-aminotosylate (440 mg., 1.09 mmole) and tetramethylguanidinium chloride (1.387 g., 9.1 mmoles, 9 molar equivalents) were refluxed in spectroscopic grade chloroform (9 ml.) for 4.5 hours. The solution was then cooled to 0°, washed with ice-cold 5% bicarbonate solution, dried over anhydros magnesium sulfate, and evaporated to dryness under reduced pressure at 25°. The NMR spectrum of the residue indicated it to be a 5:1 mixture of the 2'S- and 2'R-epimers, the predominant isomer being the 2'S compound, whose structure is:

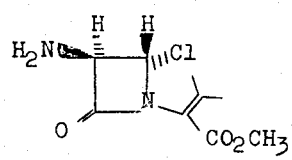

The NMR spectrum of this compound shows peaks at 4.45 (1H,d,1.8 Hz), 5.63 (1H,d,1.8 Hz), 6.18 (3H), 7.70 (3H), 8.00 (3H). The position of the NH₂ protons depends upon the age of the solution.

Complete separation of the two epimers could be achieved by alumina chromatography and elution with 1:1 benzene-ethyl acetate. However, because of the instability of these compounds it was usually more convenient to separate at a later stage.

Conversion of the p-toluenesulfonic acid salt of methyl 2-(2'R-chloro-3'S-amino-4'-oxo)azetidinyl-3-methyl-2-butenoate to the 2'S-amino ester The crystalline methyl ester having the 2'R-chloro-3'S-TsOH.H₂N-configuration (448 mg., 1.1 mmoles) and tetramethylguanidinium azide (347 mg., 2.2 mmoles, 2 molar equivalents) were refluxed for 75 minutes in 20 ml. of anhydrous chloroform. The solution was allowed to cool and excess anhydrous ether was added to precipitate tetramethylguanidinium chloride, which was removed by filtration. The resulting material, after removal of the solvent, was the desired 2'S-azido-3'S-amino ester (237 mg., 90%) which appeared pure by t.l.c. and NMR. The NMR spectrum had peaks at 4.97 (1H,d, 1.8 Hz), 5.87 (1H,d,1.8 Hz), 6.20 (3H), 7.00 (2H), 7.72 (3H), 8.02 (3H).

The compound has the structure

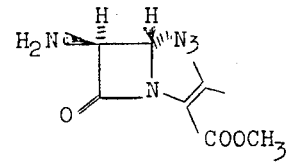

The compound could also be isolated by washing the chloroform reaction mixture with cold water, drying and evaporating. Tetraethylammonium azide (in various solvents) and sodium azide (in DMF) were less effective for this reaction.

Conversion of the p-toluenesulfonic acid salt of methyl 2-(2'S-chloro-3'S-amino-4'-oxo)azetidinyl-3-methyl-2-butenoate to the 2'R-azido-3'S-amino methyl ester A 4:1 mixture of 2'S- and 2'R-chloro-3'S-amino esters from an epimerization of the 2'R-chloro compound (532 mg., 2.29 mmoles), and tetramethylguanidinium azide (500 mg., 3.2 mmoles) were refluxed in pure chloroform (10 ml.) for 4.5 hours. The mixture was then washed with ice-cold 5% bicarbonate solution, dried over anhydrous magnesium sulfate, and evaporated to give 465 mg. (85%) of a 3.3:1 mixture of 2'R- /and 2'S-azido-3'S-amino methyl esters. This mixture was separated by chromatography on neutral alumina (Woelm, activity II). Elution with benzene:ethyl acetate (2:3) afforded the pure 2'R-azido-3'S-amino ester as a crystalline compound. Recrystallization from chloroform-petroleum ether gave long needles, m.p. 116°–117°.

Anal. calc'd. for C₉H₁₃N₅O₃: C, 45.19; H, 5.48; N, 29.28. Found: C, 45.42; H, 5.24; N, 28.81.

The IR spectrum has peaks at 4.72, 5.62 and 5.80μ. The NMR spectrum shows peaks at 3.97 (1H,d,4.1 Hz), 4.38 (d,4.1 Hz), 6.22 (3H), 7.60 (2H), 7.70 (3H), 8.00 (3H).

The compound has the structure

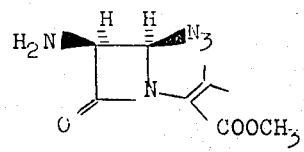

Separation of the 2'S- and 2'R-azido-3'S-amino methyl esters via the p-toluenesulfonic acid salts.

A 1:1 mixture of the 2'S- and 2'R-azido compounds (239 mg.) was dissolved in dry acetone (3 ml.) and the solution was treated with an equivalent amount of p-toluenesulfonic acid hydrate. Crystallization began after 5 min. After 15 hr., acetone (1 ml.) was added and, after an additional 20 min., ether (5 ml.). Filtration then gave 150 mg. (72% recovery, based on one isomer) of a crystalline p-toluenesulfonic acid salt. Regeneration of the free base (NaHCO₃-H₂O-CH₂Cl₂) revealed that this was the salt of the 2'S-azido compound. The separation procedure is thus

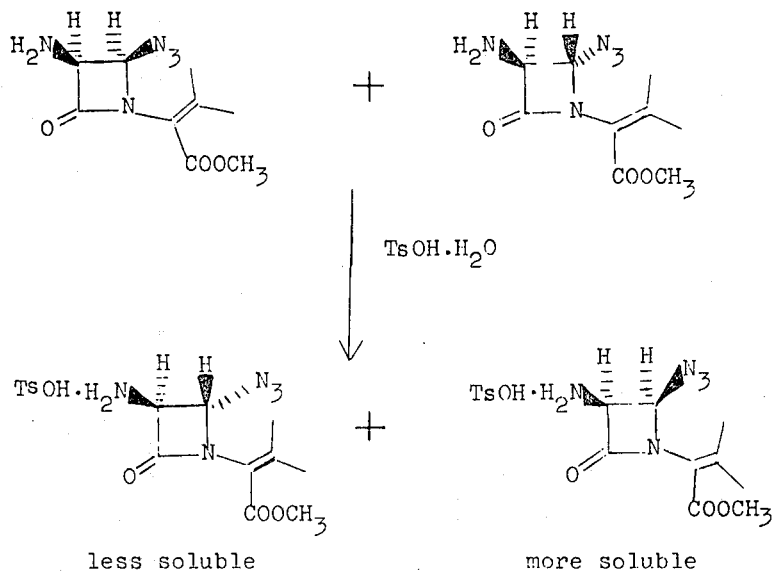

less soluble                more soluble

Phenylacetylation of Methyl 2-(2'R-chloro-3'S-amino-4'-oxo)-azetidinyl-3-methyl-2-butenoate The free 2'R-chloro-3'S-amino ester, obtained from 722 mg. (1.78 mmoles) of the p-toluenesulfonic acid salt, was dissolved in methylene chloride (15 ml.), and phenylacetic acid (242 mg., 1.78 mmoles) was added. This solution was treated, dropwise with stirring, with a solution of dicyclohexylcarbodiimide (405 mg., 1.96 mmoles). Precipitation of dicyclohexylurea commenced before the addition was complete. The reaction mixture was allowed to stand at room temperature for three hours, by which time no free amine remained (by t.l.c.). Most of the urea was then removed by filtration, and the filtrate was washed with ice-cold 5% bicarbonate solution. After drying over anhydrous magnesium sulfate, the organic phase was evaporated to give a solid residue. This was dissolved in boiling chloroform and an equal volume of petroleum ether (30°–60°) was added, whereupon crystallization occurred. The crude product weighed 700 mg. One more recrystallization from the same solvent mixture gave 500 mg. (80%) of methyl 2-(2'R-chloro-3'S-phenylacetamido-4'-oxo)azetidinyl-3 -methyl-2-butenoate, m.p. 111°–115° dec. The NMR spectrum of this compound shows peaks at 2.62 (5H), 3.10 (1H,d,10 Hz), 3.94 (1H,d,4.2 Hz), 4.34 (1H,q,4.2,10 Hz), 6.22 (3H), 6.31 (2H), 7.70 (3H), 8.02 (3H). The same compound could be obtained, but in slightly lower yield using diisopropylcarbodiimide or phenylacetyl chloride and triethylamine. The compound has the structure

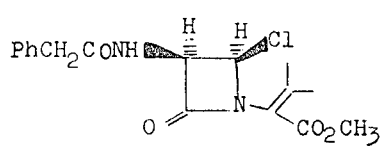

Phenylacetylation of Methyl 2-(2'S-chloro-3'S-amino-4'-oxo)-azetidinyl-3-methyl-2-butenoate Cyclization to Oxazoline The p-toluenesulfonic acid salt of methyl 2-(2'R-chloro-3'S-amino-4'-oxo)azetidinyl-3-methyl-2-butenoate (651 mg., 1.6 mmoles) and tetramethylguanidinium chloride (1.210 g., 5 molar equivalents) were refluxed in spectroscopic grade chloroform (9 ml.) for 4.5 hours. The resulting solution was cooled, washed successively with ice-cold 5% bicarbonate, ice-cold saturated sodium chloride, dried over anhydrous magnesium sulfate, and then used immediately for the next step (previous experiments had indicated that the above procedure leads to a 5:1 or 6:1 excess of the 2'S-chloro-3'S-amino compound over the 2'R-chloro-3'S-amino compound). To the solution were added phenylacetic acid (228 mg., 1.7 mmoles), diisopropylcarbodiimide (222 mg., 1.8 mmoles) and methylene chloride (20 ml.), and this solution was refluxed for 1 hour. Removal of the solvent gave a residue whose NMR spectrum showed peaks at 2.73 (phenyl), 4.72 (d, 1.9 Hz), 5.33 (d,1.9Hz), 6.30 (OCH$_3$), 6.47 (CH$_2$), 7.80 (CH$_3$), 8.05 (CH$_3$). The structure of this compound is

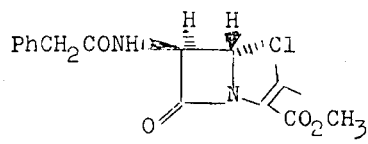

The spectrum also showed peaks at 4.02 (d,3.8 Hz), 4.80 (d, 3.8 Hz), 6.33, 7.83, 8.43. This is the spectrum of the compound having the structure,

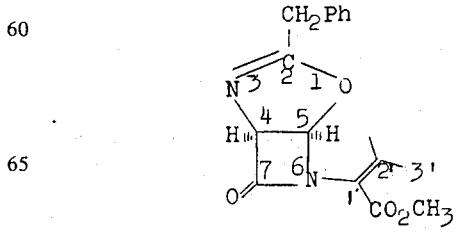

i.e., 2-benzyl-6-(1'-methoxycarbonyl-2'-methylprop-1'-enyl)-1-oxa-3,6-diaza-4S,5R-bicyclo[3,2,0]hept-2-en-7-one, which is formed by intramolecular cyclization of the preceeding compound. The cyclization occurs on standing, but is facilitated by heating of a solution of the chloro compound, by shaking with bicarbonate, or by chromatography on alumina or silica gel of either epimeric 2'-chloro-3'-acylamino ester, as will be described below.

Chromatography of the above mixture on silica gel and elution with petroleum ether - ethyl acetate (1:1) afforded the oxazoline. Recrystallization from ethyl acetate gave 240 mg. (49% from the p-toluenesulfonic acid salt), m.p. 126.5°–127°.

The NMR spectrum of the pure compound shows peaks at 2.73 (5H), 4.02 (1H,d,3.8 Hz), 4.80 (1H,d,3.8 Hz), 6.30 (3H), 6.33 (2H), 7.83 (3H), 8.43 (3H).

Formation of the oxazoline upon chromatography of the cis-2'R-chloro-2'S-phenylacetamido methyl ester The crystalline cis compound (100 mg.) was chromatographed on alumina (Woelm, grade II). Elution with carbon tetrachloridebenzene (1:1) gave 38 mg. of the oxazoline in the first fractions, followed by uncyclized cis compound.

In a second experiment, the cis compound (1.0 g.) was chromatographed on 37 g. of silica gel, elution being performed with 1:1 petroleum ether (30°–60°): ethyl acetate. There were obtained in successive fractions 450 mg. of recovered cis compound, 140 mg. of a mixture of the cis compound and oxazoline, and 210 mg. of oxazoline. The transformation is

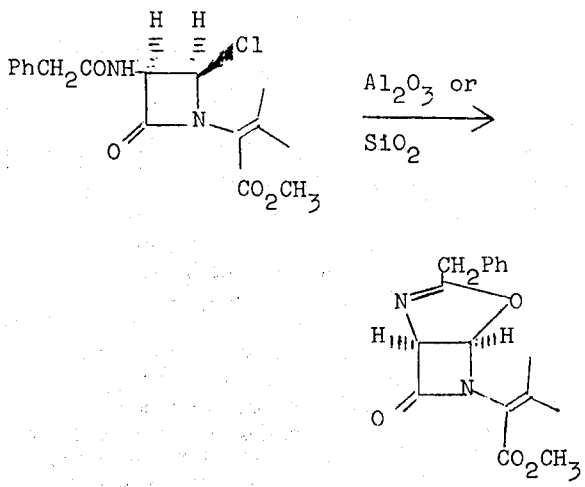

In a third experiment the crystalline 2'R-chloro-3',S-amino methyl ester (157 mg., 0.68 mmole), in dry methylene chloride (8 ml.), was treated successively with phenylacetic acid (92 mg., 0.68 mmole) and diisopropylcarbodiimide (93 mg., 0.74 mmole). The solution was stirred at room temperature for 22 hours, and the precipitated diisopropylurea was then collected by filtration. Addition of ether to the mother liquor completed the precipitation of the urea. Evaporation of the filtrate, followed by chromatography on a 1.0×7 cm column of alumina (activity II) gave, with 1:1 benzene-methylene chloride, 83 mg. of crystalline material. This was found, by NMR and t.l.c. to be a mixture of oxazoline and 2'R-chloro-3'S-phenylacetamido ester.

Isolation of Methyl 2-(2'R-phenylacetoxy-3'S-phenylacetamido-4'-oxo)azetidinyl-3-methyl-2-butenoate and oxazoline following phenylacetylation of the epimeric methyl 2-(2'-chloro-3'S-amino-4'-oxo)azetidinyl-3-methyl-2-butenoates The p-toluenesulfonic acid salt of methyl 2-(2'R-chloro-3'S-amino-4'-oxo)azetidinyl-3-methyl-2-butenoate (4.428 g., 10.9 mmoles) and 8.260 g. (54.5 mmoles) of freshly prepared tetramethylguanidinium chloride were refluxed for 2 hours in spectroscopic grade chloroform (65 ml.). The cooled solution was washed successively with ice-cold 5% bicarbonate solution, ice-cold saturated sodium chloride solution, and then dried over anhydrous magnesium sulfate. Then a solution of phenylacetic acid (1.490 g., 11 mmoles) and diisopropylcarbodiimide (1.500 g., 11.9 mmoles) in methylene chloride (25 ml.) was added, and the mixture was refluxed for 2 hours. The NMR spectrum of the reaction product showed only a small amount of the oxazoline (based on the peaks at 7.83 and 8.43). The solution was then washed with ice-cold 5% bicarbonate, dried over anhydrous magnesium sulfate, and evaporated. The NMR spectrum of this residue now showed oxazoline as the major product. Thus, washing with bicarbonate had caused cyclization. The product was left at 10° overnight, then redissolved in methylene chloride and shaken again with bicarbonate solution. After drying and evaporation of the organic layer the NMR spectrum of the residue was redetermined; it now indicated that the mixture contained 70% of oxazoline. The mixture, in 1:1 ethyl acetate:petroleum ether, was filtered through 50 g. of silica gel and then chromatographed carefully on 110 g. of silica gel. Elution was performed with graded mixtures of petroleum ether and ethyl acetate (250 ml. of 20% ethyl acetate, followed by 200 ml. of 30% ethyl acetate, followed by 200 ml. of 30% ethyl acetate, followed by 200 ml. of 35% ethyl acetate, followed by 200 ml. of 45% ethyl acetate, followed by 50% ethyl acetate); 40 ml. fractions were collected. Fractions 1–3 afforded 100 mg. of methyl 2-(2'R-chloro-3'S-phenylacetamido-4'-oxo)azetidinyl-3-methyl-2-butenoate. Fractions 5–12 afforded 1.475 g. of oxazoline. Fractions 13–15 were rechromatographed and yielded, besides an additional 150 mg. of oxazoline (total 1.625 g., 48%), 240 mg. of a compound assigned the structure

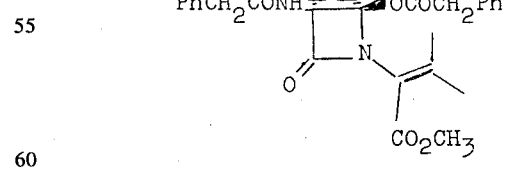

This compound has IR absorption at 2.9, 3.0, 5.60, 5.70, 5.80, 5.98, 6.05, 6.65$\mu$. The NMR spectrum has peaks at 2.65–2.75 (10H,m), 3.26 (1H,d,9.5 Hz), 3.68 (1H,d,4.1 Hz), 4.53 (q,4.1,9.5 Hz), 6.27 (3H), 6.43 (2H), 6.54 (2H), 7.82 (3H), 8.28 (3H). The mass spectrum shows a molecular ion at m/e 450.

Phenylacetylation of methyl 2-(2'R-azido-3'S-amino-4'-oxo)azetidinyl-3-methyl-2-butenoate The crystalline amino azide (415 mg., 1.74 mmole) was dissolved in dry methylene chloride (10 ml.) and to this solution were added, successively, phenylacetic acid (235 mg., 1.73 mmole) and diisopropylcarbodiimide (220 mg., 1.75 mmole). The solution was refluxed for 9 hours, and the solvent was then removed. The residue was triturated with cold carbon tetrachloride, and the carbon tetrachloride-soluble material (now free of most of the diisopropylurea) was chromatographed on alumina (Woelm, grade II). Flution with benzene-ethyl acetate afforded 641 mg. of pale yellow oil. This was rechromatographed to yield 601 mg. (97%) of methyl 2-(2'R-azido-3'S-phenylacetamido-4'-oxo)azetidinyl-3-methyl-2-butenoate as long needles, after recrystallization from carbon tetrachloride-petroleum ether; m.p. 102°–103°. The compound has the structure

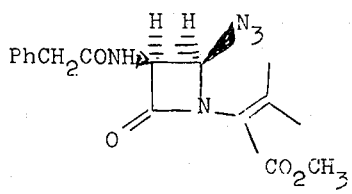

Anal. Calcd. for $C_{17}H_{19}N_5O_4$: C, 57.13; H, 5,36; N, 19.60. Found: C, 56.76; H, 5.35; N, 19.42.

The NMR spectrum shows peaks at 2.72 (5H), 3.38 (1H,br), 4.57 (1H,d,4.2 Hz), 4.72 (1H,d,4.2 Hz), 6.27 (3H), 6.38 (2H), 7.77 (3H), 8.05 (3H).

Phenylacetylation of methyl 2-(2'S-azido-3'S-amino-4'-oxo)azetidinyl-3-methyl-2-butenoate The amino azide (323 mg., 1.35 mmole) was dissolved in methylene chloride (10 ml.) containing triethylamine (110 mg., 1.09 mmole), and phenylacetyl chloride (170 mg., 1.1 mmole), in methylene chloride (5 ml.), was added dropwise with stirring. After 30 min., the reaction mixture was washed with five 10 ml. portions of water, dried over anhydrous magnesium sulfate, and evaporated. Chromatography on alumina (Woelm, activity II) and elution with benzene afforded 185 mg. of methyl 2-(2'S-azido-3'S-phenylacetamido-4'-oxo)azetidinyl-3-methyl-2-butenoate as a colorless oil. The compound has the structure:

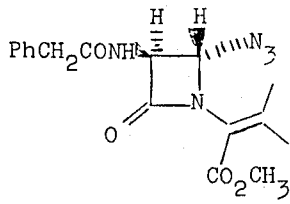

The NMR spectrum has peaks at 2.67 (5H), 3.22 (1H,d,8 Hz), 4.73 (1H,d,2.0 Hz), 5.32 (1H,q,2.0,8 Hz), 6.25 (3H), 6.38 (2H), 7.73 (3H), 8.00 (3H).

The same compond was obtained in 83% yield using phenylacetic acid and diisopropylcarbodiimide in methylene chloride. Conversion of Methyl 2-(2'R-chloro-3'S-phenylacetamido-4'oxo)azetidinyl-3-methyl-2-butenoate into methyl 2-(2'S-azido-3'S-phenylacetamido-4'-oxo)azetidinyl-3-methyl-2-butenoate Tetramethylguanidinium azide (126 mg., 0.8 mmole), in spectroscopic grade chloroform (3 ml.), was treated dropwise with stirring with a solution of the chloride (229 mg., 0.66 mmole) in chloroform (5 ml.). When the addition was complete, the reaction mixture was refluxed for 2 hours. At this time no unreacted chloride remained. The reaction solution was washed with water, dried over anhydrous magnesium sulfate and evaporated. The residue was chromatographed on silica gel to obtain 75 mg. of the azide, identical with that described in the preceeding experiment.

The equation for this reaction is:

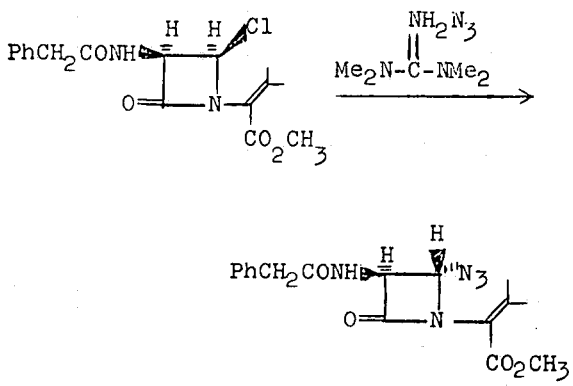

Preparation of t-butyl 2-(2'R-chloro-3'S-phthalimido-4'-oxo)azetidinyl-3-methyl-2-butenoate and t-butyl 2-(2'S-chloro-3'S-phthalimido-4'-oxo)azetidinyl-3-methyl-2-butenoate by reaction of the anhydro-6-phthalimidopenicillin chlorination product with t-butanol A 2:1 mixture of 2-(2'R-chloro-3'S-phthalimido-4'-oxo)azetidinyl-3-methyl-2-butenoyl chloride and its 2'S epimer was stirred overnight at room temperature in methylene chloride containing five molar equivalents of t-butanol. Evaporation of the solution then yielded a mixture containing only 15% of t-butyl esters (based on integration of the t-butoxy peak at 8.47 in the n.m.r. spectrum). The conversion increased to 40% when the mixed acid chlorides were refluxed overnight in methylene chloride-t-butanol. Refluxing for 20 hours in t-butanol solvent effected a 75% conversion to a mixture of t-butyl esters containing the same 2:1 ratio of epimers as the acid chloride precursor. Chromatography on silica gel separated these compounds. The cis-isomer was obtained as a colorless oil; its n.m.r. spectrum showed peaks at 2.15 (4H), 3.85 (1H, d, 4 Hg), 4.38 (1H, d, 4 Hg), 7.71 (6H), 8.46 (9H).

The compound has the structure

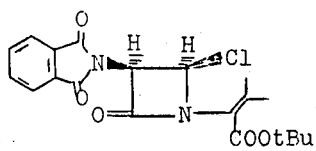

The trans-isomer crystallized on standing. Recrystallization from ethanol gave material melting at 170°–172°. The n.m.r. spectrum shows peaks at 2.29 (4H, d), 3.85 (1H, d, 2.0 Hg), 4.55 (1H, d, 2.0 Hg), 7.73 (3H), 1.98 (3H), 8.47 (9H).

Anal. Calcd. for $C_{20}H_{21}N_2O_5Cl$: C, 59.32; H, 5.23; N, 6.91. Found: C, 59.05; H, 5.36; N, 6.75.

This compound has the structure

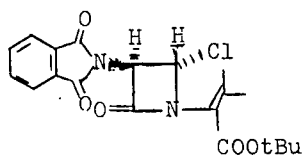

Reaction of t-butyl 2-(2'R-chloro-3'S-phthalimido-4'-oxo)azetidinyl-3-methyl-2-butenoate with trifluoroacetic acid.

The ester (100 mg.) was dissolved in trifluoroacetic acid (2ml.). After two minutes at room temperature the solvent was removed under reduced pressure. The residue was recrystallized from chloroform-petroleum ether to give 2-(2'R-chloro-3'S-phthalimido-4'-oxo)azetidinyl-3-methyl-2-butaneoic acid, identical in all respects to the compound prepared by direct hydrolysis of the dichloride.

Allylic Bromination of Methyl 2-(2'R-chloro-3'S-phthalimido-4'-oxo)azetidinyl-3-methyl-2-butenoate.

To a suspension of the methyl ester (100 mg., 0.276 mmole) in carbon tetrachloride (7.5 ml.) were added N-bromosuccinimide (108 mg., 0.61 mmole) and benzoyl peroxide (2 mg.). When this mixture was brought to reflux, the ester dissolved; the heat source was then replaced by a 100 watt Photoflood No. 2 lamp and reflector mounted close to the reaction flask and stirring was continued until the reaction was complete (10 min.). The resulting suspension was cooled, diluted with a small amount of chloroform, and the precipitated succinimide was removed by filtration. Evaporation of the filtrate gave a white crystalline solid residue whose n.m.r. spectrum showed no absorption in the region of the allylic methyl groups (7.5 to 8.0), but did show succinimide absorption at 7.2. This was removed, in part, by trituration with carbon tetrachloride and methylene chloride, and the total product was then chromatographed on neutral alumina (Woelm, activity II). Elution with methylene chloride afforded a crystalline dibromo compound which, after recrystallization from carbon tetrachloride-petroleum ether, melted at 65°–70° dec. and weighed 116 mg. (80%).

The compound has the structure

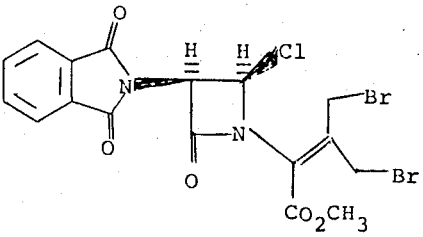

Anal. Calcd. for $C_{17}H_{13}N_2O_5ClBr_2$: C, 39.22; H, 2.52; N, 5.38. Found: C, 38.95; H, 2.36; N, 5.40.

The n.m.r. spectrum has peaks at 2.13 (4H), 3.80 (1H, d, 4.2 Hz), 4.21 (1H, d, 4.2 Hz), 5.07 (1H, d, 10.2 hz), 5.23 (1H, d, 10.9 Hz), 5.27 (1H, d, 10.2 Hz), 5.33 (1H, d, 10.9 Hz), 6.11 (3H). The spectrum appears unusually complex because one of the —CH₂Br groups is cis to the methoxycarbonyl substituent and the other is trans; and, in each -CH₂Br group, the methylene protons are magnetically non-equivalent. The i.r. spectrum has peaks at 5.55, 5.62 and 5.79 μ.

Allylic bromination of methyl 2-(2'S-chloro-3'S-phthalimido-4'-oxo)azetidinyl-3-methyl-2-butenoate The compound (100 mg.) was reacted with two molar-equivalents of N-bromosuccinimide in exactly the same manner as described above. Chromatography on alumina (Woelm, activity II) and elution with methylene chloride afforded 122 mg. (84%) of the desired compound as a clear viscous oil which appeared homogeneous by n.m.r. and t.l.c. The n.m.r. spectrum shows peaks at 2.08 (4H), 3.62 (1H, d, 1.7 Hz), 4.27 (1H, d, 1.7 Hz), 5.05 (1H, d, 10.0 Hz), 5.36 (1H, d, 10.0 Hz), 5.38 (1H, d, 11.0 Hz), 5.57 (1H, d, 11.0 Hz), 6.04 (3H).

This compound has the structure

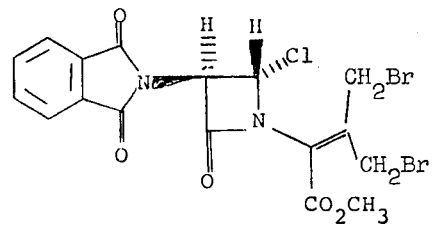

Allylic bromination of methyl 2-(2'R-azido-3'S-phenylacetamido-4'-oxo)azetidinyl-3-methyl-2-butenoate.

The methyl ester (136 mg., 0.38 mmole), N-bromosuccinimide (210 mg., 1.18 mmole, 3-molar-equivalents), and benzoyl peroxide (2 mg.) were heated to reflux in spectroscopic grade carbon tetrachloride; the heat source was then removed and replaced with a 100 watt Photoflood No. 2 lamp mounted close to the reaction vessel. The illumination/refluxing was terminated after 9 minutes. The resulting suspension was cooled, filtered, and the reddish filtrate washed with ice-cold 10% bicarbonate solution. The resulting yellow solution was dried over anhydrous magnesium sulfate and evaporated to give 143 mg. (77%) of viscous oil. Chromatography on alumina and elution with benzene, followed by chloroform afforded 29 mg. of material, having the same n.m.r. spectrum as the reaction product, which did not crystallize. Thie n.m.r. spectrum shows peaks at 2.67 (5H,m), 3.33 (1H, br), 4.32 (1H, d, 4.0 Hz), 4.50 (1H, d, 4.0 Hz), 5.38 (2H, sl.br.), 5.63 (2 H, sl.br.), 6.17 (3H), 6.18 (2H). The i.r. spectrum has peaks at 2.97, 4.71, 5.60, 5.75 and 5.95 μ. The spectra are those of a compound having the structure

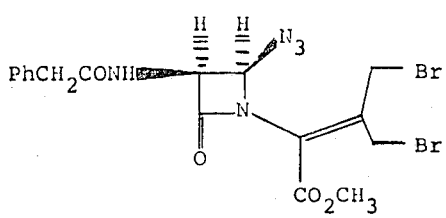

Reaction of methyl 2-(2'R-chloro-3'S-phthalimido-4'-oxo)-azetidinyl-3-methyl-2-butenoate with one molar equivalent of N-bromosuccinimide.

A suspension of the cis compound (75 mg., 0.207 mmole), N-bromosuccinimide (36.9 mg., 0.207 mmole) and benzoyl peroxide (1.5 mg.) in carbon tetrachloride (5 ml.) was heated to reflux until a clear solution resulted. The heat source was then removed and the mixture was stirred while being illuminated with a 100 watt Photoflood No. 2 amp. After 10 minutes the reaction was terminated and the mixture was cooled to room temperature and filtered to give succinimide (17 mg., 85% of the theoretical amount), identified by its melting point and infrared spectrum. The filtrate was evaporated to dryness to give a white solid residue which, on the basis of its NMR spectrum contained a small amount of succinimide and an exactly 1:1 mixture of the two possible monobrominated compounds. The solid was chromatographed on alumina to remove the succinimide. Flution with methylene chloride afforded the 1:1 mixture of monobrominated compounds as a white foam (87.5 mg., 96%). The NMR spectrum of this mixture shows peaks at 2.20 ( 4H), 3.83 (0.5H,d,4.2 Hz), 3.87 (0.5H,d,4.2 Hz), 4.28 (0.5H,d,4.2 Hz), 4.32 (0.5H,d,4.2 Hz), 5.10–5.88 (2H,m,overlapping AB quartets), 6.15 (1.5H), 6.17 (1.5H), 7.55 (3H). The structures of these compounds are

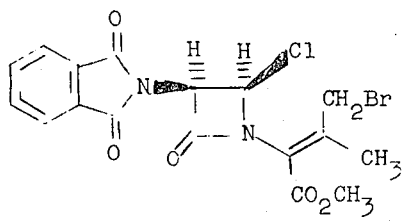

methyl 2-(2'R-chloro-3'S-phthalimido-4'-oxo)azetidinyl-3-methyl-4-bromo-trans-2-butanoate and

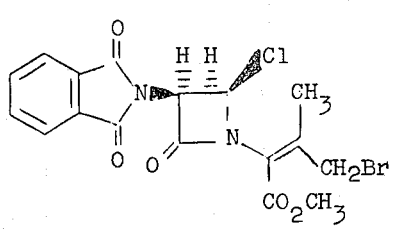

methyl 2-(2'R-chloro-3'S-phthalimido-4'-oxo)azetidinyl-3-methyl-4-bromo-cis-2-butenoate.

Conversion of the cis- and trans-methyl 2-(2'R-chloro-3'S-phthalimido-4'-oxo)azetidinyl-3-methyl-4-bromo-2-butenoates to the cis- and trans-methyl 2-(2'R-chloro-3'S-phthalimido-4'-oxo)azetidinyl-3-methyl-4-azido-2-butenoates.

The 1:1 mixture of monobrominated compounds (87.5 mg., 0.198 mmole), in spectroscopic grade chloroform (3 ml.), was treated with tetramethylguanidinium azide (34.4 mg., 0.218 mmole). A pale yellow color appeared immediately. The solution was stirred at room temperature for 3 hours (under these conditions the 2'-chloro substituent is stable) and was then a pale yellow-brown in color. It was diluted with chloroform, washed with water, decolorized with activated carbon and dried over anhydrous magnesium sulfate. Evaporation of the solvent afforded 83.9 mg. of a white solid residue. Examination of this residue by t.l.c. showed no unreacted monobrominated compounds. The IR spectrum had peaks at 4.70 (azide), 5.52 (β-lactam), 5.58 and 5.79μ (phthalimido), 5.75 (ester) and 6.16μ. The NMR spectrum showed that the azides had been obtained. It had peaks at 2.17 (4H), 3.78 (1H,d,4.0 Hz), 4.22 (1H,d,4.0 Hz), 5.12–5.87 (2H, overlapping AB quartets), 6.12 (3H), 7.58 (3H). The two isomers apparently have the same NMR spectrum. The structures of these compounds are

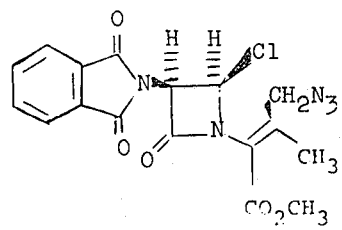

methyl 2-(2'R-chloro-3'S-phthalimido-4'-oxo)azetidinyl-3-methyl-4-azido-trans-2-butenoate and

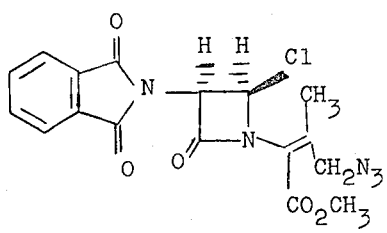

methyl 2-(2'R-chloro-3'S-phthalimido-4'-oxo)azetidinyl-3-methyl-4-azido-cis-2-butenoate.

Conversion of the cis- and trans- methyl 2-(2'R-chloro-3'S-phthalimido-4'-oxo)azetidinyl-3-methyl-4-azido-2-butenoates to the cis- and trans-methyl 2-(2'R-chloro-3'S-phthalimido-4'-oxo)azetidinyl-3-methyl-4-amino-2-butanoates The mixture of azides (83.9 mg.) in benzene (10 ml.), was hydrogenated over Adams catalyst (50 mg.) at 45 psi for 3 hours. The reaction solution was then diluted with chloroform and passed through a pad of anhydrous magnesium sulfate. Evaporation at 25° afforded a sticky solid residue. The IR spectrum showed a peak at 4.7 μ about half the intensity of one in the same position in the starting material. The NMR spectrum showed peaks due to the azide and, as well, some new peaks. Reduction was, therefore, incomplete. The hydrogenation was repeated for an additional 3 hours at 45 p.s.i. The resulting mixture was diluted with chloroform and passed through a pad of anhydrous magnesium sulfate. The black filtrate was not decolorized upon filtration through "Celite" or upon shaking (of an aliquot) with 5% sodium bicarbonate solution. Evaporation at room temperature afforded a black solid residue (92 mg.) whose IR spectrum showed complete disappearance of the azide absorption and whose NMR spectrum showed disappearance of the multiplets in the 5– 6τ region and appearance of new multiplets in the 7τ region. The solid was redissolved in chloroform, treated with activated carbon and passed through a pad of anhydrous magnesium sulfate to give a clear colorless solution. Evaporation gave 87 mg. of a solid residue. The NMR spectrum shows peaks at 2.18 (4H), 3.88 (1H,d,4.1 Hz), 4.33 (1H,d,4.1 Hz), 6.90–7.20 (2H,m), 6.20 (3H), 7.67 (1.5H), 7.70 (1.5H). The structures of the amino compounds are

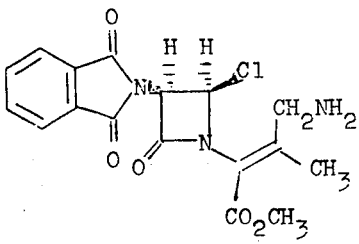

methyl 2-(2'R-chloro-3'S-phthalimido-4'-oxo)azetidinyl-3methyl-4-amino-trans-2-butanoate and

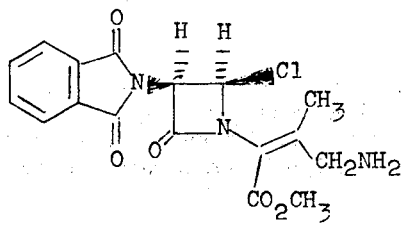

methyl 2-(2'R-chloro-3' S-phthalimido-4'-oxo)azetidinyl-3-methyl-4-amino-cis-2-butenoate.

Cyclization of methyl 2-(2'R-chloro-3'S-phthalimido-4'-oxo)azetidinyl-3-methyl-4-amino-trans-2-butenoate to 3-methyl-4-methoxycarbonyl-7S-phthalimido-1,5-diaza-6S-bicyclo [4,2,0] oct-3-en-8-one The above mixture of amines was recovered unchanged after standing for 16 hours at room temperature and after 3 hours refluxing in chloroform.

The mixed amino esters (60.5 mg., 0.159 mmole), in anhydrous t-butanol (10 ml.), were treated with freshly-prepared potassium t-butoxide (17.8 mg., 0.159 mmole). The initially pale yellow solution immediately turned dark brown. It was stirred at room temperature for 1 hour and then poured into ice-cold saturated ammonium chloride solution and extracted with chloroform. The chloroform extract was washed with water, dried over anhydrous magnesium sulfate, decolorized with activated carbon, and evaporated at 25° to give 60.7 mg. of a solid residue. This was chromatographed on a 0.5×4.5 cm column of 1.0 g. of neutral alumina (Woelm, activity II). Flution with methylene chloride afforded 40 mg. of solid in the first 5 ml. This was rechromatographed on a 0.5×5.5 cm column of 1.2 g. of alumina. Flution with 5 ml. of 1:1 benzenemethylene chloride gave 28 mg. of solid material whose IR spectrum showed only weak absorption at 5.6μ. Flution with 10 ml. of methylene chloride then gave 8.6 mg. of a crystalline compound, m.p. 121°–122°. The IR spectrum of this compound (KBr) showed peaks at 2.92 (N-H), 5.56 (β-lactam), 5.62, 5.79 (phthalimido), 5.82 (ester) and 6.03μ (C=C). The NMR spectrum had peaks at 2.25 (4H), 3.87 (1H,d,2.0 Hz), 4.30 (1H,d,2.0 Hz), 6.23 (3H), 7.70 (2H), 7.88 (3H). The compound has the structure

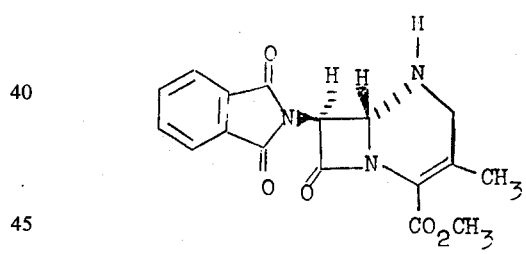

The systematic name for the nucleus is

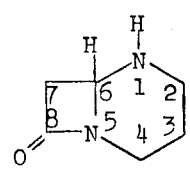

1,5-diaza-6S-bicyclo [4,2,0] octan-8-one.

Reaction of methyl 2-(2'S-chloro-3'S-phthalimido-4'-oxo)azetidinyl-3-methyl-2-butenoate with one molar equivalent of N-bromosuccinimide A mixture of the pure trans methyl ester (165 mg., 0.455 mmole), N-bromosuccinimide (81 mg., 0.455 mmole) and benzoyl peroxide (4 mg.), in carbon tetrachloride (12 ml), was brought to reflux. The heat source was then removed and replaced with a 100 watt Photoflood No. 2 lamp. Illumination of the stirred reaction mixture was maintained for 15 mins. The suspension was then cooled, filtered, and the filtrate evaporated to a white foam. This was chromatographed on a 0.5 × 13 cm column of 3.0 g of neutral alumina (Woelm, activity II Elution with methylene chloride afforded 206 mg. of a 60:40 mixture of mono bromo compounds. The n.m.r. spectrum of this mixture has peaks at 2.17 (4H), 3.73 (1H, d, 2Hz), 4.37 (1H, d, 2Hz), 5.27–5.65 (2H, m, two overlapping AB quartets), 6.15 (3H), 7.59 (1.2H), 7.82 (1.8H).

The structures of these compounds are

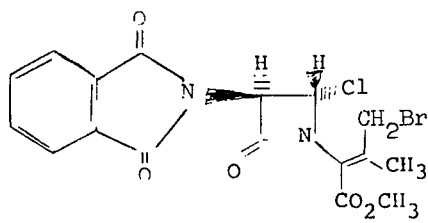

methyl 2-(2'S-chloro-3'S-phthalimido-4'-oxo)azetidinyl-3-methyl-4-bromo-trans-2-butenoate and

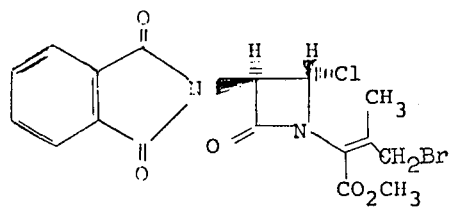

methyl 2-(2'S-chloro-3'S-phthalimido-4'oxo)azetidinyl-3-methyl-4-bromo-cis-2-butenoate.

Conversion of the cis- and trans-methyl 2-(2'S-chloro-3'S-phthalimido-4'-oxo)azetidinyl-3-methyl-4-bromo-2-butenoates to the cis- and transmethyl 2-(2'S-chloro-3'S-phthalimido-4'-oxo)azetidinyl-3-methyl-4-azido-2-butenoates The 60:40 mixture of monobrominated compounds (205 mg., 0.455 mmole), in chloroform (4 ml), was treated with tetramethylguanidinium azide (79.1 mg., 0.50 mmole). The solution immediately turned light yellow. It was stirred at room temperature for 4 hrs. and then diluted with chloroform, washed with water, treated with activated carbon, and dried over anhydrous magnesium sulfate. Evaporation then afforded 184 mg. of the mixed azides; i.r. : 4.7, 5.55, 5.62, 5.79μ; n.m.r.: 2.17 (4H), 3.76 (1H, m, overlapping doublets), 4.40 (1H, d, 2.0 Hz), 5.52 and 5.58 (0.8H, AB quartet of one isomer), 5.87 (1.2H, br), 6.15 (3H), 7.67 (1.2H), 7.87 (1.8H).

The structures of these compounds are

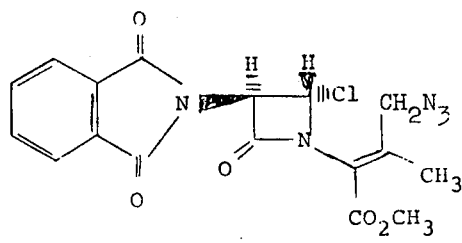

methyl 2-(2'S-chloro-3'S-phthalimide-4-oxo)azetidinyl-3-methyl-4-azido-trans-2-butenoate and

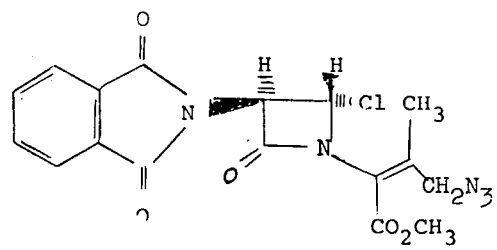

methyl 2-(2'S-chloro-3'S-phthalimido-4'-oxo)azetidinyl-3-methyl-4-azido-cis-2-butenoate Reaction of 2-benzyl-6-(1'-methoxycarbonyl-2'-methylprop-1'-enyl)-1-oxa-3,6-diaza-4S, 5R-bicyclo [3,2,0] hept-2-en-7one with one molar equivalent of a lithium thioalkoxide in hexamethylphosphoric triamide (Hydrolysis of the oxazoline ester to the oxazoline acid and rearrangement to the oxygen analog of Penicillin G The equation of the above-mentioned reaction is

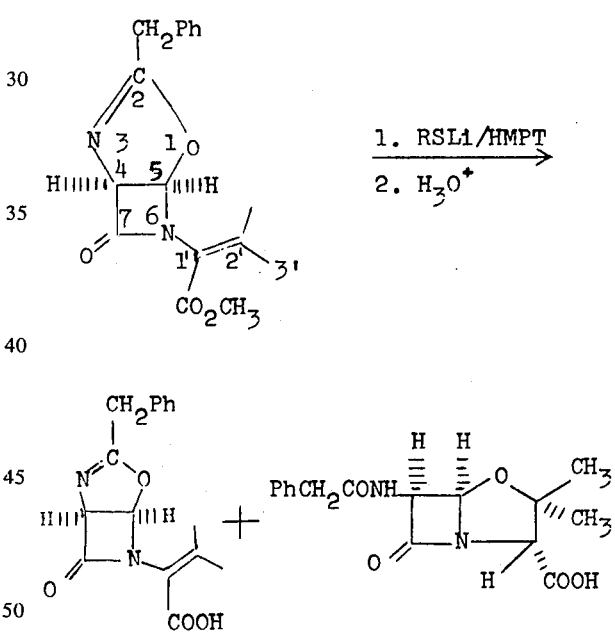

Where
R = n-C$_3$H$_7$, t-C$_4$H$_9$

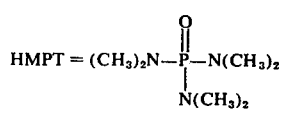

HMPT = (CH$_3$)$_2$N—P(=O)—N(CH$_3$)$_2$
         |
         N(CH$_3$)$_2$

·For the various experiments described below, HMPT was purified by distillation, under dry nitrogen, from lithium hydride or lithium aluminum hydride at 116°–117°C and 19–20 torr. It was stored over molecular sieves in a flask fitted with a rubber septum, and removed by syringe when needed. The lithium reagent was generated in HMPT by one of the following methods (Method A and Method B):

Method A: A round-bottomed flask was equipped with a magnetic stirrer and rubber septum. Two syringes were inserted into the septum, and dry nitrogen was passed through the flask. Then HMPT was introduced and the nitrogen sweep was continued for 1 hr. The desired amount of mercaptan was then added followed, at 25°, by an equivalent amount of a solution of n-butyllithium in hexane. The nitrogen sweep was continued for 15 min. and the flask was then sealed and stored in the refrigerator, aliquots of the reagent being withdrawn for reaction as needed. The solution was stable for about one month.

Method B: Lithium hydride was placed in a round-bottomed flask equipped with magnetic stirrer and rubber septum. The flask was flushed with nitrogen and HMPT was then added. The nitrogen sweep was then continued for 30 min. before addition of the mercaptan. The resulting mixture was stirred for 1.5 hr. at room temperature and was then filtered (under nitrogen in a dry box). The concentration of the reagent was determined by titration of an aliquot with N HCl, and the flask was then sealed and stored in the refrigerator until needed.

Experiment 1: The oxazoline (200 mg., 0.64 mmole), in HMPT (1.5 ml.) was treated, under nitrogen and with magnetic stirring, with 1.3 ml. of a 0.58 M solution (0.75 mmole) of t-BuSLi in HMPT prepared by method A. The addition was performed at room temperature during 0.5 hour and the reaction mixture was then allowed to stir overnight. Ice-cold water and ether were then added and the pH was adjusted to 2.3. The ether extract was washed with cold water, dried over anhydrous magnesium sulfate and evaporated to give a yellow oil. This was dissolved in ether and the solution extracted with icecold 5% bicarbonate. The bicarbonate extract was brought to pH 3 and extracted with ether. Evaporation of the dried ether extract gave 120 mg. of yellow oil which showed β-lactam absorption in the IR at 5–6μ and in the NMR at 4.8–5.0τ. This NMR spectrum changed after 7 hours at room temperature.

Experiment 2: The oxazoline (62 mg., 0.197 mmole), in HMPT (1 ml.), was swept with nitrogen for 30 min., and 0.35 ml. of a 0.615 M solution of t-BuSLi (0.215 mmole), prepared by method A, was then added dropwise during 2 hr. The mixture was stirred for 2 hr. after addition was complete and the acidic material was then isolated as described in experiment 1. It was a yellow oil weighing 23 mg.

Experiment 3: The oxazoline (66 mg., 0.21 mmole), in HMPT (3 ml.), was swept with nitrogen, and 0.3 ml. of a 0.73 M solution of n-C₃H₇Li, prepared by method A, was then added dropwise in two portions; 0.2 ml. were added during 0.5 hr., the mixture was stirred for 1.5 hr., and the remainder was then added during 0.5 hr. The reaction mixture was kept at room temperature for 8 hr. and then stored overnight in the refrigerator. Isolation yielded 24 mg. of acidic material.

Experiment 4: The oxazoline (64 mg., 0.20 mmole) was dissolved in HMPT (1 ml.) and the solution was degassed with a stream of dry nitrogen for 45 min. Then 0.44 ml. of a 0.47 M solution of t-BuSLi (prepared by method B) was added during 35 min. Stirring was continued for 2 hr. and the acidic material was then isolated. It weighed 15 mg.

Each of the acidic compounds isolated from experiments 2–4 featured NMR peaks at 2.52 (phenyl), 3.77 (d,3.5 Hz), 4.0 (d,3.5 Hz), 6.18, 7.77 and 8.47. These are the peaks of a compound having the structure

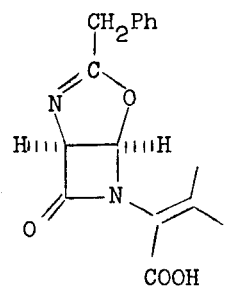

which could be obtained in crystalline form by an alternative route. Each of the NMR spectra of the acids from experiments 2–4 also showed extraneous peaks, the most prominent being a singlet at τ 6.3 and a singlet at 8.75, corresponding to a proton alpha to a carboxylic acid and methyl groups attached to a quaternary centre.

The crystalline oxazoline carboxylic acid was found to be inactive as an antibacterial agent at levels of 250 mcg./ml. However, all of the acidic fractions prepared by hydrolysis of the methyl ester showed significant antibacterial activity. The acid from experiment 3 (which also contained the biologically inactive oxazoline carboxylic acid) was dissolved in dimethylsulfoxide, chromatographed, and compared with Penicillin G. The two substances were spotted on duplicate ½ inch strips of S and S 589 blue ribbon paper. After overnight development in a system containing n-butanol 60:acetic acid:15:water 25, the strips were air dried and one set was sprayed with Riker penicillinase. Both sets were then subjected to bioautography on B. subtilis. The antibacterial agent in the acid from experiment 3 was found to have an Rf virtually identical to that of penicillin G and the bioactivity was eliminated by penicillinase treatment, as expected for a compound having a structure similar to that of penicillin G.

MIC data on penicillin G and on the acid from experiment 3 are summarized in the following table.

| Organism | Penicillin G Control MIC mcg./ml. | Acid from Experiment 3. M.I.C. mcg./ml. |
|---|---|---|
| D. pneumoniae + 5% serum* | .004 | 8 |
| Str. pyogenes + 5% serum* | .004 | 8 |
| S. aureus Smith at 10⁻⁴ dil'n | .016 | 16 |
| S. aureus Smith at 10⁻⁴ dil'n + 5% serum | .06 | 63 |

| Organism | Penicillin G Control MIC mcg./ml. | Acid from Experiment 3. M.I.C. mcg./ml. |
|---|---|---|
| S. aureus BX-1633-2 at $10^{-3}$ dil'n | 125 | 63 |
| S. aureus BX-1633-2 at $10^{-2}$ dil'n | >125 | 125 |
| S. aureus Meth. Resist. at $10^{-3}$ dil'n | 125 | 32 |
| S. aureus at $10^{-3}$ dil'n | 63 | 32 |
| S. aureus at $10^{-2}$ dil'n | >125 | >125 |
| Sal. enteritidis at $10^{-4}$ dil'n | 0.13 | 63 |
| E. coli Juhl at $10^{-4}$ dil'n | 32 | 63 |
| E. coli at $10^{-4}$ dil'n | 125 | 125 |
| K. pneumoniae at $10^{-4}$ dil'n | 2 | 63 |
| Pr. mirabilis at $10^{-4}$ dil'n | 1 | 63 |
| Pr. morganii at $10^{-4}$ dil'n | >125 | 63 |
| Ps. aeruginosa at $10^{-4}$ dil'n | >125 | 63 |
| Ser. marcescens at $10^{-4}$ dil'n | >125 | 63 |

*45% AAB at $10^{-3}$ dil'n + 50% Medium Shown

On the basis of its antibacterial spectrum, susceptibility to penicillinase, and NMR spectrum the antibacterial agent prepared during the hydrolysis of the oxazoline ester is assigned the structure

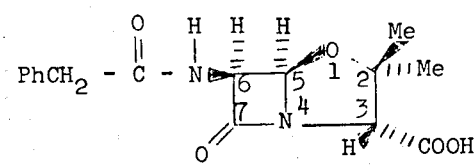

2,2-dimethyl-3R-carboxy-6S-phenylacetamido-1-oxa-4-aza-5R-bicyclo [3,2,0] heptan-7-one.

Reaction of 2-benzyl-6-(1'-methoxycarbonyl-2'-methylprop-1'-enyl)-1-oxa-3,6-diaza-4S,5R-bicyclo [3,2,0] hept-2-en-7-one with two equivalents of a lithium thioalkoxide in hexamethylphosphoric triamide The oxazoline (74 mg., 0.236 mmole) was dissolved in HMPT (1.5 ml.) and the solution was degassed with dry nitrogen for 0.5 hr. Then 0.83 ml. of a 0.612 M solution of t-BuSLi (0.508 mmole), prepared by method A, was added during 0.5 hr. and the mixture was stirred overnight. The acidic fraction weighed 33 mg. and showed antibacterial activity in a plate assay vs. S. lutea. The NMR spectrum showed β-lactam protons at 4.0 and 4.7 Hz, phenyl absorption at 2.6, methylene absorption at 6.12, a singlet at 6.2 and methyl peaks at 8.75. The characteristic peaks of the oxazolinecarboxylic acid, 2-benzyl-6-(1'-carboxy-2'-methylprop-1'-enyl)-1-oxa-3,6-diaza-4S,5R-bicyclo [3,2,0] hept-2-ene-7-one, were absent from the spectrum.

The same result was obtained from an experiment with t-BuSLi prepared by method B.

These experiments demonstrate that hydrolysis of 2-benzyl-6-(1'-methoxycarbonyl-2'-methylprop-1'-enyl)-1-oxa-3,6-diaza-4S,5R-bicyclo [3,2,0] hept-2-en-7-one to the carboxylic acid is effected by lithium thioalkoxides in HMPT and that rearrangement to the oxapenicillin occurs under the experimental conditions.

Reaction of the epimeric methyl 2-(2'-chloro-3'-S-amino-4'-oxo)azetidinyl-3-methyl-2-butenoates with benzyl chloroformate (carbobenzoxy chloride)

The crystalline p-toluenesulfonic acid salt of methyl 2-(2'R-chloro-3'S-amino-4'-oxo)azetidinyl-3-methyl-2-butenoate (576 mg., 1.42 mmoles) was dissolved in spectroscopic grade chloroform (6 ml.), and 1.080 g. (5 molar equivalents) of tetramethylguanidinium chloride were added. The mixture was refluxed for 3.5 hr. and then cooled, washed with water, dried over anhydrous magnesium sulfate, and carbobenzoxy chloride (297 mg., 1.7 mmoles) was added followed, dropwise, by a solution of triethylamine (185 mg., 1.83 mmoles) in dry chloroform (5 ml.). After 45 min. stirring at room temperature the reaction was stopped by addition of water. The organic layer was dried and evaporated to a residue of 353 mg. This was chromatographed on silica gel and the column eluted with 1:1 petroleum ether (30°–60°) - ethyl acetate; 17 thirty ml. fractions were collected. Fractions 2–4 gave 108 mg. of a compound having the structure

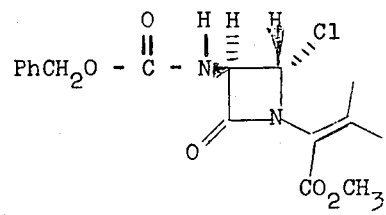

The NMR spectrum of this compound has peaks at 2.67 (5H), 4.20 (1H,d,2Hz), 4.87 (2H), 5.35 (1H,d,2Hz), 6.27 (3H), 7.73 (3H), 8.03 (3H).

Fractions 12–17 afforded 54 mg. of a compound assigned the structure

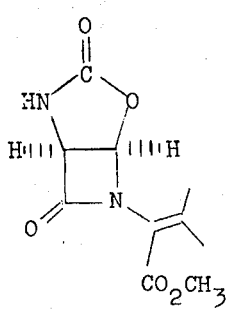

This fused β-lactam-oxazolidone has a molecular ion at m/e 240 in its mass spectrum. The IR spectrum has peaks at 3.0, 5.56, 5.62, 5.78, 6.10μ. The NMR spectrum has peaks at 2.87 (1H,br), 3.92 (1H,d,4Hz), 5.08 (1H,d,4Hz), 6.20 (3H), 7.70 (3H), 8.02 (3H).

Reaction of 2-(2'-chloro-3'S-amino-4'-oxo)azetidinyl-3-methyl-2-butenoic acid with carbobenzoxy chloride

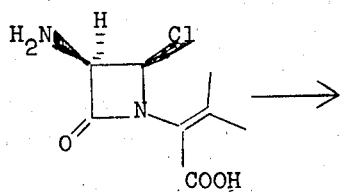

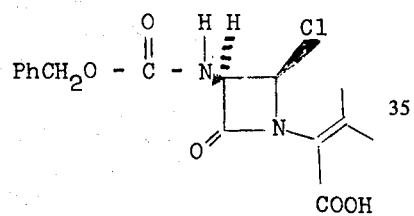

The p-toluenesulfonic acid salt of anhydro-6-aminopenicillin (557 mg., 1.51 mmoles) was chlorinated in methylene chloride at 0°. The solvent was then removed under reduced pressure at 20°. The residue was dissolved in a mixture of water (4 ml.) and acetone (5 ml.) and this solution was maintained at 0° for 3 hr. to effect hydrolysis of the acid chloride. Then sodium bicarbonate (705 mg., 8.4 mmoles) was added followed, dropwise at 0°, by a solution of carbobenzoxy chloride (660 mg., 1.51 mmoles) in dry acetone (5 ml.). The reaction mixture was stirred for 1 hr. and the product was then isolated by dilution with water, extraction with ether, drying over anhydrous magnesium sulfate, and evaporation. The IR spectruum showed peaks at 3.0, 5.60, 5.62, 5.82–5.88μ.

This experiment demonstrates that the amino acid can be acylated successfully.

Chlorination of anhydro-α-phenoxyethylpenicillin

The anhydropenicillin (500 mg., an 80:20 L:D mixture of side chain diastereomers) was chlorinated at room temperature in methylene chloride using a strong sweep of chlorine for 15–20 seconds. The solvent was then removed at 20°. The resulting product is a mixture of isomers having the structure

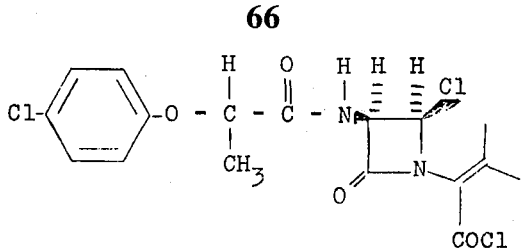

Its NMR spectrum shows peaks at 2.3 (1H,d,9Hz), 2.75 (2H,d,9Hz), 3.13 (2H,d,9Hz), 3.92 (1H,m), 4.45 (1H,m), 5.28 (1H,m), 7.74 (3H), 7.86 (3H), 8.40 (3H,d,7Hz). The IR spectrum shows peaks at 2.95, 5.55, 5.91μ.

This experiment demonstrates that a 6-acylamino anhydropenicillin can be chlorinated successfully.

Hydrolysis of the anhydro-α-phenoxyethylpenicillin chlorination product

The above-mentioned trichloro compound was dissolved in acetone (5 ml.), the solution cooled to 0°, and a solution of sodium bicarbonate (284 mg.) in ice-cold water (5 ml.) was added dropwise with stirring. Some oily material precipitated during this addition and acetone (15 ml.) was, therefore, added when the addition was complete. The resulting pale yellow solution was stirred for 2 hr. at 0° and then diluted with cold water (100 ml.). Extraction with methylene chloride, drying over anhydrous magnesium sulfate, and evaporation afforded a pale yellow oil. This material is assigned the structure

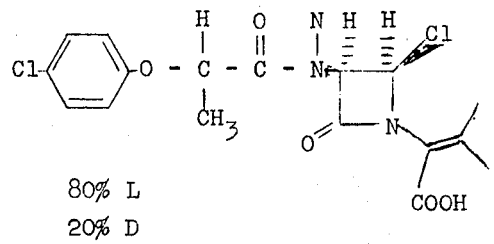

80% L
20% D

The IR spectrum showed peaks at 2.9, 5.58, 5.85μ. The compound was dissolved in methylene chloride and the solution extracted with 5% sodium bicarbonate. The aqueous extract was re-acidified to pH 2.5 and re-extracted with methylene chloride. Evaporation of the dried methylene chloride extract gave material, having high antibacterial activity vs. S. lutea, which is assigned the structure

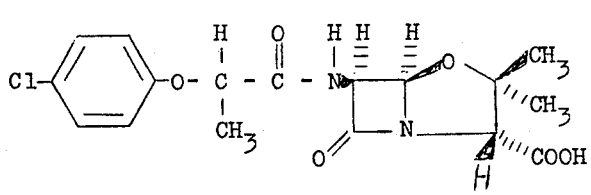

Treatment of this material with diazomethane gave a methyl ester which showed, in the IR, a peak at 5.6μ and, in the NMR a peak at 8.75 consistent with the presence of a β-lactam and methyl groups attached to an oxazolidine ring.

In a second experiment, the chlorination product from 215 mg. (0.62 mmole) of anhydro-α-phenoxyethylpenicillin was dissolved in ice-cold tetrahydrofuran (3 ml.) and to the colorless solution was added ice-cold water (2 ml.). The resulting solution was stirred at 0° for 2 hr., then diluted with ice-cold saturated sodium chloride and extracted with methylene chloride. Evaporation of the dried methylene chloride extract afforded 277 mg. of a white foam. The NMR spectrum of this dichloro acid shows peaks at 2.30 (H, br), 2.72 (2H,d,8Hz), 3.10 (2H,d, 8Hz), 3.83 (1H,br), 4.40 (1H,br), 5.22 (1H,q), 7.67 (3H), 7.93 (3H), 8.40 (3H,d). The IR spectrum showed peaks at 2.96, 5.60, 5.8 μ

Reaction of 2-(2'-chloro-3'S-amino-4'-oxo)azetidinyl-3-methyl-2-butenoic acid with phenylacetyl chloride

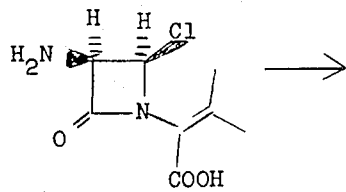

The p-toluenesulfonic acid salt of anhydro-6-aminopenicillin (242 mg.) was chlorinated and the product hydrolyzed in aqueous acetone as already described. To the resulting solution (volume 20 ml.) at 0° was added in portions sodium bicarbonate (275 mg.) followed by a solution of phenylacetyl chloride (152 mg.) in aceton (5 ml.) in one portion. The mixture was stirred for 30 min. and then diluted with water and extracted with methylene chloride; this extract was discarded. The aqueous phase was brought to pH 3 and extracted with methylene chloride. This extract was dried over anhydrous magnesium sulfate and evaporated to give the desired compound. The IR and NMR spectra were consistent with the assigned structure.

Chlorination of anhydrobenzylpenicillin

Anhydropenicillin G (176 mg., 0.56 mmole) was dissolved in methylene chloride (7 ml.) and the solution was chlorinated at room temperature for 30 sec. with a strong sweep of chlorine. The solvent was then removed immediately at 20° under reduced pressure to give a pale yellow foam. The IR spectrum of this foam shows peaks at 2.92, 5.5, 5.95μ. The NMR spectrum shows that the product is a 4:1 mixture of 2-(2'-R-chloro-3'S-phenylacetamido-4'-oxo)azetidinyl-3-methyl-2-butenoyl chloride and its 2'S epimer. The major isomer has the structure

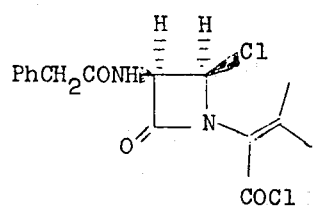

Its NMR spectrum shows peaks at 2.71 (5H), 3.07 (1H,d,9Hz), 3.97 (1H,d,4.5 Hz), 4.52 (1H,q,4.5,9Hz), 6.37 (2H), 7.78 (3H), 7.92 (3H).

The minor isomer has the structure

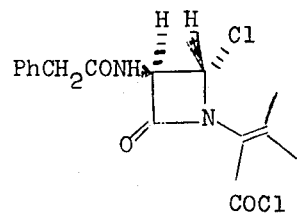

Its NMR spectrum shows peaks at 2.71 (5H), 3.07 (1H,d,9Hz), 4.12 (1H,d,2Hz), 5.17 (1H,q,2,9 Hz), 6.44 (2H), 7.78 (6H).

Hydrolysis of the anhydrobenzylpenicillin chlorination product

The above-mentioned mixture of dichlorides (from 176 mg. of anhydropenicillin) was dissolved in acetone (6 ml.) and water (4 ml.) was added followed, at 0°, by excess sodium bicarbonate. The mixture was stirred for 2.3 hr. and then diluted with water (50 ml.) and extracted thrice with methylene chloride and once with ether. Acidification of the aqueous phase to pH 2.5, extraction with methylene chloride and evaporation of the dried methylene chloride extract afforded 36 mg. of an oil whose IR and NMR spectra indicated it to consist mainly of unhydrolyzed acid chloride.

In a second experiment anhydropenicillin G (105 mg.) was chlorinated and the resulting white foam was dissolved in icecold tetrahydrofuran (3 ml.) and cold water (1 ml.) was added. The clear yellow solution was maintained at 0° for 2 hr. and then poured into a mixture of water and ice, and extracted with methylene chloride. Evaporation of the dried methylene chloride extract afforded 113 mg. (98%) of a chloro acid whose IR and NMR spectra showed it to have the structure

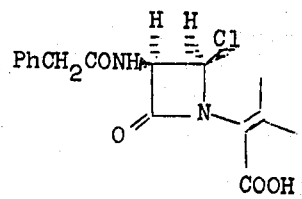

The IR spectrum showed peaks at 3.05, 5.62, 5.90, 5.95μ. The NMR spectrum showed peaks at 2.72 (5H), 3.10 (1H,d,8 Hz), 3.93 (1H,d,4.5 Hz), 4.42 (1H,q,4.5,8Hz), 6.32 (2H), 7.72 (3H), 8.01 (3H).

In a third experiment, the chloro acid from 333 mg. of anhydropenicillin G was treated in ether with an excess of ethereal diazomethane. The solution was stirred for 2 hr. at room temperature and then evaporated to dryness. The residue was left in the refrigerator overnight and then, in methylene chloride, shaken with 5% bicarbonate, dried and evaporated. The residue was chromatographed on silica gel; elution with 1:1 petroleum ether:ethyl acetate afforded 189 mg. (51%, m.p. 110.5°–111°) of the methyl ester having the structure

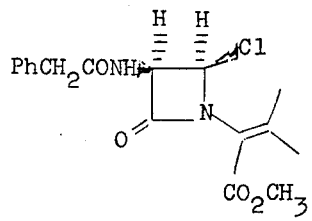

and 40 mg. (12%) of the oxazoline

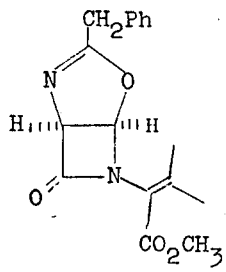

Both compounds were identical to those obtained from the p-toluenesulfonic acid salt of methyl 2-(2'R-chloro-3'-S-amino-4'-oxo)azetidinyl-3-methyl-2-butenoate. The reaction sequence proves that chlorination proceeds in the same manner with the phenylacetamido and amino side chains.

Synthesis of
2-benzyl-6-(1'-carboxy-2'-methylprop-1'-enyl)-1-oxa-3,6-diaza-4S,5R-bicyclo [3,2,0] hept-2-en-7-one

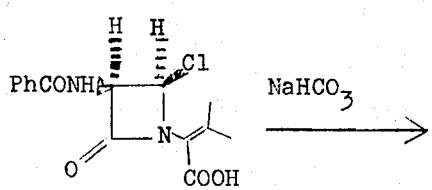

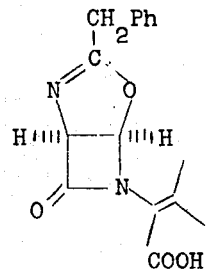

The chloro acid prepared from 640 mg. of anhydropenicillin G was dissolved in 5% bicarbonate solution. This was extracted with methylene chloride and then acidified to pH 2. Extraction with methylene chloride and evaporation of the dried extract afforded a crystalline residue. Recrystallization from ethyl acetate gave 320 mg. (53%) of the oxazoline carboxylic acid, m.p. 119°–122° dec. The IR spectrum shows a broad peak at 4$\mu$, and as well peaks at 5.64, 5.92, 6.1$\mu$, consistent with the zwitterionic structure

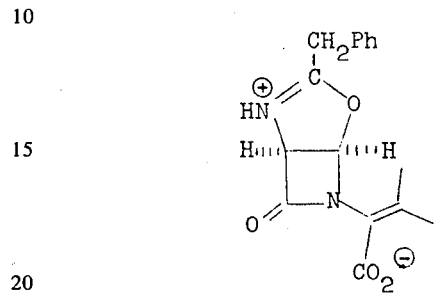

The NMR spectrum (in $D_2O$) shows peaks at 2.67 (5H), 3.88 (1H,d,3.8Hz), 4.75 (1H,d,3.8 Hz), 6.25 (2H), 8.09 (3H), 8.69 (3H). Anal. Calcd. for $C_{16}H_{16}N_2O_4$: C, 63.99; H, 5.37; N, 9.33. Found: C, 64.26; H, 4.89; N, 9.54.

Preparation of anhydrocarbobenzoxypenicillin

The p-toluenesulfonic acid salt of anhydro-6-aminopenicillin (2.90 g., 7.84 mmoles) was dissolved in methylene chloride (20 ml.) and the solution was cooled to 0° and treated concurrently with pyridine (820 mg.) in methylene chloride (15 ml.), and carbobenzoxy chloride (1.400 g., 8.1 mmoles) in methylene chloride (15 ml.). Addition of the two reagents was complete in 10 min. and, after an additional 10 min., the mixture was washed with ice-cold N HCl, ice-cold saturated sodium chloride, dried and evaporated to give 2.740 g. of a white foam. This was crystalized from a mixture of ether and petroleum ether to give 2.33 g. (89.5%) of anhydrocarbobenzoxypenicillin having the structure

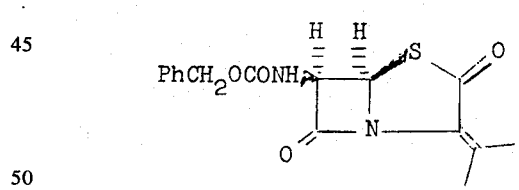

The NMR spectrum showed peaks at 2.65 (5H), 4.17 (1H), 4.45 (1H), 4.85 (2H), 7.82 (3H), 7.93 (3H).

Preparation of
anhydro-2,2',2''-trichloroethoxypenicillin

The p-toluenesulfonic acid salt of anhydro-6-aminopenicillin (2.396 g., 6.47 mmoles) was dissolved in methylene chloride (25 ml.) and the solution was cooled and treated concurrently with pyridine (0.633 g., 8 mmoles) in methylene chloride (10 ml.) and 2,2',-2''-trichloroethyl chloroformate (1.437 g., 6.9 mmoles) in methylene chloride (10 ml.). At the end of the addition t.l.c. examination of the reaction mixture revealed a single spot (and a spot at the origin corresponding to pyridinium chloride). The mixture was stirred an additional 15 min. and then washed with cold N HCl, dried and evaporated. The IR and NMR spectra of the resulting white foam were consistent with the structure

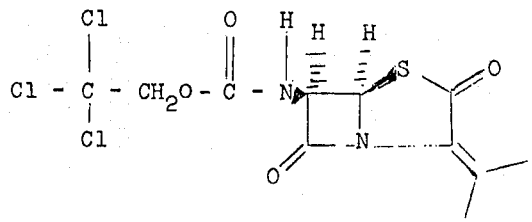

Conversion of anhydro-2,2′,2″-trichloroethoxypenicillin into benzhydryl 2-(2′R-chloro-3′S-trichloroethoxycarbonylamino-4′-oxo)azetidinyl-3-methyl-2-butenoate

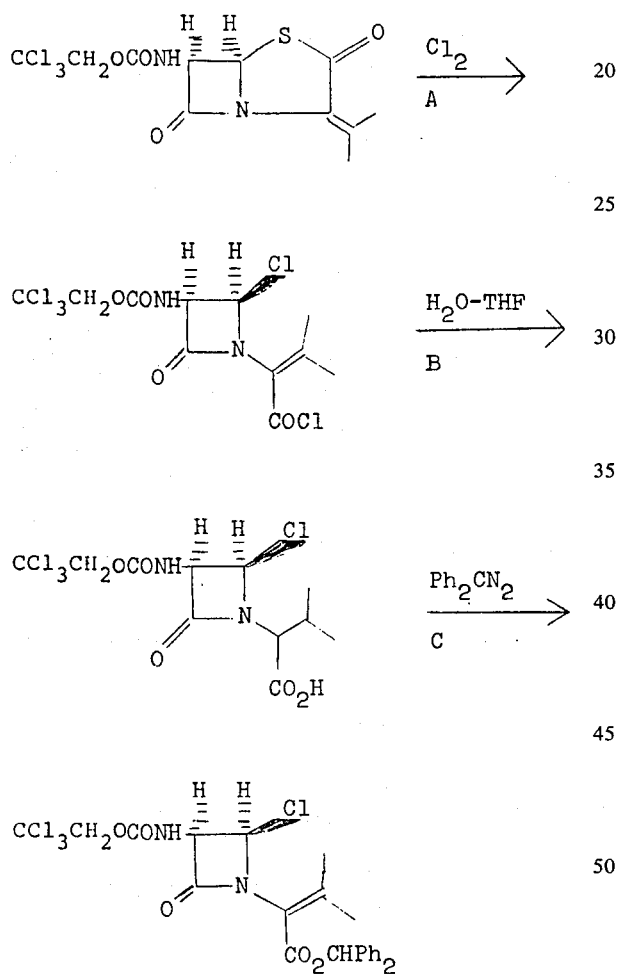

A. The anydropenicillin (453 mg., 1.245 mmole) was chlorinated in the usual way to give a white foam. The NMR spectrum of this foam showed peaks at 3.35 (1H,d,10Hz), 3.83 (1H,d,4.0 Hz), 4.52 (1H,d,4.0,10Hz), 5.21 (2H), 7.71 (3H), 7.81 (3H).
B. Hydrolysis was performed at 0° for 2 hr. in tetrahydrofuran (10 ml.) and water (1 ml.). The resulting acid crystallized from chloroform. Its NMR spectrum showed peaks at 3.17 (1H,d,8Hz), 3.82 (1H,d,4Hz), 4.56 (1H,q,4,8Hz), 5.20 (2H), 7.67 (3H), 7.93 (3H).
C. The acid was dissolved in hot benzene (40 ml.) and diphenyl diazomethane (363 mg., 1.87 mmoles) was added. The resulting solution was refluxed for 40 min. and then evaporated to dryness. The dark red oil was chromatographed on silica gel. Elution with graded mixtures of petroleum ether and ethyl acetate afforded 480 mg. (70%) of the benzhydryl ester. Its NMR spectrum showed peaks at 2.68 (10H), 3.06 (1H), 3.51 (1H,d,9Hz), 4.04 (1H,d,4.5Hz), 4.67 (1H,q,4.5,9Hz), 5.23 (2H), 7.72 (3H), 7.98 (3H).

Equilibration of the R and S benzhydryl 2-(2′-chloro-3′S-trichloroethoxycarbonylamino-4′-oxo)azetidinyl-3-methyl-2-butenoates The benzhydryl ester (181 mg., 0.317 mmole) and tetramethylguanidinium chloride (240 mg., 5 molar equivalents) were refluxed in chloroform (5 ml.) for 5 hr. The cooled reaction mixture was then diluted with methylene chloride, washed with saturated sodium chloride solution, dried and evaporated. The resulting white foam was found to be a 60:40 mixture of the starting material and its 2′S epimer, which has the structure

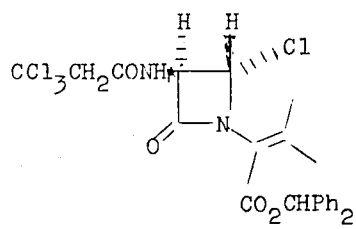

The NMR spectrum of this compound shows peaks at 2.68 (10H), 3.06 (1H), 4.30 (1H,d,2Hz), 4.95 (1H,d,2Hz), 5.27 (2H), 7.72 (3H), 7.98 (3H).

In a second experiment, 4.851 g. (8.65 mmoles) of the 2′R isomer and tetramethylguanidinium chloride (7.9 g., 6-molar equivalents) were refluxed in spectroscopic grade chloroform (20 ml.) for 4 hr. The product was a 70:30 mixture of 2′S:2′R isomers, i.e., these conditions, which involve a higher concentration of reactants, cause a significant improvement in the proportion of the 2′S isomer.

Tetramethylguanidinium formate

Commercial 98% formic acid was distilled from anhydrous cupric sulfate at 46° and 113 torr. The distillate was redistilled from anhydrous cupric sulfate at 41° and 105 torr to give anhydrous formic acid.

Tetramethylguanidine (22 g., 0.19 mole) was dissolved in anhydrous ether (100 ml.) and to this solution at 0° was added a solution of anhydrous formic acid (7.1 ml., 0.198 mole) in anhydrous ether (40 ml.). The resulting salt crystallized. It was collected, washed with ether, dried in high vacuum and recrystallized from chloroform-ether.

The salt was extremely hydroscopic and became oily after 3 min. exposure to atmospheric moisture. The oily material gave unsatisfactory results in the following experiments.

If the formic acid was not made anhydrous prior to formation of the salt, the latter was obtained as an oil which gave unsatisfactory results. The salt has the structure

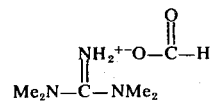

Reaction of benzhydryl 2-(2'-chloro-3'S-trichloroethoxycarbonylamino-4'-oxo)azetidinyl-3-methyl-2-butenoate with tetramethylguanidinium formate. Preparation of 2-trichloroethoxy-6-(1'-benzhydryloxycarbonyl-2'-methylprop-1'-enyl)-1-oxa-3,6-diaza-4S,5R-bicyclo[3,2,0]hept-2-en-7-one A 2:1 2'S:2'R mixture of benzhydryl esters (953 mg., 1.7 mmoles) and tetramethylguanidinium formate 4.992 g. (30.5 mmoles) were refluxed in spectroscopic grade chloroform (12 ml.). The reaction was complete in 1.5 hr. and the mixture was, therefore, cooled, washed successively with water and saturated sodium chloride, dried and evaporated. The residue was chromatographed over 30 g. of silica gel. Elution was performed with 100 ml. each of 90/10, 80/10 and 70/30 petroleum ether-ethyl acetate, with 30 ml. fractions being collected. Fractions 2–5 were combined to give 142 mg. (24%) of a compound having the structure

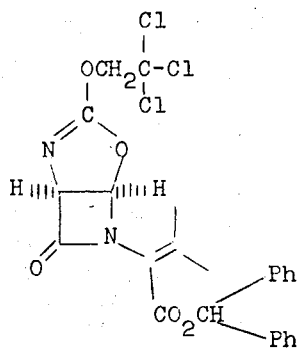

The IR spectrum of this oxazoline shows peaks at 5.61, 5.76, 5.81, 6.07 μ

The n.m.r. spectrum has peaks at 2.68 (10H), 3.08(s,1H), 3.99(1H,d,3.5Hz), 4.86(1H,d,3.5Hz), 5.15(1H,d,12Hz), 5.27 (H,d,12Hz; the methylene protons of the trichloroethyl group are non-equivalent), 7.73(3H), 8.06(3H).

The mass spectrum shows chlorine multiplets characteristic of the presence of 3 chlorines, including a multiplet at m/e 522, the molecular ion.

Chlorination of anhydrocarbobenzoxypenicillin

The anhydropenicillin (470 mg., 1.47 mmoles) was chlorinated in methylene chloride for 15 seconds. After an additional 30 seconds the solvent was removed to give a white foam which consisted of a 77:23 mixture of dichlorides, the compound having the 2'R-chloro configuration predominating. Its structure is

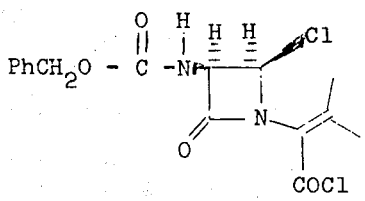

The NMR spectrum of this compound has peaks at 2.69 (5H), 3.14 (1H,d,9Hz), 3.93 (1H,d,4Hz), 4.75 (1H,q,4,9Hz), 4.83 (2H), 7.80 (3H), 7.90 (3H)

The minor isomer has the structure

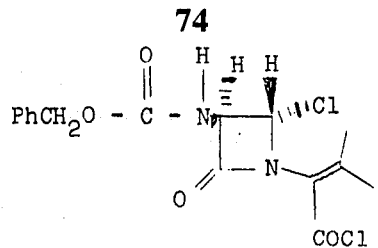

The NMR spectrum of this compound has peaks at 2.69 (5H), 3.14 (1H,d,9Hz), 4.10 (1H,d,2Hz), 4.84 (2H), 5.17 (1H,d,2Hz), 7.80 (6H).

Hydrolysis of the anhydrocarbobenzoxypenicillin chlorination product

The dichloride (a 77:23 2'R:2'S mixture from 470 mg. of the anhydropenicillin) was dissolved in cold tetrahydrofuran (10 ml.) and ice-cold water (1 ml.) was added. The mixture was left for 3 hr. at 0° and then added to ice-cold saturated sodium chloride solution. Extraction with methylene chloride and evaporation of the dried methylene chloride extract afforded 535 mg. of the chloro acids. The major isomer has the structure

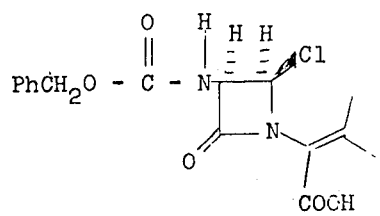

The NMR spectrum of this compound has peaks at 2.68 (5H), 3.63 (1H,d,10Hz), 3.87 (1H,d,4Hz), 4.55 (1H,d,4,10Hz), 4.83 (2H), 7.72 (3H), 7.98 (3H).

Reaction of 2-(2'R-chloro-3'-S-benzyloxycarbonylamino-4'-oxo)azetidinyl-3-methyl-2-butenoic acid with sodium bicarbonate. Preparation of the oxygen analog of a 5-epianhydropenicillin The chloro acid from 470 mg. of the anyhydropenicillin, in acetone (5 ml.), was added to a solution of sodium bicarbonate (247 mg., 2.94 mmoles) in water (10 ml.). After 1 minute crystallization began. The mixture was stirred for 15 min. and then diluted with saturated sodium chloride solution (20 ml.) and extracted twice with methylene chloride (10 ml. each) and once with ether (10 ml.). The combined organic extracts were dried over anhydrous magnesium sulfate and evaporated. The crystalline residue weighed 216 mg. Chromatography on silica gel afforded 185 mg. of material which was recrystallized to give a compound, m.p. 170°–172° dec., [α] $_D^{25}$ −64.5° (c 0.45, CHCl$_3$), which has the structure

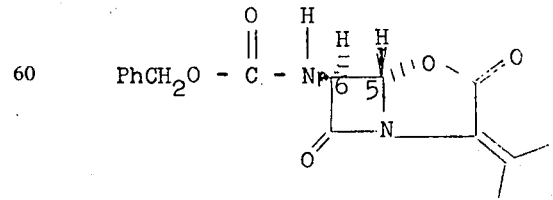

Anhydrocarbobenzoxypenicillin has [α] $_D^{25}$ +259° (c 1, CHCl$_3$). The 5-epioxaanhydropenicillin has IR absorption at 2.98, 5.55, 5.65, 5.88 and 6.51 μ. The NMR spectrum has peaks at 2.44 (6H), 4.14 (1H,d,1.8Hz), 4.82 (2H), 4.98 (1H,q,1.8,8Hz), 7.82 (3H), 7.88 (3H). The mass spectrum shows the molecular ion at 316.

Anal. Calcd. for $C_{16}H_{16}N_2O_5$: C, 60.75; H, 5.10; N, 8.86. Found: C, 60.67; H, 5.20; N, 8.99.

Preparation of 6-phthalimido oxapenicillin

Anhydro-6-phthalimidopenicillin (606 mg.) was chlorinated in methylene chloride with a strong sweep of chlorine for 30 seconds and the solvent was then removed immediately. A 70:30 mixture of 2'S:2'R 2-(2'chloro-3'S-phthalimido-4'-oxo)-azetidinyl-3-methyl-2-butenoyl chlorides was obtained. This mixture was hydrolyzed in a mixture of tetrahydrofuran (25 ml.) and water (2 ml.) at 0° for 4 hr. The resulting acid was a 77.23 mixture. The major isomer has the structure

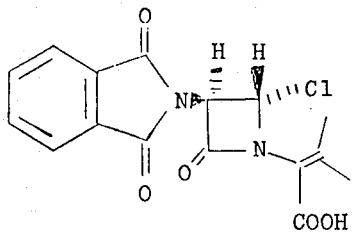

Its NMR spectrum has peaks at 2.12 (4H), 3.62 (1H,d,2Hz), 4.38 (1H,d,2Hz), 7.84 (3H), 8.11 (3H). The minor isomer, which has the 2'R configuration, has already been described.

The trans acid was crystallized from 1:1 ethyl acetate-ligroin, m.p. 164°–166° dec. (sealed capillary). The crystalline trans acid in methylene chloride, was shaken with 5% bicarbonate for 5 min. The aqueous phase was then separated, acidified to pH 4.5 – 5.0 and extracted with methylene chloride. It was then acidifid to pH 2.5 and extracted twice with methylene chloride and twice with chloroform. Evaporation of the combined dried organic extracts afforded 30 mg. of material which showed antibacterial activity versus S. lutea at one-tenth the level of phthalimidopenicillin. The NMR spectrum showed a peak at 8.73 for methyl groups on an oxazolidine ring and β-lactam absorption at 4.6. The active compound has the structure

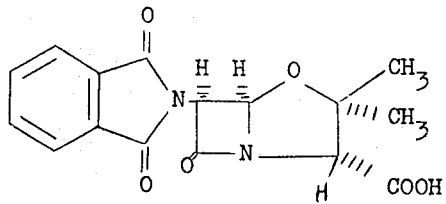

Preparation of benzhydryl 2-(2'S-chloro-3'S-phthalimido-4'-oxo)azetidinyl-3-methyl-2-butenoate The crystalline trans chloro acid (526 mg., 1.515 mmole) was dissolved in boiling ethyl acetate (12 ml.) and the solution was then cooled to room temperature and treated with diphenyldiazomethane (330 mg., a 10% excess) in ethyl acetate (18 ml.). Evolution of nitrogen commenced immediately and was complete after 10 min. The mixture was then refluxed for 1 hr. and evaporated to dryness. The residue was chromatographed on 30 g. of silica gel. Elution with petroleum ether-ethyl acetate (70–30) removed some unreacted diphenyldiazomethane. Continued elution with petroleum ether-ethyl acetate (1:1) afforded 772 mg. (99%) of the compound having the structure

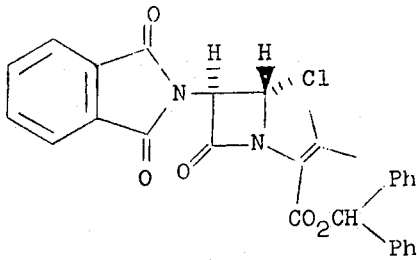

The n.m.r. spectrum shows peaks at 2.23(4H,d), 2.67 (10H,m), 3.00(1H,s), 3.87(1H,d,1.8Hz), 4.47(1H,d,1.8Hz), 7.68(3H), 7.90(3H).

Reaction of benzhydryl 2-(2'S-chloro-3'S-phthalimido-4'-oxo)azetidinyl-3-methyl-2-butenoate with tetramethylguanidinium formate. Preparation of benzhydryl 2-(2'R-formyloxy-3'S-phthalimido-4'-oxo)azetidinyl-3-methyl-2-butenoate The benzhydryl ester (150 mg., 0.292 mmole) and tetramethylguanidinium formate (260 mg., 1.61 mmoles, 5.5 molar equivalents) were refluxed in chloroform (spectroscopic grade) for 17 hr. The solution was washed successiely with water, saturated sodium chloride and water, and dried over anhydrous magnesium sulfate. The residue, after removal of the solvent, was chromatographed over 18 g. of silica gel. Elution with graded mixtures of petroleum ether-ethyl acetate afforded 54 mg. of a crystalline compound having the structure

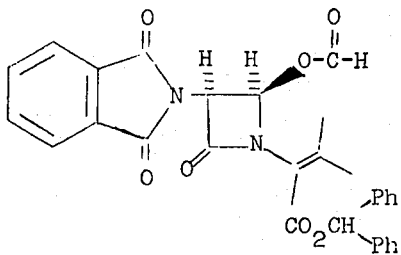

The n.m.r. spectrum of this compound has peaks at −0.74(1H), 2.19(4H,d), 3.02(1H,s), 2.67(10H,m), 3.92 (1H,d,3.8Hz), 4.59 (1H,d,3.8Hz), 7.75(3H), 8.11(3H).

Curtuis rearrangement of the anhydrobenzylpenicillin chlorination product

Anhydropenicillin G (206 mg.) was chlorinated for 20 sec. at −6° C. in methylene chloride. The solution was maintained for 2 min. at this temperature and then evaporated to dryness. The residue, in chloroform (10 ml.), was treated at −6° with tetramethylguanidinium azide (120 mg., 1.2 molar equivalents) in chloroform (5 ml.). The resulting solution was maintained for 1 hr. at −6°, and its IR spectrum was then determined. It showed peaks at 3.0, 4.67, 5.60, 5.95μ, as expected for the formation of a compound having the structure

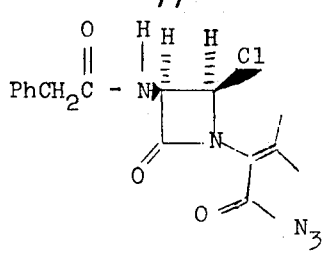

The acid azide was isolated by extracting the chloroform solution with water, sodium chloride solution, drying, and removal of the solvent. It was then dissolved in methylene chloride (10 ml.), and the solution heated to reflux. After 15 min. the IR spectrum showed a new peak at 4.43μ, about twice as intense as the peak at 4.67μ. After an additional 15 min. the peak at 4.43μ was now about six times as intense as the peak at 4.67μ. After a total of 2 hr. of refluxing the reaction seemed complete and the IR spectrum showed peaks at 3.12, 4.42, 5.58, 5.98μ.

Evaporation gave a compound having the structure

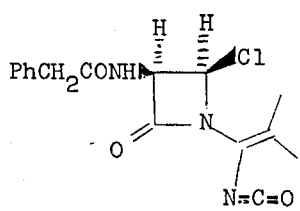

This isocyanate, in tetrahydrofuran (20 ml.), was added during 40 min. to 1:1 aqueous tetrahydrofuran containing 0.65 ml. of N HCl. The mixture was stirred for 80 min. after addition was complete and was then diluted with water (200 ml.), saturated with sodium chloride and extracted exhaustively with methylene chloride. The methylene chloride extract was dried over anhydrous magnesium sulfate and evaporated to give 139 mg. of a white foam. The NMR spectrum of this foam showed β-lactam peaks in the 3.9–4.7τ region, absence of peaks in the region of the allylic methyl groups and several peaks in the 8.5–9τ region. Chromatography on silica gel afforded two compounds. One, a crystalline material, was identified as isobutyramide [$(CH_3)_2CHCONH_2$]; the other was a 2:1 mixture of epimers having the structure

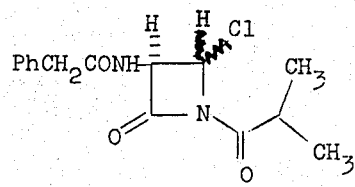

The cis isomer, having the structure

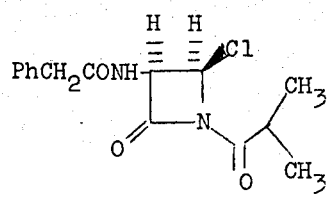

has NMR peaks at 2.63 (5H), 3.5 (1H,d,8Hz), 3.94 (1H,d,5Hz), 4.32 (1H,q,8Hz), 6.28 (2H), 6.83 (1H,m), 8.75 (6H,m).

The trans isomer, having the structure

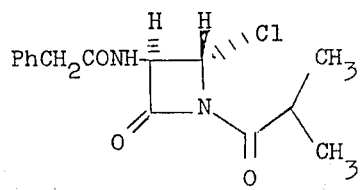

has NMR peaks at 2.63 (5H), 3.5 (1H,d,8Hz), 4.07 (1H,d,2Hz), 5.48 (1H,q,2,8Hz), 6.33 (2H), 6.83 (1H,m), 8.75 (6H,m).

The mass spectrum of the mixture of isomers shows an M-1 peak at 306 and 308 and a peak at 272 corresponding to loss of chlorine from the molecular ion.

As disclosed above, the present invention includes a variety of processes including those described in detail below. To avoid unnecessary repetition, it is to be noted that in the equations given below there is frequent reference to the substituent having the formula

wherein frequently $R^2$ is hydrogen and $R^1$ is acyl. By acyl is meant a group having the formula

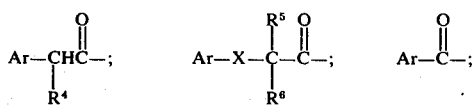

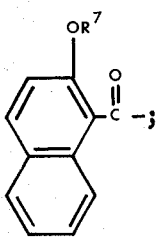

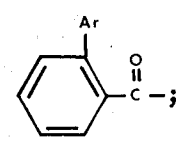

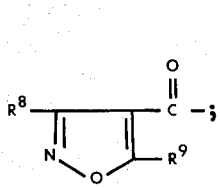

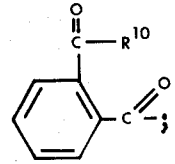

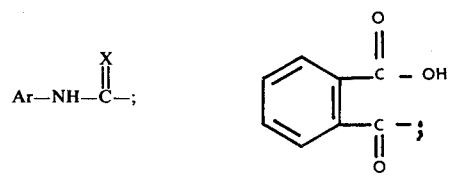

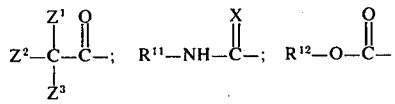

wherein $R^{12}$ represents 2,2,2-trichloroethyl or benzyl; wherein $R^4$ represents hydrogen, amino, carbobenzoxyamino, phenyl, fluoro, chloro, bromo, iodo, hydroxy, (lower)alkanoyloxy or (lower)alkoxy; X represents oxygen or sulfur; $R^5$ and $R^6$ each represent hydrogen, phenyl, benzyl, phenethyl or (lower)alkyl; $R^7$ represents (lower)alkyl; $R^8$ and $R^9$ each represent (lower)alkyl, (lower)alkylthio, benzylthio, cyclohexyl, cyclopentyl, cycloheptyl, benzyl, phenethyl, phenylpropyl, furyl, thienyl, naphthyl or Ar; $R^{10}$ represents (lower)alkylamino, di(lower)-alkylamino, cycloalkylamino having 3 to 7 carbon atoms inclusive, allylamino, diallylamino, phenyl(lower)alkylamino, morpholino, lower(alkyl)morpholino, di(lower)alkylmorpholino, morpholino(lower)alkylamino, pyrrolidino, (lower)alkylpyrrolidino, di(lower)alkylpyrrolidino, N,N-hexamethyleneimino, piperidino, (lower)alkylpiperidino, di(lower)alkylpiperidino, 1,2,5,6-tetrahydropyridino, N-(lower)alkylpiperazino, N-phenylpiperazino, N-(lower)alkyl(lower)alkylpiperazino, N-(lower)alkyl-di-(lower)alkylpiperazino, furfurylamino, tetrahydrofurfurylamino, N-(lower)-alkyl-N-furfurylamino, N-alkyl-N-anilino or (lower)alkoxyanilino; $Z^1$, $Z^2$ and $Z^3$ each represent (lower)alkyl or Ar-; $R^{11}$ represents (lower)alkyl, (lower)cycloalkyl, naphthyl, benzyl, phenethyl or

and Ar represents a monovalent radical having the formula

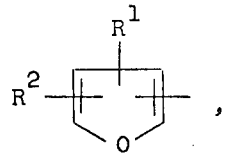

or

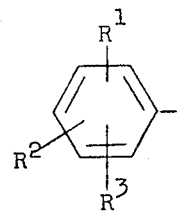

or

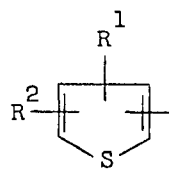

wherein $R^1$, $R^2$ and $R^3$ are each hydrogen, chloro, bromo, iodo, trifluoromethyl, phenyl, (lower)alkyl or (lower)alkoxy, but only one of said $R^1$, $R^2$ and $R^3$ groups may represent phenyl; and particularly hydrogen, hydrogen tosylate, phenylacetyl, phenoxyacetyl, carbobenzoxy, trichloroethoxycarbonyl, α-aminophenylacetyl, α-carbobenzyloxyaminophenylacetyl and, when $R^1$ and $R^2$ are taken in combination with the nitrogen atom to which they are attached, phthalimido. The same structures are also represented in some of the equations below as the acyl group

In some of the equations below esters of the carboxyl group are represented as

in such cases R is (lower)alkyl, and preferably methyl or t-butoxy, trichloroethyl, benzhydryl or benzyl.

With the above definitions in mind the preferred processes of the present invention are summarized as follows:

A. The process for producing a compound of the formula

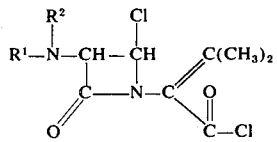

wherein $R^1$ is hydrogen or acyl and $R^2$ is hydrogen or, in combination with $R^1$ and the nitrogen atom to which they are attached, phthalimido which comprises chlorinating, [preferably wherein the chlorinating agent is chlorine, sulfuryl chloride or a complex of chlorine and pyridine hydrochloride], a compound of the formula

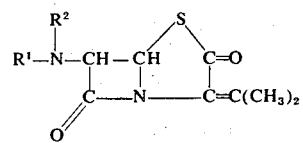

wherein $R^1$ and $R^2$ have the meaning set out above;

B. The process of producing a compound of the formula

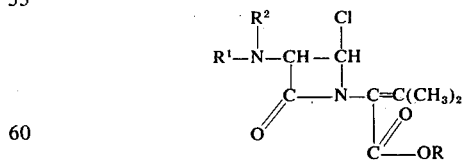

wherein $R^1$ is hydrogen or acyl; $R^2$ is hydrogen or, in combination with $R^1$ and the nitrogen atom to which they are attached, phthalimido; and R is (lower)alkyl, trichloroethyl, benzhydryl or benzyl which comprises mixing with an alcohol having the formula ROH a compound of the formula

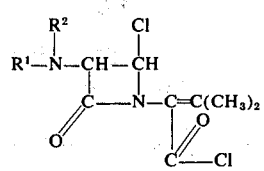

wherein R, R¹ and R² have the meaning set out above;
C. The process of producing a compound of the formula

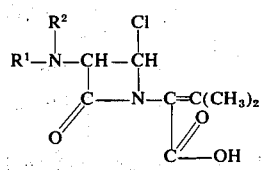

wherein R¹ is hydrogen or acyl and R² is hydrogen or, in combination with R¹ and the nitrogen atom to which they are attached, phthalimido
which comprises mixing with water
a compound of the formula

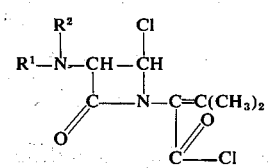

wherein R¹ and R² have the meaning set out above;
D. The process of producing a compound of the formula

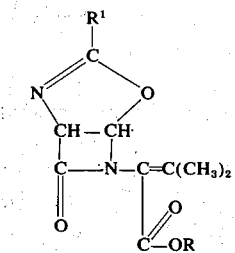

wherein R¹ is benzyl or phenoxymethyl and R is (lower)alkyl (and preferably methyl or t-butyl), trichloroethyl, benzhydryl or benzyl
which comprises mixing with alumina or silica gel
a compound of the formula

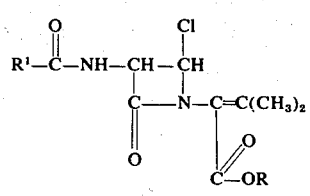

wherein R and R¹ have the meaning set out above;
E. The process of producing a compound of the formula

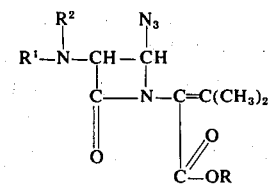

wherein R¹ is hydrogen or acyl; R² is hydrogen or, in combination with R¹ and the nitrogen atom to which they are attached, phthalimido; and R is (lower)alkyl (and preferably methyl or t-butyl), trichloroethyl, benzhydryl or benzyl which comprises reacting with azide ion
a compound of the formula

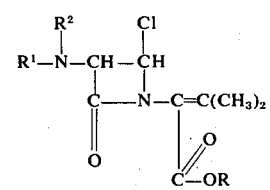

wherein R, R¹ and R² have the meaning set out above;
F. The process of producing a compound of the formula

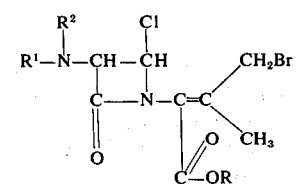

wherein R¹ is hydrogen or acyl; R² is hydrogen or, in combination with R¹ and the nitrogen atom to which they are attached, phthalimido; and R is (lower)alkyl (and preferably methyl or t-butyl), trichloroethyl, benzhydryl or benzyl
which comprises reacting with about one mole of an allylic brominating agent (and preferably wherein the allylic brominating agent is N-bromosuccinimide and a catalytic amount of an organic peroxide is present).
a compound of the formula

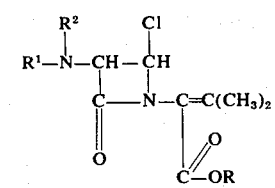

wherein R, R¹ and R² have the meaning set out above;
G. The process of producing a compound of the formula

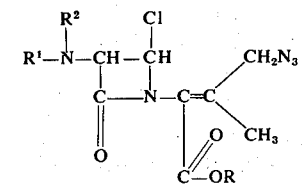

wherein $R^1$ is hydrogen or acyl; $R^2$ is hydrogen or, in combination with $R^1$ and the nitrogen atom to which they are attached, phthalimido; and R is (lower)alkyl (and preferably methyl or t-butyl), trichloroethyl, benzhydryl or benzyl
which comprises reacting with about one mole of azide ion (and preferably wherein the source of azide ion is tetramethylguanidinium azide).
a compound of the formula

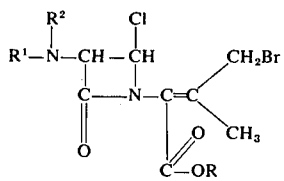

wherein R, $R^1$ and $R^2$ have the meaning set out above;
H. The process of producing a compound of the formula

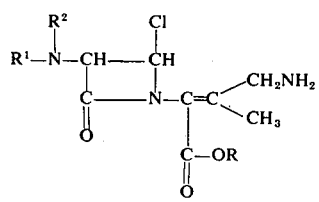

wherein $R^1$ is hydrogen or acyl; $R^2$ is hydrogen or, in combination with $R^1$ and the nitrogen atom to which they are attached, phthalimido; and R is (lower)alkyl, trichloroethyl, benzhydryl or benzyl
which comprises hydrogenating (preferably in the presence of a platinum oxide catalyst
a compound of the formula

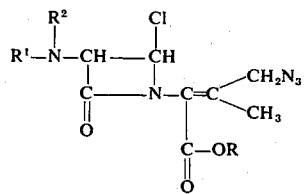

wherein R, $R^1$ and $R^2$ have the meaning set out above;
I. The process of producing a compound of the formula

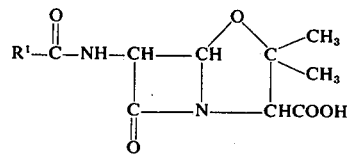

wherein $R^1$ is benzyl or phenoxymethyl
which comprises reacting with about one mole of a compound of the formula $R^2$SLi wherein $R^2$ is (lower)alkyl (and preferably n-propyl or t-butyl), in solution in the compound having the formula

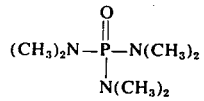

a compound of the formula

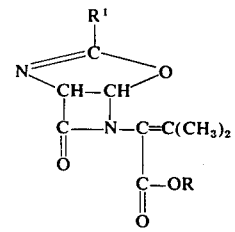

wherein $R^1$ is benzyl or phenoxymethyl and R is (lower)alkyl (and preferably methyl or t-butyl), trichloroethyl, benzhydryl or benzyl;
J. The process of producing the compound of the formula

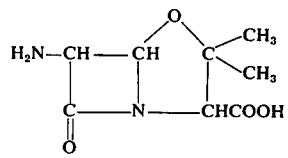

which comprises reacting with a deacylating agent a compound of the formula

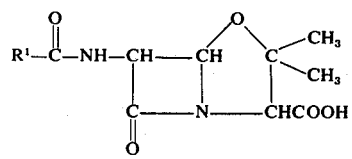

wherein $R^1$ is benzyl or phenoxymethyl and the deacylating agent is preferably S. lavendulae or E. coli or wherein the deacylation process is conducted by successive addition of trimethylchlorosilane, phosphorus pentachloride and methanol;
K. The process of producing a compound of the formula

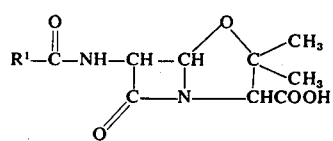

wherein

is acyl which comprises acylating the compound of the formula

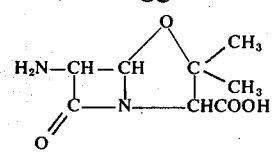

with a carboxylic acid of the formula R¹ - COOH or its equivalent as an acylating agent for a primary amino group, and especially said process in which the acylating agent is the corresponding carboxylic acid chloride, acid bromide, and anhydride, acid mixed anhydride with a (lower)alkyl ester of carbonic acid or free acid in combination with a carbodiimide, In another preferred embodiment of said process the acyl group

is

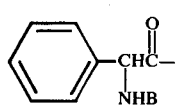

wherein B is an easily removable blocking group and especially is selected from the group consisting of hydrochloric acid, carbobenzyloxy, aliphatic β-diketones and aliphatic β-diketo esters, e.g. hydrogen chloride or methyl acetoacetate;

L. The process of producing a compound of the formula

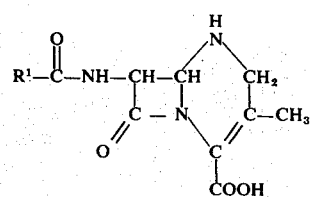

wherein

is acyl which comprises acylating the compound of the formula

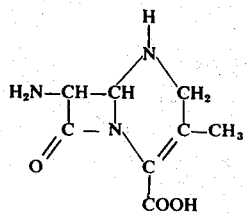

with a carboxylic acid of the formula R¹ —COOH or its equivalent as an acylating agent for a primary amino group, and especially said process in which the acylating agent is the corresponding carboxylic acid chloride, acid bromide, acid anhydride, acid mixed anhydride with a (lower)alkyl ester of carbonic acid or free acid in combination with a carbodiimide, In another preferred embodiment of said process the acyl group

is

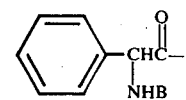

wherein B is an easily removable blocking group and especially is selected from the group consisting of hydrochloric acid, carbobenzyloxy, aliphatic β-diketones and aliphatic β-diketo esters, e.g. hydrogen chloride or methyl acetoacetate;

M. The process of producing the compound of the formula

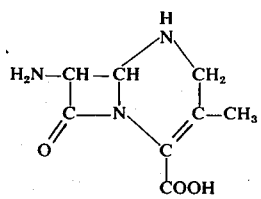

which comprises reacting with a deacylating agent a compound of the formula

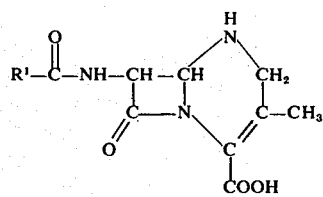

wherein R¹ is benzyl or phenoxymethyl and the deacylating agent is preferably S. lavendulae or E. coli or the deacylation process is conducted by successive addition of trimethylchlorosilane, phosphorus pentachloride and methanol; and N. The process of producing a compound of the formula

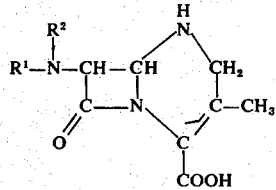

wherein R¹ is hydrogen or acyl and R² is hydrogen or, in combination with R¹ and the nitrogen atom to which they are attached, phthalimido which comprises saponifying, preferably with potassium t-butoxide. a compound of the formula

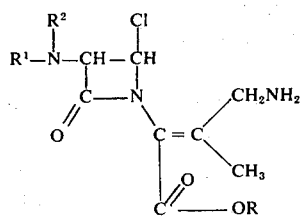

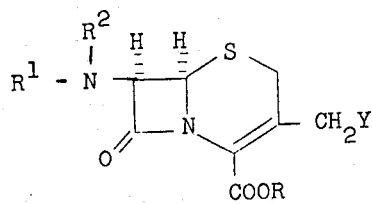

wherein R[1] and R[2] have the meaning set out above and R is (lower)alkyl, trichloroethyl, benzhydryl or benzyl.

The 4-chloroazetidine-2-ones of the present invention are useful starting materials for the preparation of the class of compounds called secopenicillins and described in detail in Belgium Pat. No. 754,125 (Farmdoc 10051S); they are converted to secopenicillins by reaction with sulfur-containing compounds such as hydrogen sulfide, sodium hydrosulfide, methyl mercaptan and benzylmercaptan or salts thereof (represented below as R[6]S[−]).

Appropriate compounds of the present invention are converted to known cephalosporins as follows:

In two preferred embodiments X is Br and Y is H or Br.

There are thus provided alternative routes from penicillins produced by direct fermentation, such as penicillins G and V, both to other penicillins and members of the cephalosporin family. As an example of the latter, where Y above is bromine, reaction with potassium 5-methyl-1,3,4-thiadiazol-2-ylthiolate followed by conversion of R[1], R[2] and R to hydrogen (if they are not such already) provides the properly 3-thiolated 7-ADCA nucleus which is then acylated in the usual manner with 1-tetrazolylacetic acid to produce cephazolin. As another example of the latter, when Y is hydrogen the product contains the nucleus 7-ADCA (7-aminodesacetoxycephalosporanic acid). Thus when R[2] is hydrogen and R[1] is

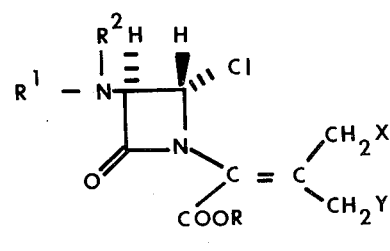

wherein R[1], R[2], and R have the meanings disclosed above and X is Cl, Br, OAc, OCH$_2\phi$, N$_3$, NH$_2$, $-O-\overset{O}{\underset{\|}{C}}-H$, OH, -SCN, -SeCN, -SeH or $-\overset{O}{\underset{\|}{P}}(OCH_2Ph)_2$ and Y is H or the same as X.

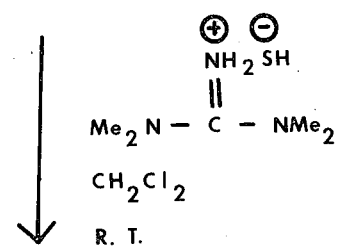

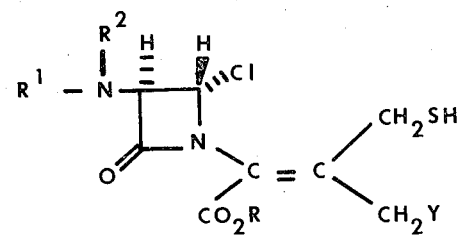

base e. g. tertiary amines, NaH, potassium t-butoxide or a sodium alcoholate

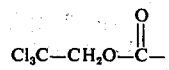

treatment with zinc and acetic acid produces an ester of 7-ADCA which can be cleaved in the usual manner to give 7-ADCA itself.

As another example, cephalexin itself is produced by the same sequence of reactions in which X is Br, Y is H and $R^1$ and $R^2$ taken together with the nitrogen atom represent the group

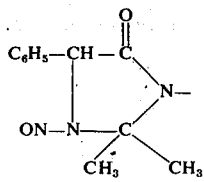

The anhydropenicillin used in that case as the original starting material is prepared either by treating N-nitrosohetacillin (prepared according to Belgium Pat. No. 765,596, Farmdoc 67,311S) in the usual manner for converting a penicillin to an anhydro-penicillin or by coupling D-(-)-2-phenylglycine (as with a carbodiimide) with the compound of U.S. Pat. No. 3,311,638 having the structure

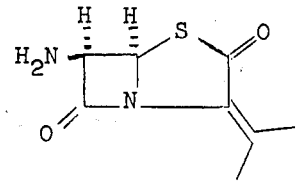

followed by formation of its acetone adduct and then nitrosation according to Belgium Pat. No. 765,596, Farmdoc 67,511S.

Appropriate compounds of the present invention are used to prepare previously known compounds in the penicillin series, including penicillins themselves, as illustrated by the following reactions:

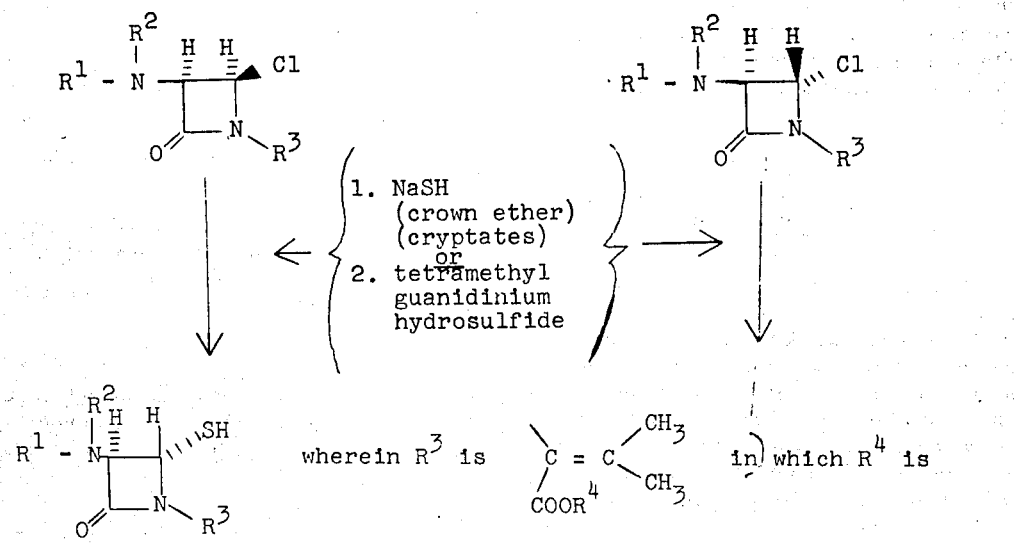

hydrogen, (lower)alkyl, trichloroethyl, benzhydryl or benzyl,

conversion to a penicillin per Wolfe et al., J. Amer. Chem. Soc. 91, 7205 (1969), when $-R^3 = \begin{matrix} \diagdown \\ C = C \\ \diagup \\ COOH \end{matrix} \begin{matrix} CH_3 \\ \diagdown \\ \diagup \\ CH_3 \end{matrix}$, $R^2$ = H and $R^1$ = acyl when $R^2$ = H and $R^1$ = acyl, that is, $R^5$-COOH as per R.D.G. Cooper and F.L. José, J. Am. Chem Soc., 92, 2575 (1970)

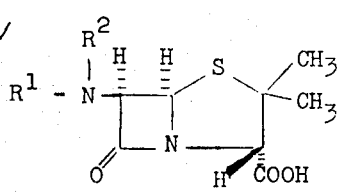

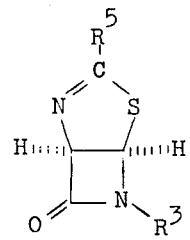

Another procedure produces secopenicillins as follows:

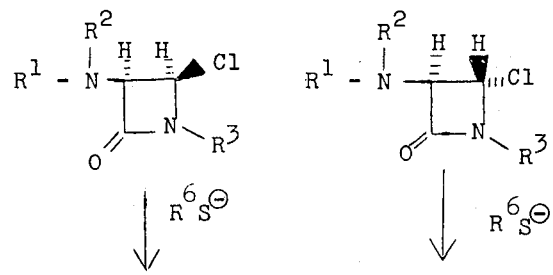

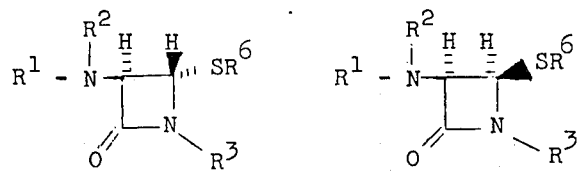

When $R^6$ is benzyl it is converted to hydrogen by catalytic hydrogenation to furnish another route to the sulfhydryl compounds above.

In the above equations -$R^3$ is preferably

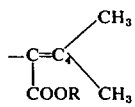

and $R^1$, $R^2$, $R^3$ and $R^4$ have the meaning used previously herein.

In the treatment of bacterial infections in man, the new, bicyclic β-lactam antibiotics of this invention, e.g. the oxapenicillins and the azacephalosporins are administered orally or parenterally, in accordance with conventional procedures for antibiotic administration, in an amount of from about 5 to 200 mg./kg./day and preferably about 5 to 20mg./kg./day in divided dosage, e.g., three to four times a day. They are administered in dosage units containing, for example, 125 or 250 or 500 mg. of active ingredient with suitable physiologically acceptable carriers or excipients. The dosage units are in the form of liquid preparations such as solutions or suspensions or as solids in tablets or capsules.

The substituted azetidine-2-ones of the present invention are not active as antibacterial agents but do function as inhibitors of the enzyme β-lactamase and thus decrease the rate of destruction of a penicillin when used in combination therewith. This is demonstrated, for example, by reduction of the Minimum Inhibitory Concentration of ampicillin versus "resistant" or β-lactamase producing bacteria such as P. morganii and Ps. aeruginosa from values in the range of 500–1000 mcg./ml. to values as low as 125 mcg./ml. using concentrations of the substituted azetidine-2-one in the range of about 125 mcg./ml. These particular figures were obtained using the compound having the structure

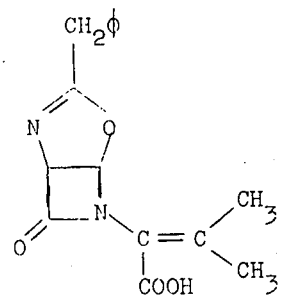

I claim:
1. The compound of the formula

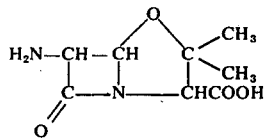

2. A nontoxic, pharmaceutically acceptable metallic, ammonium or substituted ammonium salt of the compound of the formula

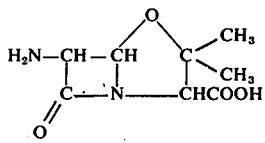

* * * * *